(12) United States Patent
Lanigan et al.

(10) Patent No.: US 9,308,318 B2
(45) Date of Patent: *Apr. 12, 2016

(54) INFUSION PUMP ASSEMBLY

(71) Applicant: DEKA Products Limited Partnership, Manchester, NH (US)

(72) Inventors: Richard J. Lanigan, Concord, NH (US); Marc A. Mandro, Bow, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/500,082

(22) Filed: Sep. 29, 2014

(65) Prior Publication Data

US 2015/0018768 A1   Jan. 15, 2015

Related U.S. Application Data

(63) Continuation of application No. 12/413,234, filed on Mar. 27, 2009, now Pat. No. 8,845,587, which is a continuation of application No. 12/249,891, filed on Oct. 10, 2008, now Pat. No. 8,034,026, which is a continuation-in-part of application No. 11/533,882, filed on Sep. 21, 2006, now Pat. No. 9,173,996, which is a continuation of application No. 10/151,733, filed on May 20, 2002, now abandoned, and a continuation-in-part of application No. 10/037,614, filed on Jan. 4, 2002, now Pat. No. 7,306,578.

(60) Provisional application No. 60/291,881, filed on May 18, 2001.

(51) Int. Cl.
| | |
|---|---|
| A61M 5/142 | (2006.01) |
| A61M 5/145 | (2006.01) |
| A61M 5/50 | (2006.01) |
| A61M 5/14 | (2006.01) |
| A61M 25/06 | (2006.01) |
| A61M 39/10 | (2006.01) |
| A61M 39/14 | (2006.01) |

(52) U.S. Cl.
CPC ........... *A61M 5/14244* (2013.01); *A61M 5/145* (2013.01); *A61M 5/1452* (2013.01); *A61M 5/1456* (2013.01); *A61M 5/14586* (2013.01); *A61M 5/5086* (2013.01); *A61M 5/14* (2013.01); *A61M 5/142* (2013.01); *A61M 25/0612* (2013.01); *A61M 39/1011* (2013.01); *A61M 39/14* (2013.01); *A61M 2005/14268* (2013.01); *A61M 2005/14573* (2013.01); *A61M 2205/3306* (2013.01); *A61M 2205/50* (2013.01); *Y10T 29/494* (2015.01); *Y10T 29/49826* (2015.01)

(58) Field of Classification Search
CPC ......... A61M 2005/14573; A61M 2005/14268; A61M 5/1456; A61M 2205/3306
USPC .................................. 604/67, 131–155, 224
See application file for complete search history.

(56) References Cited

U.S. PATENT DOCUMENTS

| | | | | |
|---|---|---|---|---|
| 4,435,173 | A * | 3/1984 | Siposs ................. | A61M 5/1456 128/DIG. 1 |
| 2004/0064088 | A1 * | 4/2004 | Gorman et al. ............ | 604/93.01 |

(Continued)

*Primary Examiner* — Gerald Landry, II
(74) *Attorney, Agent, or Firm* — Michelle Saquet Temple

(57) ABSTRACT

An infusion pump assembly is disclosed. The infusion pump assembly includes a locking tab and a pump barrel inside a pump barrel housing, where the pump barrel accommodates a reservoir assembly. The reservoir assembly includes a reservoir and a plunger rod. The infusion pump assembly also includes a locking disc at a terminus of the pump barrel. The locking disc includes a clearance hole for the plunger rod. The locking disc also includes at least one locking tab notch in close proximity with the locking tab. The locking tab is in moveable engagement with the locking tab notch, and the reservoir moves the locking tab from a locked position to an unlocked position when the plunger rod is inserted through clearance hole. The locking disc rotates upon torque being applied to the reservoir assembly, the locking disc rotating from a non-loaded position to a loaded position with respect to the plunger rod and a drive screw.

12 Claims, 63 Drawing Sheets

(56) References Cited

U.S. PATENT DOCUMENTS

2007/0073229 A1* 3/2007 Gorman et al. ............... 604/131
2008/0077081 A1* 3/2008 Mounce .............. A61M 5/1413
                                                        604/67
2008/0097381 A1* 4/2008 Moberg et al. ................ 604/506

* cited by examiner

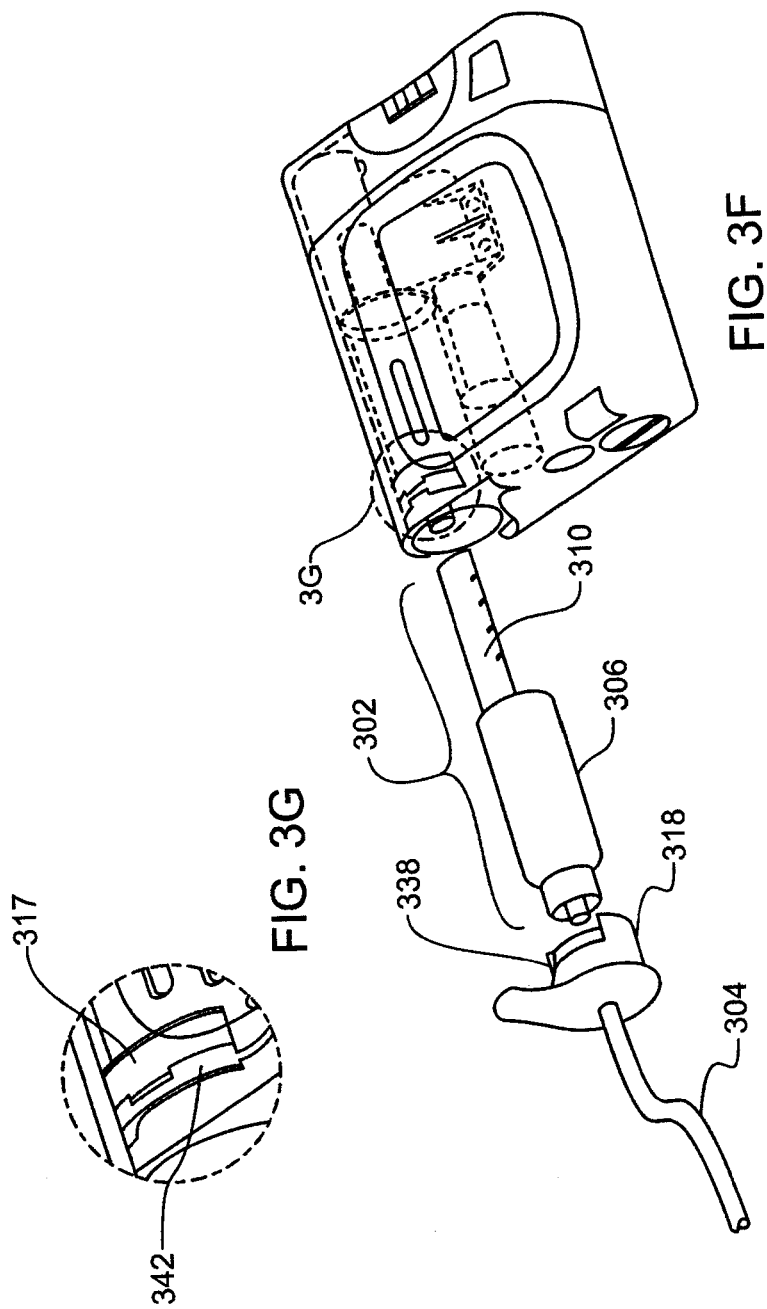

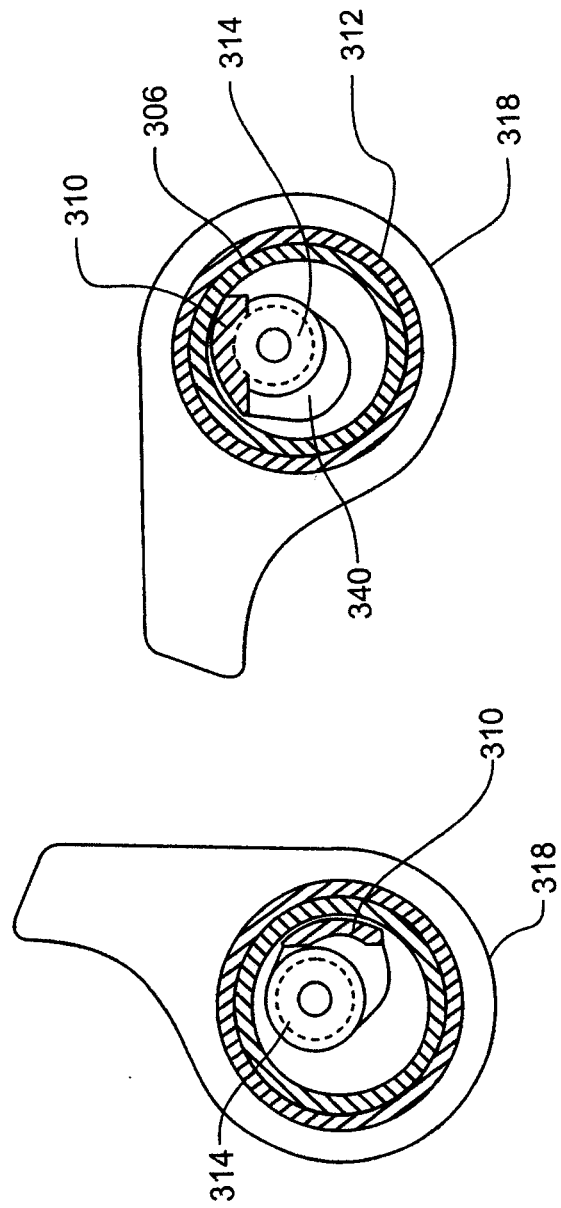

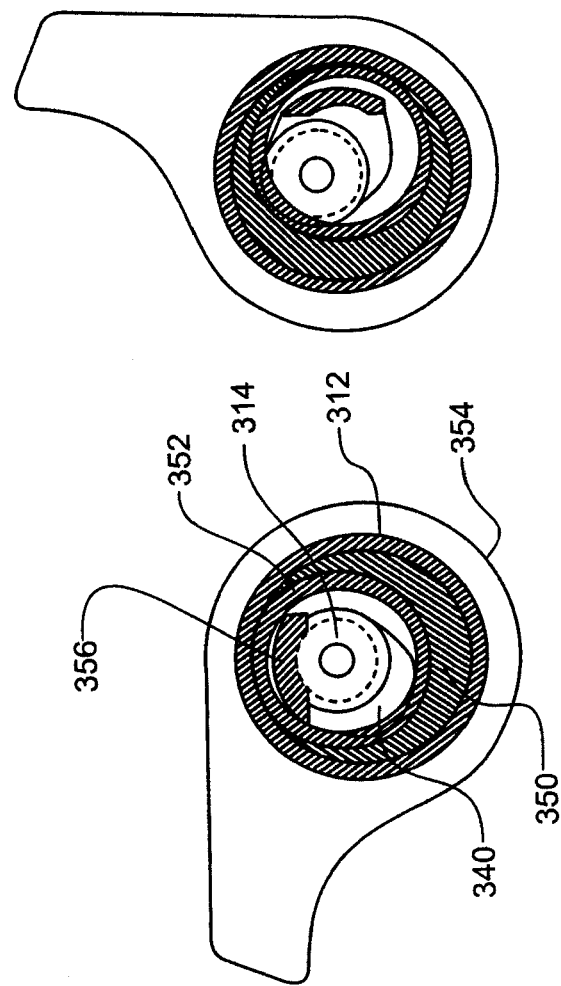

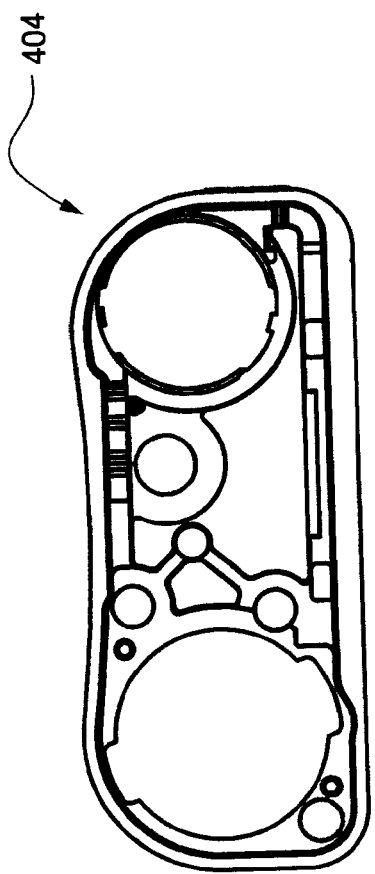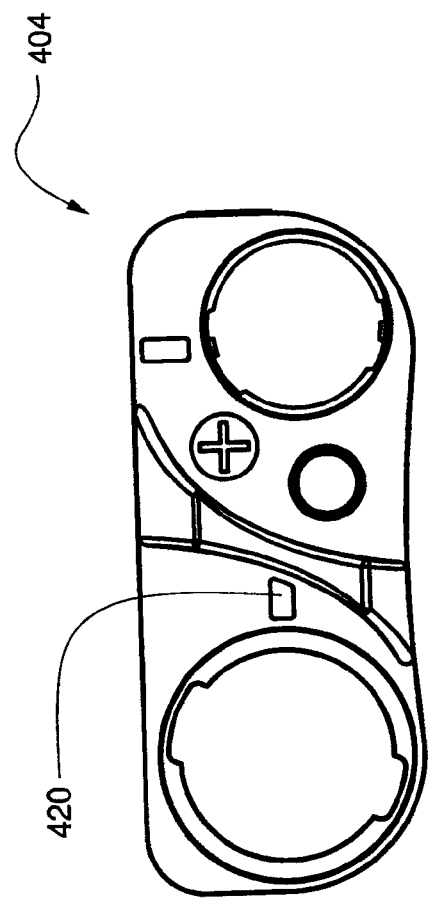

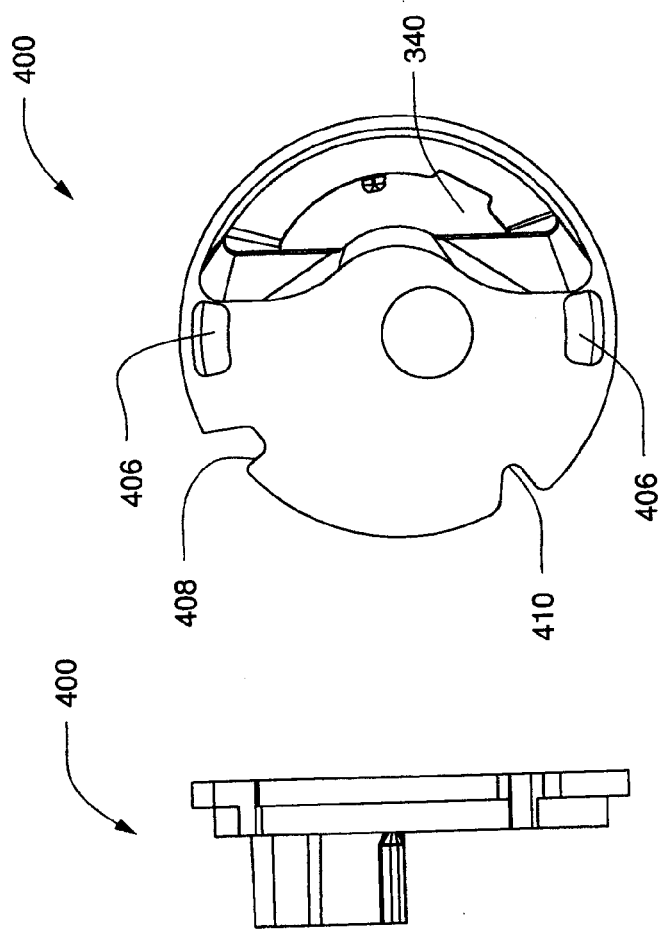
FIG. 4I
FIG. 4H
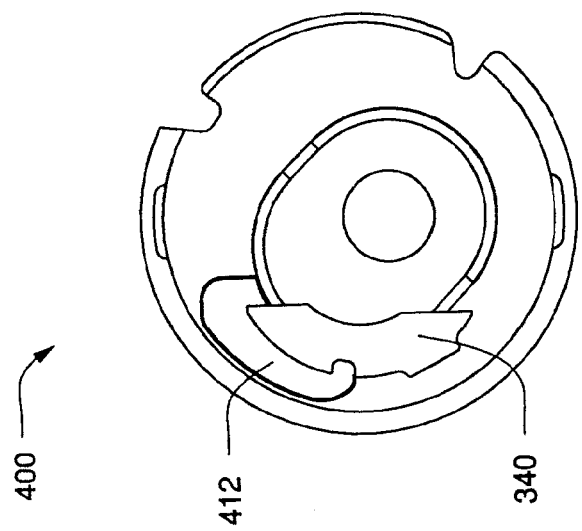
FIG. 4G

506

506

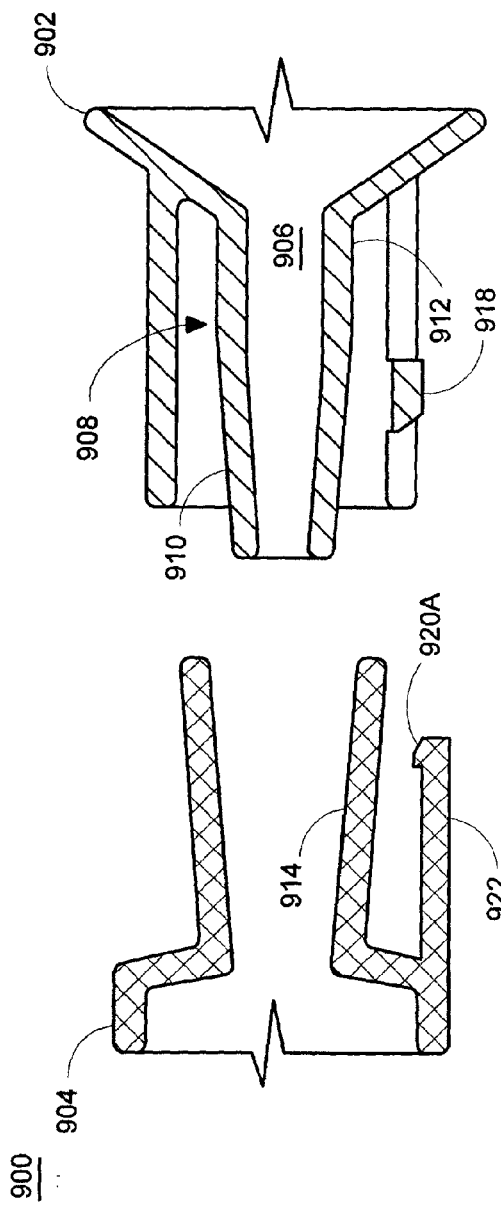
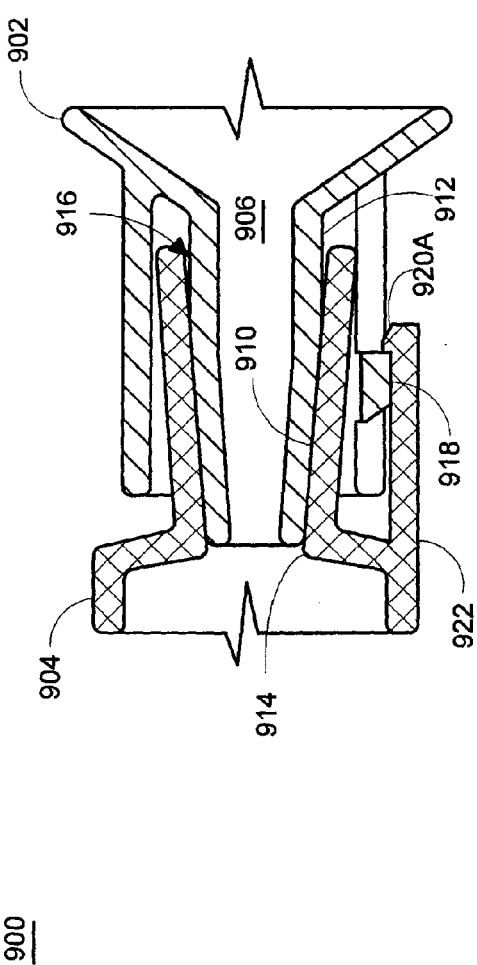
FIG. 9A
FIG. 9B

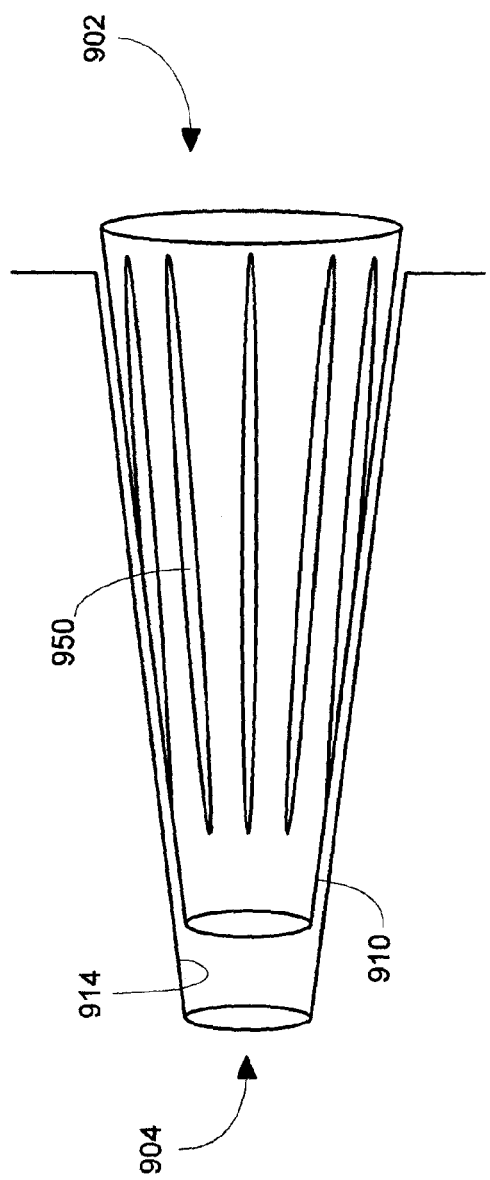
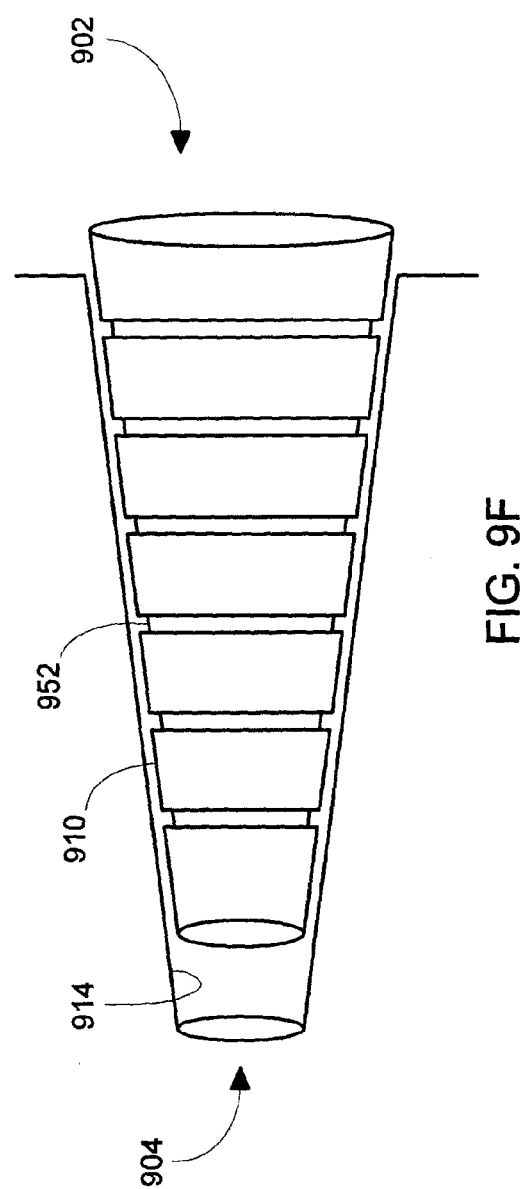

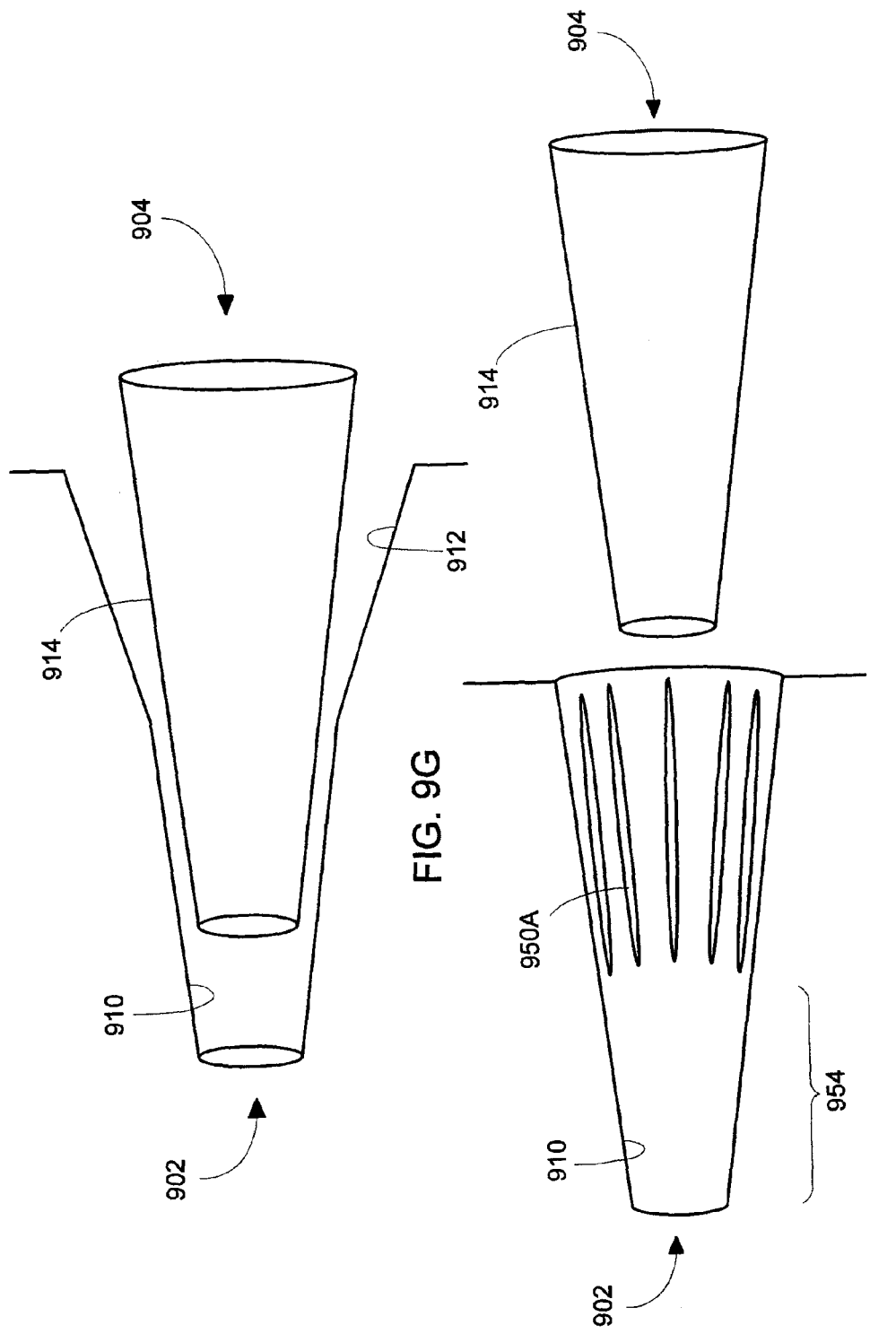

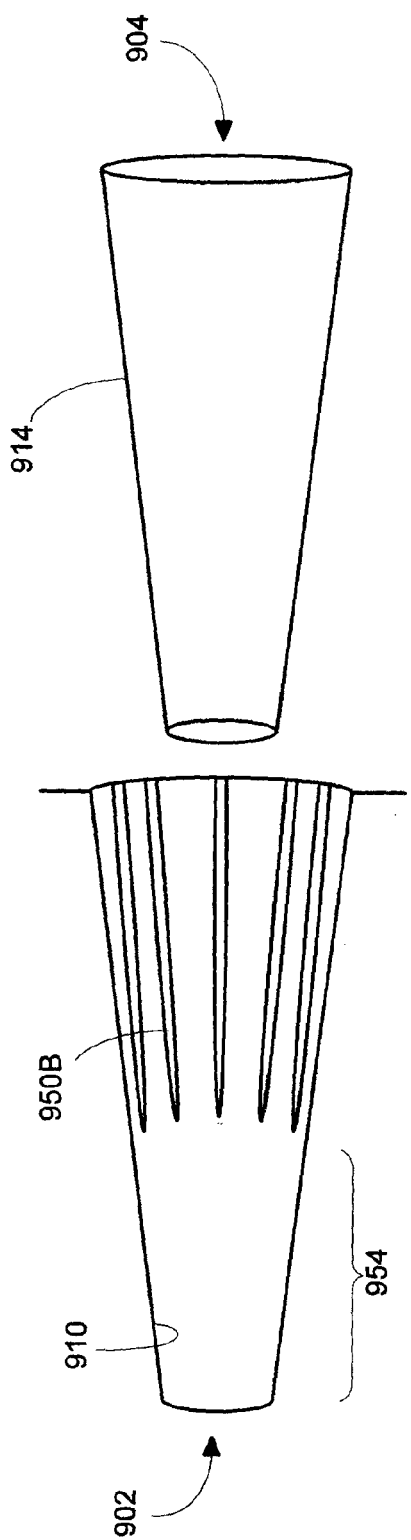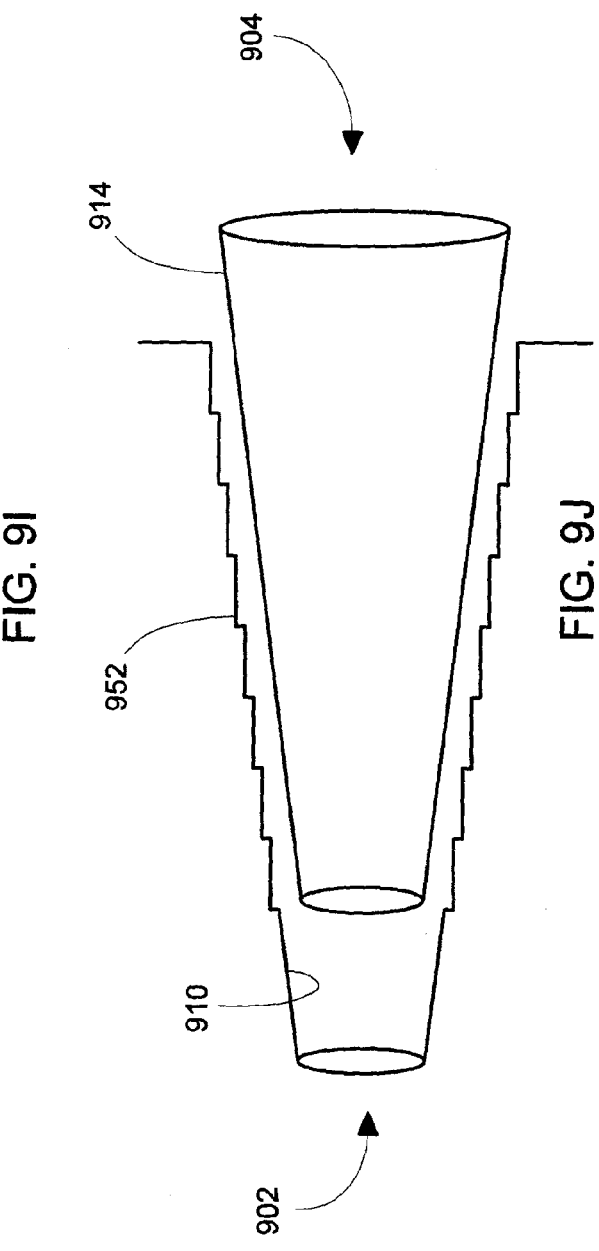

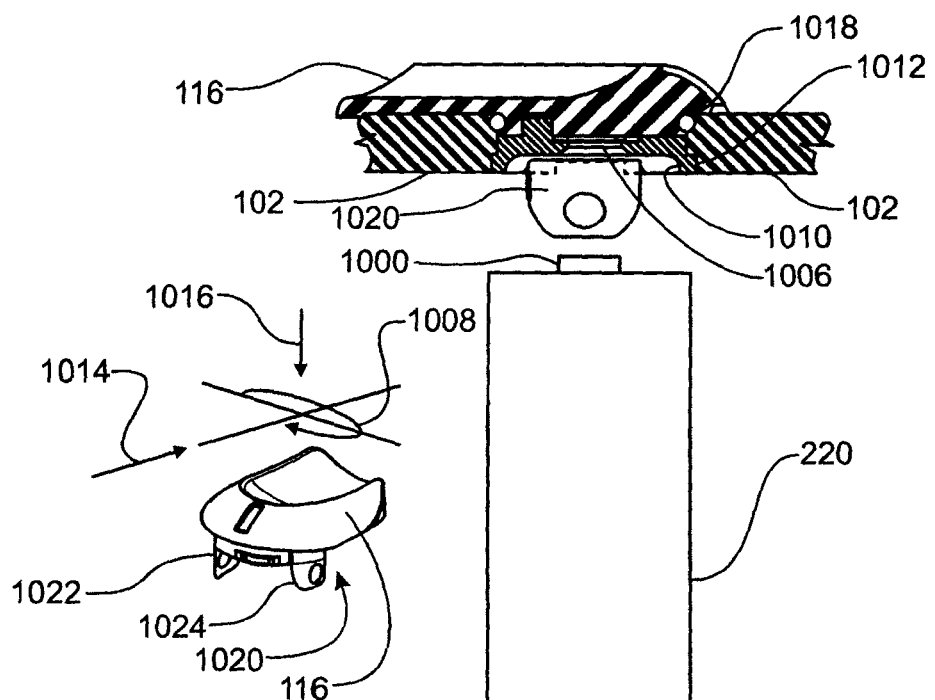
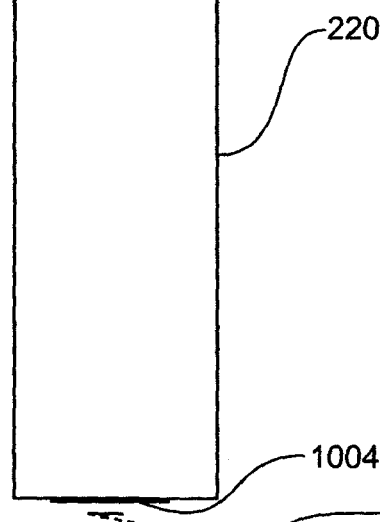
FIG. 10A
FIG. 10C
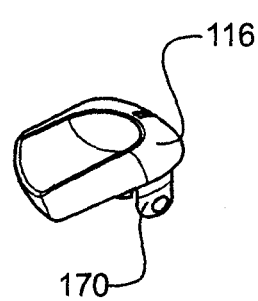
FIG. 10B

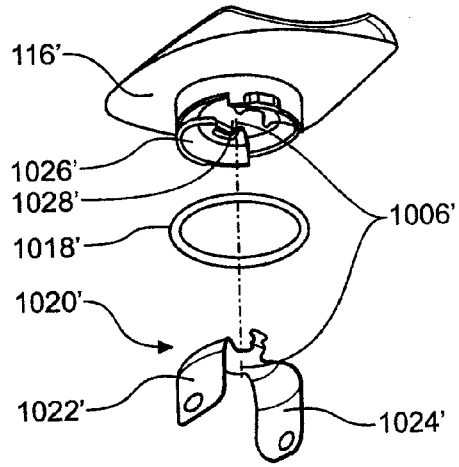
FIG.12A
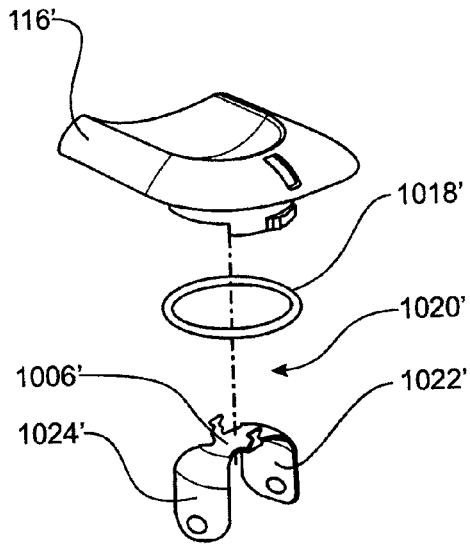
FIG.12B
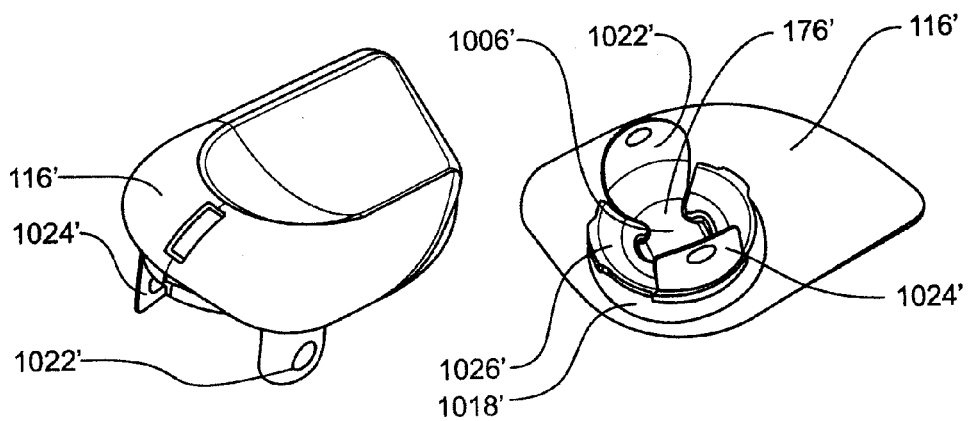
FIG.12C
FIG.12D

| TITLE | Initial | Final | Rate-of-Change |
|---|---|---|---|
| FR01 | 0.00 lbs. | 0.00 lbs. | 0.00 lbs. |
| FR02 | 0.00 lbs. | 0.00 lbs. | 0.00 lbs. |
| FR03 | 0.00 lbs. | 0.00 lbs. | 0.00 lbs. |
| FR04 | 0.00 lbs. | 0.00 lbs. | 0.00 lbs. |
| FR05 | 0.00 lbs. | 0.00 lbs. | 0.00 lbs. |
| FR06 | 0.00 lbs. | 0.00 lbs. | 0.00 lbs. |
| FR07 | 0.00 lbs. | 0.00 lbs. | 0.00 lbs. |
| FR08 | 0.00 lbs. | 0.00 lbs. | 0.00 lbs. |
| FR09 | 0.00 lbs. | 0.00 lbs. | 0.00 lbs. |
| FR10 | 0.00 lbs. | 0.00 lbs. | 0.00 lbs. | o o o

| FR31 | 0.00 lbs. | 0.00 lbs. | 0.00 lbs. |
|---|---|---|---|
| FR32 | 0.00 lbs. | 0.00 lbs. | 0.00 lbs. |
| FR33 | 0.00 lbs. | 0.00 lbs. | 0.00 lbs. |
| FR34 | 0.00 lbs. | 0.50 lbs. | 0.50 lbs. |
| FR35 | 0.50 lbs. | 1.05 lbs. | 0.55 lbs. |
| FR36 | 1.05 lbs. | 1.80 lbs. | 0.75 lbs. |
| FR37 | 1.80 lbs. | 2.30 lbs. | 0.50 lbs. |
| FR38 | 2.30 lbs. | 3.10 lbs. | 0.80 lbs. |
| FR39 | 3.10lbs. | 3.80 lbs. | 0.70 lbs. |
| FR40 | 3.80 lbs. | 4.20 lbs. | 0.40 lbs. |
| AFR | — | — | 0.105 lbs. |

FIG. 18 ized position when the plunger rod is inserted through clearance hole. The locking disc rotates upon torque being applied to the reservoir assembly, the locking disc rotating from a non-loaded position to a loaded position with respect to the plunger rod and a drive screw.

INFUSION PUMP ASSEMBLY

CROSS-REFERENCE TO RELATED APPLICATIONS

This application is a Continuation of U.S. patent application Ser. No. 12/413,234, filed Mar. 27, 2009 and entitled Infusion Pump Assembly, now U.S. Pat. No. 8,845,587, issued Sep. 30, 2014, which is a Continuation of U.S. patent application Ser. No. 12/249,891, filed Oct. 10, 2008 and entitled Infusion Pump Assembly, now U.S. Pat. No. 8,034, 026, issued Oct. 11, 2011, which is a Continuation-In-Part of U.S. patent application Ser. No. 11/533,882, filed Sep. 21, 2006 and entitled Infusion Set for a Fluid Pump, now U.S. Publication No. US-2007-0049870-A1, published Mar. 1, 2007, which is a Continuation Application of U.S. patent application Ser. No. 10/151,733, filed May 20, 2002 and entitled Infusion Set for a Fluid Pump, which is now U.S. Publication No. US/2002-0173769 published Nov. 21, 2002, which is now abandoned. U.S. patent application Ser. No. 11/533,882 also claims priority from U.S. Provisional Patent Application No. 60/291,881, filed May 18, 2001 and entitled Cannula Designs for Insulin Pump Systems, each of which are hereby incorporated herein by reference in their entireties.

U.S. patent application Ser. No. 10/151,733 is a Continuation-In-Part Application of U.S. patent application Ser. No. 10/037,614, filed Jan. 4, 2002 and entitled Loading Mechanism for Infusion Pump, now U.S. Pat. No. 7,306,578, issued Dec. 11, 2007 (C54). U.S. patent application Ser. No. 10/151, 733 also claims priority from U.S. Provisional Patent Application No. 60/291,881, filed May 18, 2001 and entitled Cannula Designs for Insulin Pump Systems (C63), both of which are hereby incorporated herein by reference in their entireties.

TECHNICAL FIELD

This disclosure relates to pump assemblies and, more particularly, to infusion pump assemblies.

BACKGROUND

An infusion pump assembly may be used to infuse a fluid (e.g., a medication or nutrient) into a user. The fluid may be infused intravenously (i.e., into a vein), subcutaneously (i.e., into the skin), arterially (i.e., into an artery), and epidurally (i.e., into the epidural space).

Infusion pump assemblies may administer fluids in ways that would be impractically expensive/unreliable if performed manually by nursing staff. For example, an infusion pump assembly may repeatedly administer small quantities of an infusible fluid (e.g., 0.1 mL per hour), while allowing the user to request one-time larger "bolus" doses.

SUMMARY OF DISCLOSURE

In accordance with one aspect of the present invention, an infusion pump assembly is disclosed. The infusion pump assembly includes a locking tab, and a pump barrel inside a pump barrel housing, where the pump barrel accommodates a reservoir assembly. The reservoir assembly includes a reservoir and a plunger rod. The infusion pump assembly also includes a locking disc at a terminus of the pump barrel. The locking disc includes a clearance hole for the plunger rod. The locking disc also includes at least one locking tab notch in close proximity with the locking tab. The locking tab is in moveable engagement with the locking tab notch, and the reservoir moves the locking tab from a locked position to an unlocked position when the plunger rod is inserted through clearance hole. The locking disc rotates upon torque being applied to the reservoir assembly, the locking disc rotating from a non-loaded position to a loaded position with respect to the plunger rod and a drive screw.

Some embodiments of this aspect of the present invention may include one or more of the following features. The locking disc may further include a second locking tab notch, wherein the second locking tab notch is engaged with the locking tab when the locking disc is in the loaded position. The locking disc may further include a plunger rod support. The plunger rod support may be in close relation with the plunger rod when the plunger rod is inserted through the clearance hole. The locking disc may further include at least two reservoir tab openings for mating with at least two reservoir alignment tabs on the reservoir. The reservoir assembly may further include a locking hub. The locking hub may fluidly connected to the reservoir. The locking hub may further include at least two locking hub alignment tabs, the locking hub alignment tabs aligning with the reservoir alignment tabs when the locking hub is fluidly connected to the reservoir. The infusion pump assembly may further include a hub and battery end cap. The end cap may have an opening to the pump barrel. The pump barrel opening may be complementary to the locking hub alignment tabs wherein the loading of the reservoir assembly may provide alignment of the reservoir alignment tabs with the reservoir tab openings and the plunger rod with the clearance hole. The hub and battery end cap may further include a first alignment feature. The first alignment feature may be complementary to a second alignment feature on the reservoir. When the first and second alignment features are aligned, the locking hub alignment tabs may also be aligned with the hub and battery cap opening.

In accordance with one aspect of the present invention, a reservoir assembly is disclosed. The reservoir assembly includes a reservoir, the reservoir having an interior volume and terminating with a male feature on a first end. Also, the reservoir assembly includes a plunger rod, the plunger rod including a threaded portion and a notched portion. The assembly further includes a reservoir bottom, the reservoir bottom having a plunger rod opening, and at least two reservoir alignment tabs, wherein the plunger rod extends through the plunger rod opening.

Some embodiments of this aspect of the present invention may include one or more of the following features. The reservoir assembly may further include an alignment feature on the reservoir. The alignment feature may allow aligning the reservoir assembly with an infusion pump assembly for loading the reservoir assembly into the infusion pump assembly. A removable filling aid may be included having a threaded portion and a handle portion. The threaded portion may thread to the threaded portion of the plunger rod.

In accordance with one aspect of the present invention, a method of loading a reservoir assembly to a drive mechanism of an infusion pump assembly is disclosed. The method includes aligning locking tab alignment features of a reservoir and locking tab assembly with an alignment feature on a hub and battery end cap of the infusion pump assembly, applying pressure to the locking tab of the reservoir and locking tab assembly, and rotating the locking tab until the locking tab is flush with the infusion pump assembly. Rotating the locking tab loads the reservoir and locking hub assembly onto the drive mechanism of the infusion pump assembly.

The details of one or more implementations are set forth in the accompanying drawings and the description below. Other

Figure 1A:
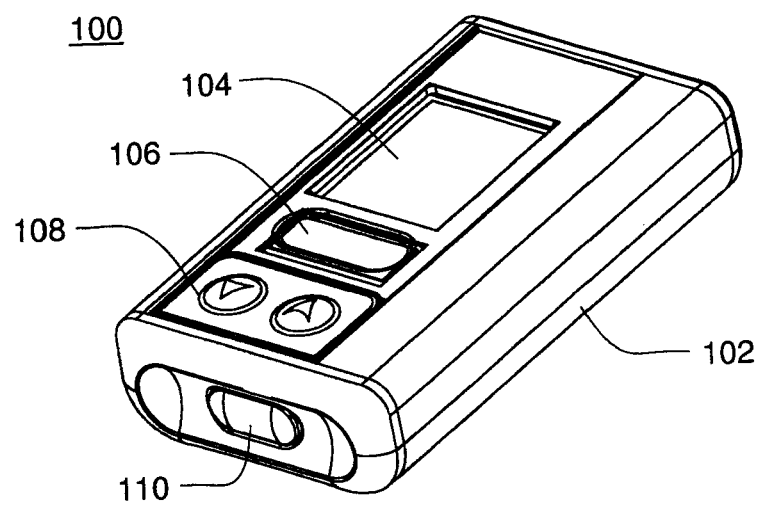
FIGS. 1A-1B are front and back isometric views of an infusion pump assembly.
Figure 1B:
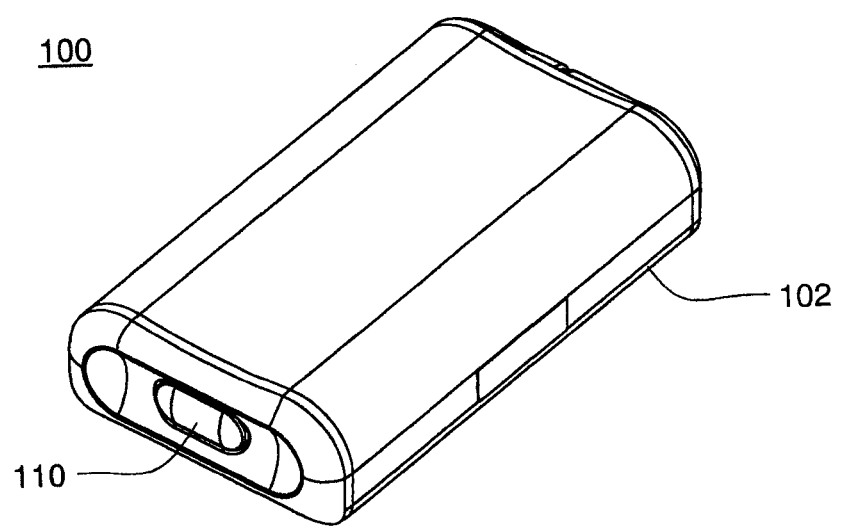
Figure 1E:
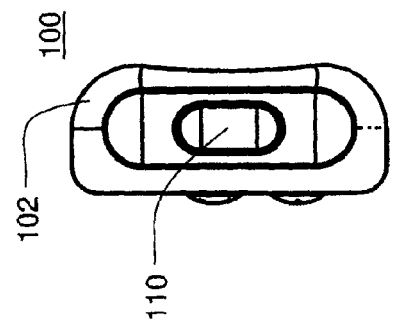
FIGS. 1C-1E are side and front views of the infusion pump assembly of FIG. i.
Figure 1D:
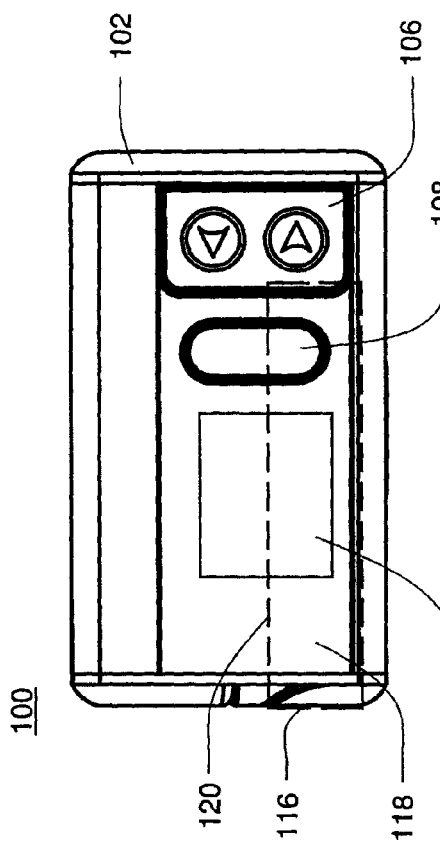
Figure 1C:
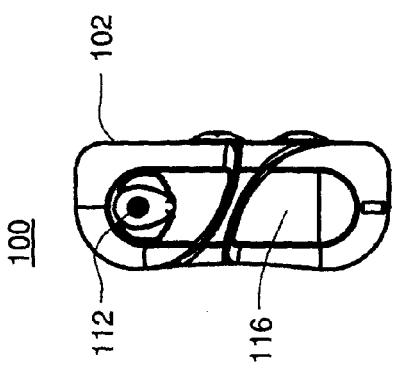
Figure 1F:
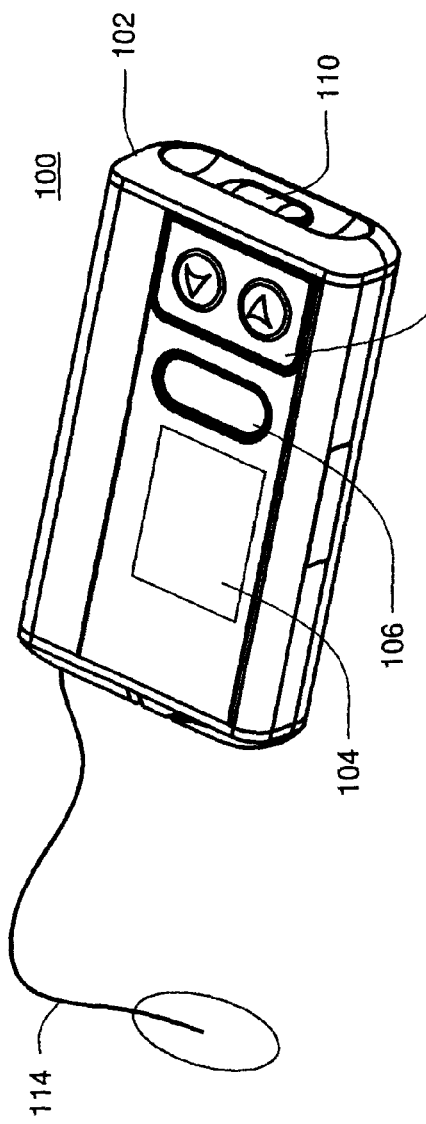
Figure 2:
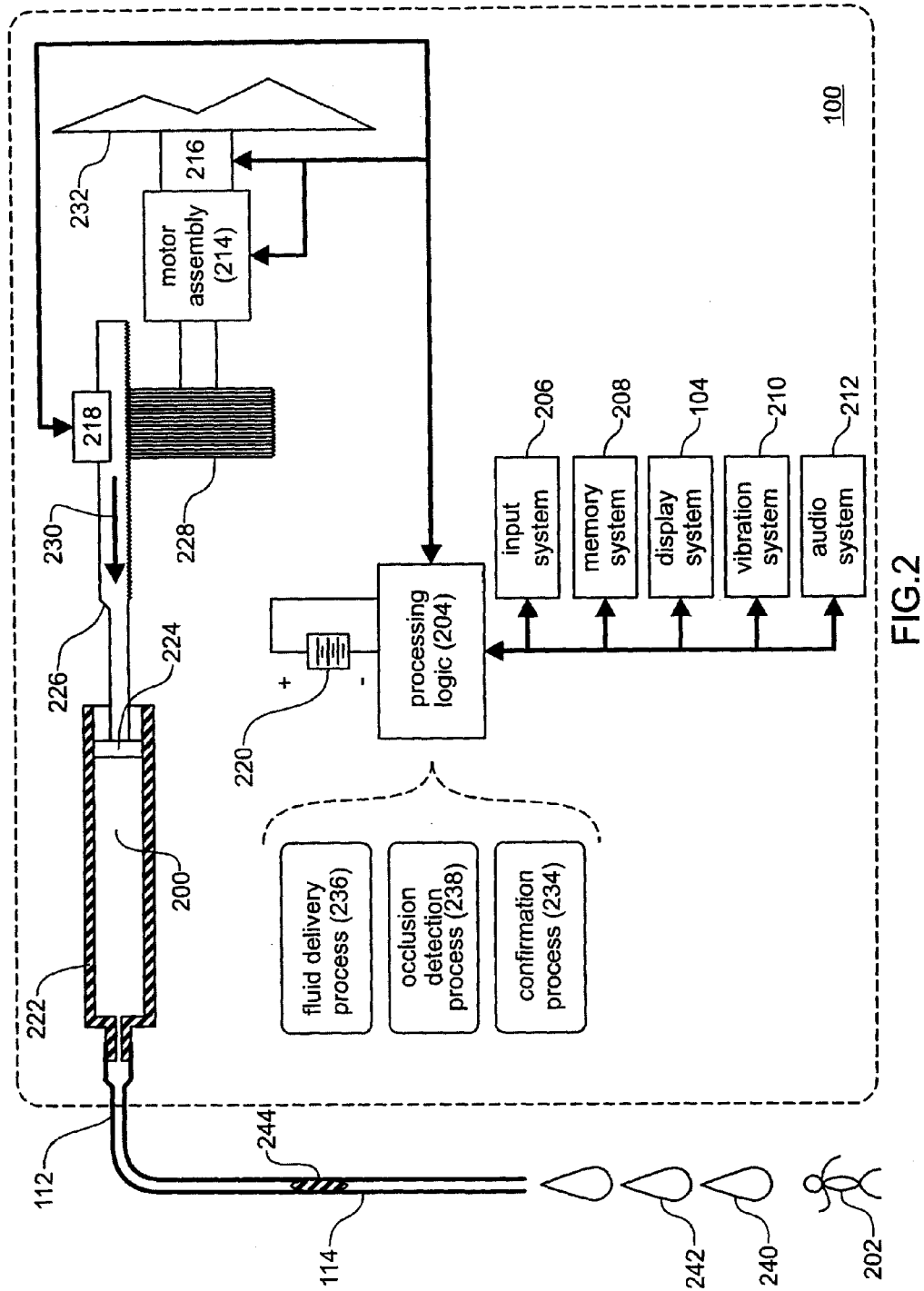
Figure 3A:
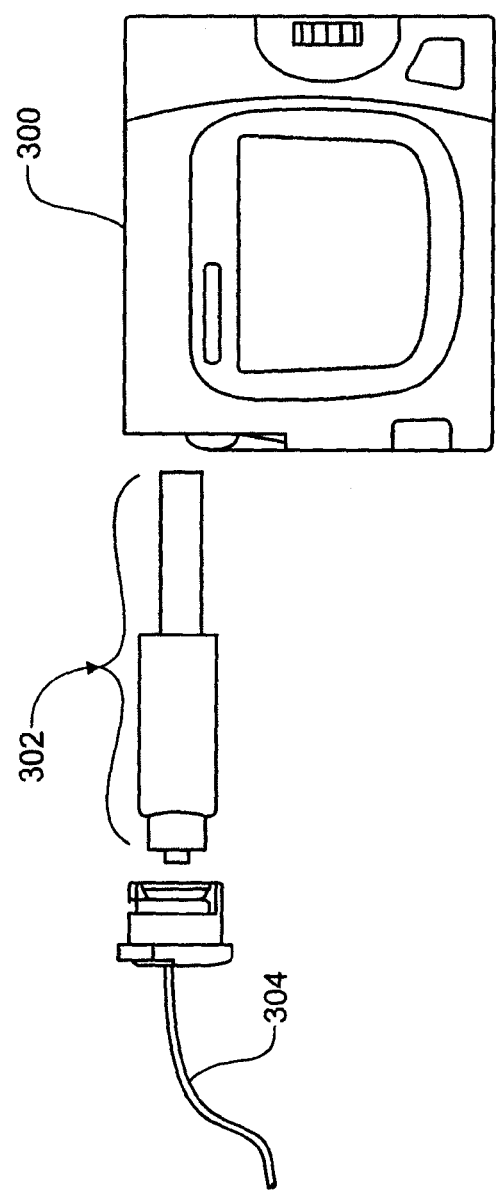
Figure 3B:
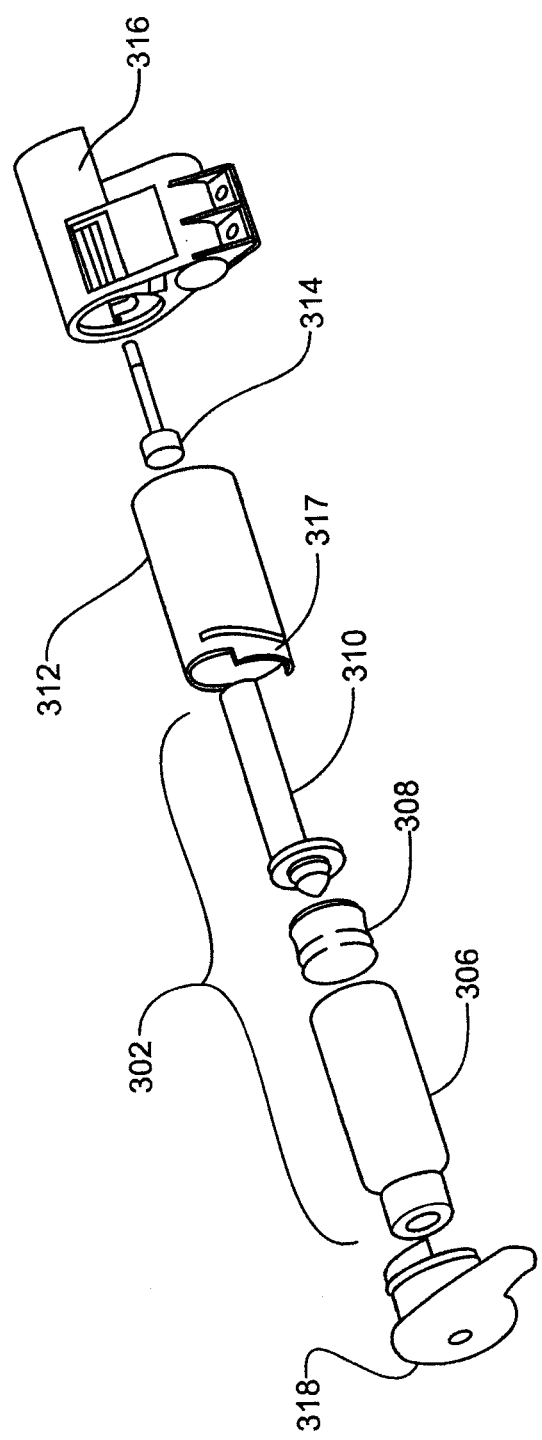
Figure 3C:
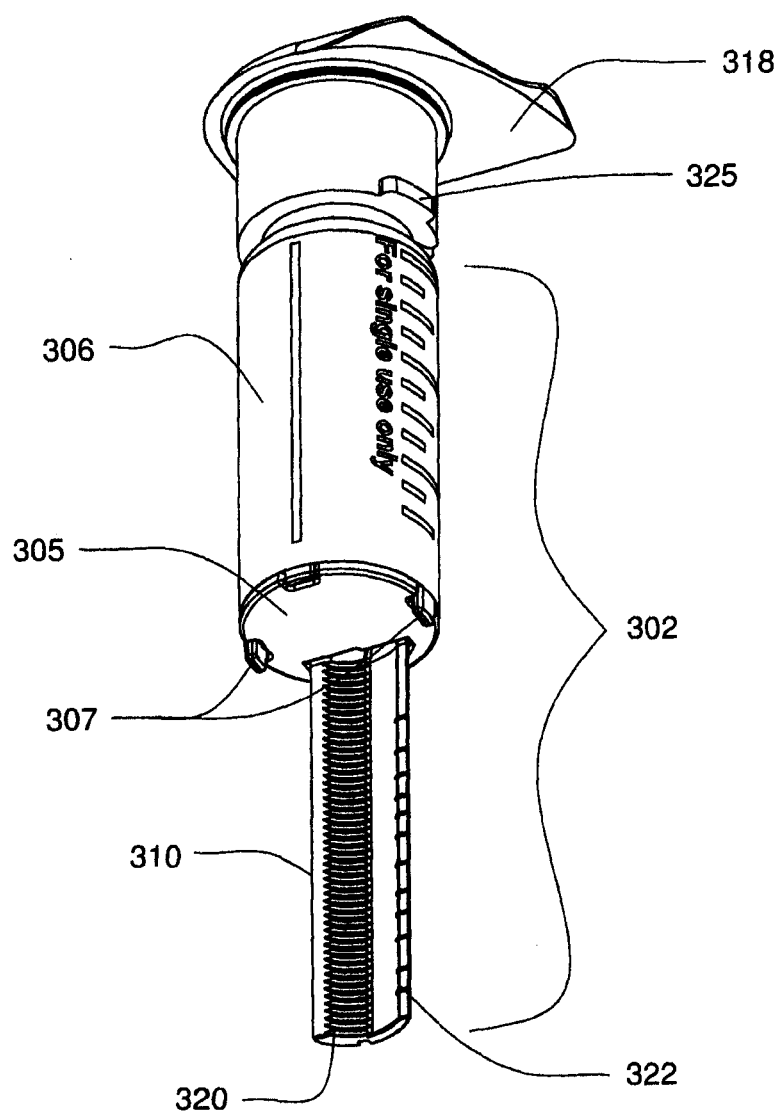
Figure 3D:
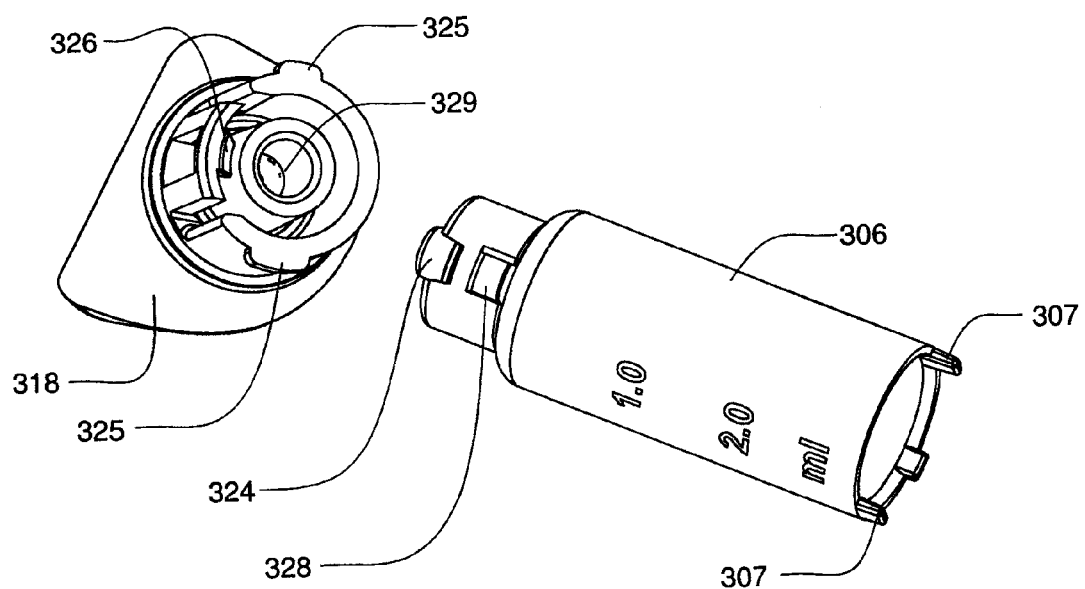
Figure 3E:
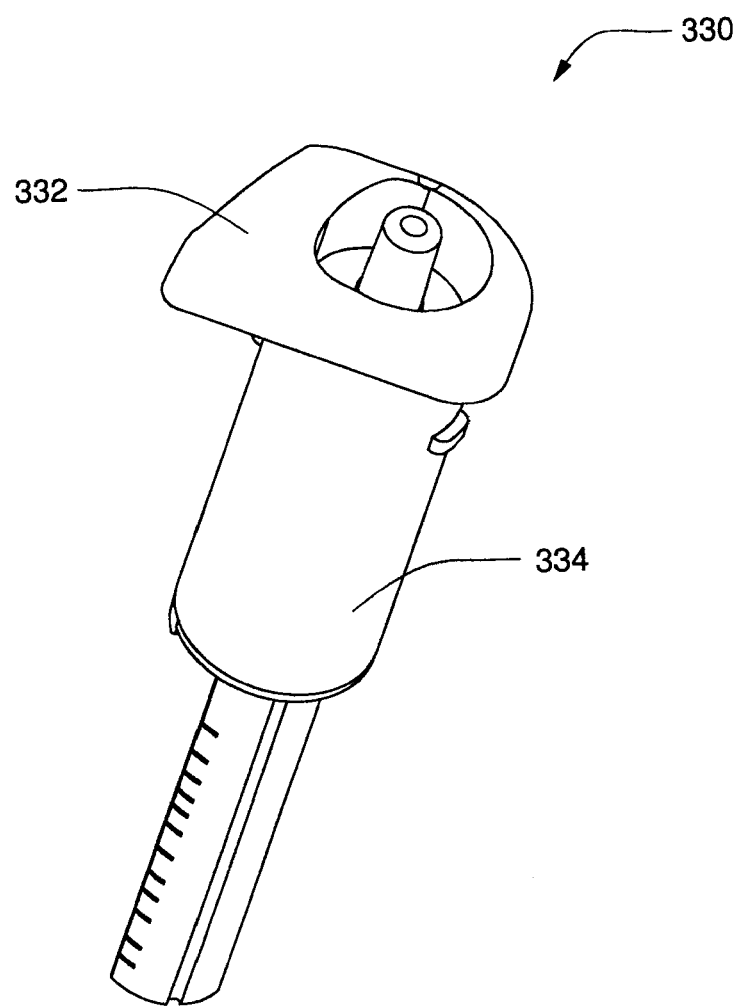
Figure 3J:
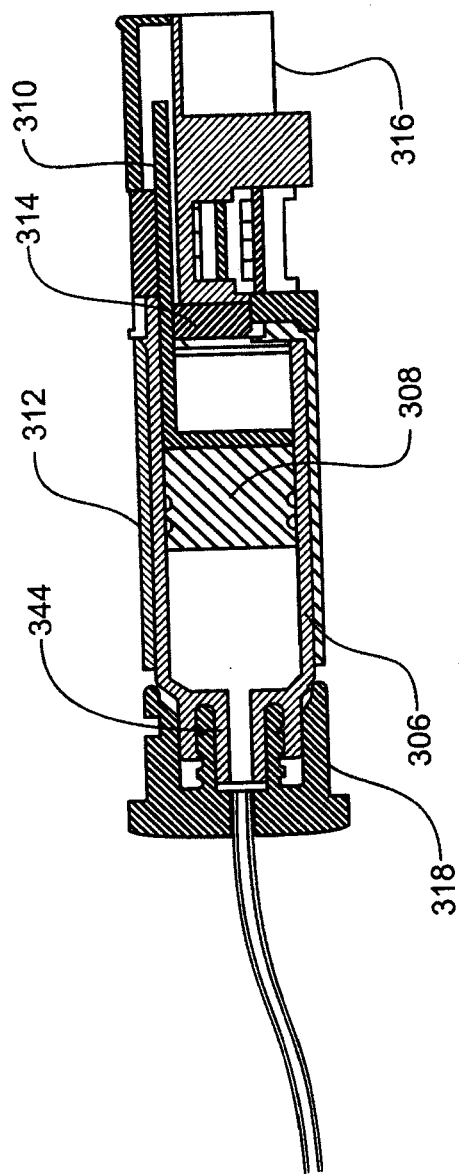
Figure 3K:
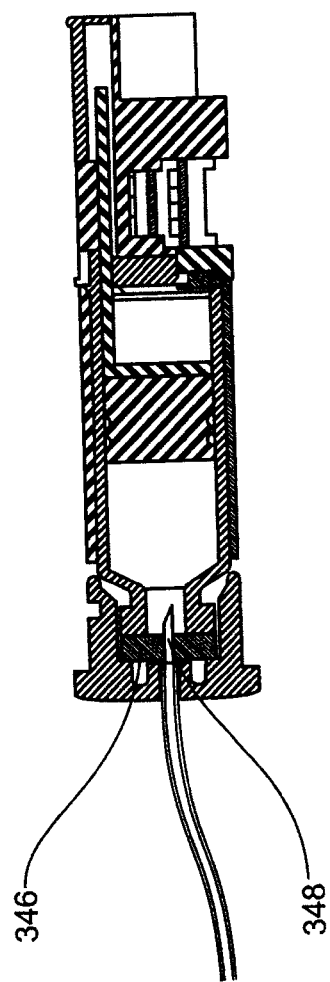
Figure 3L:
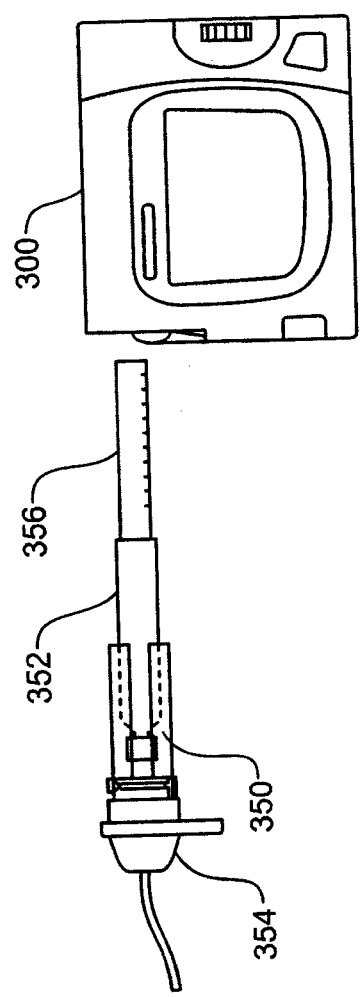
Figure 4A:
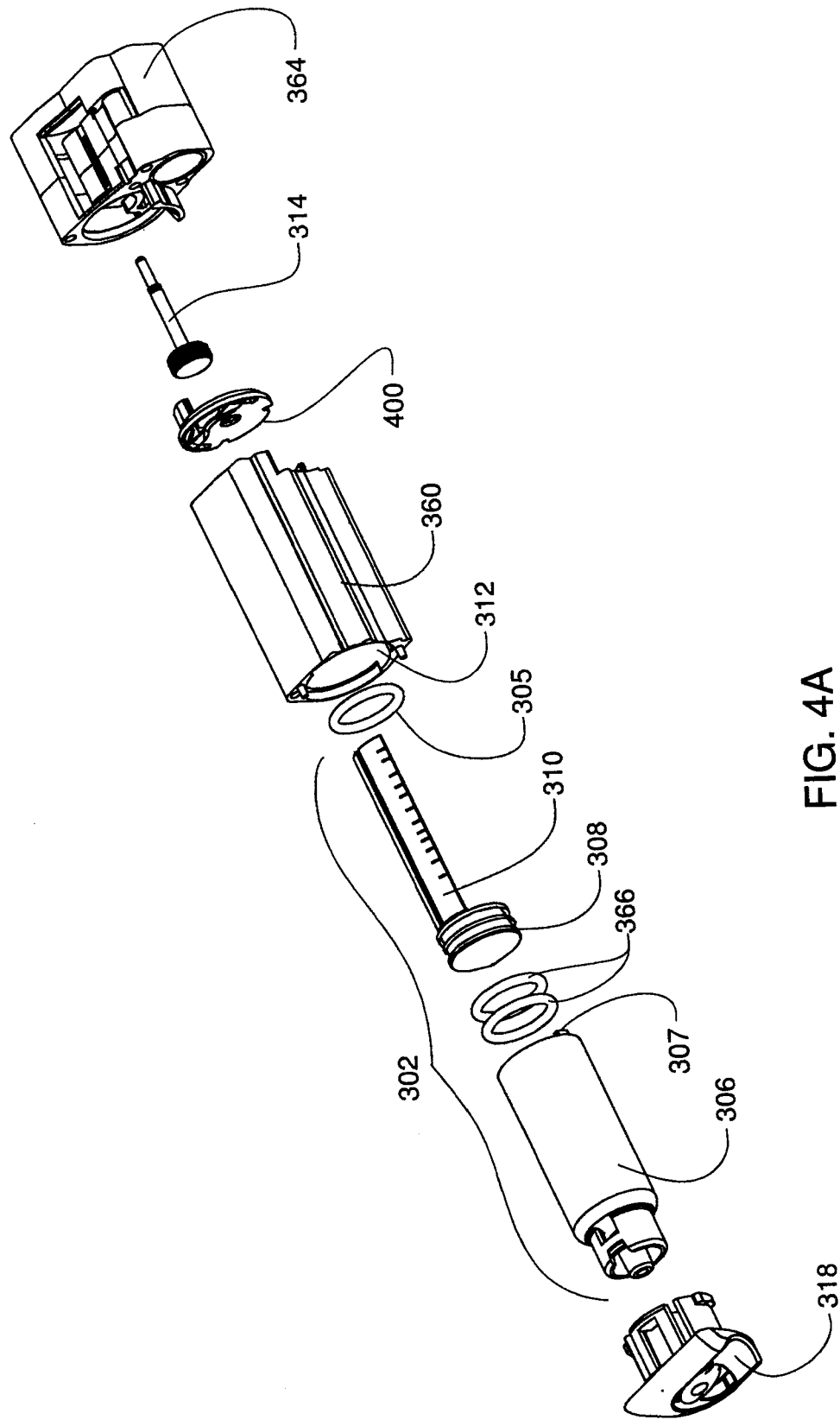
Figure 4B:
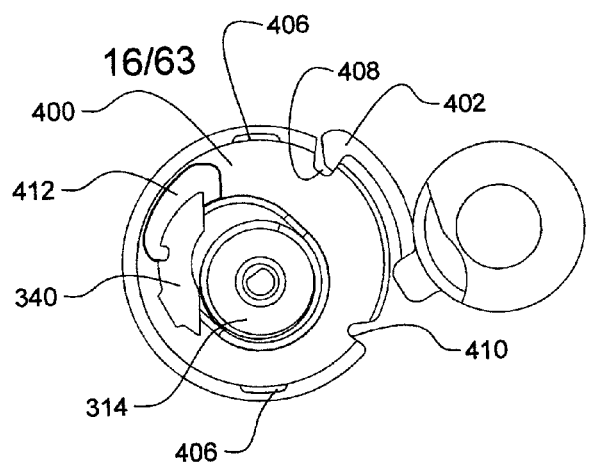
Figure 4C:
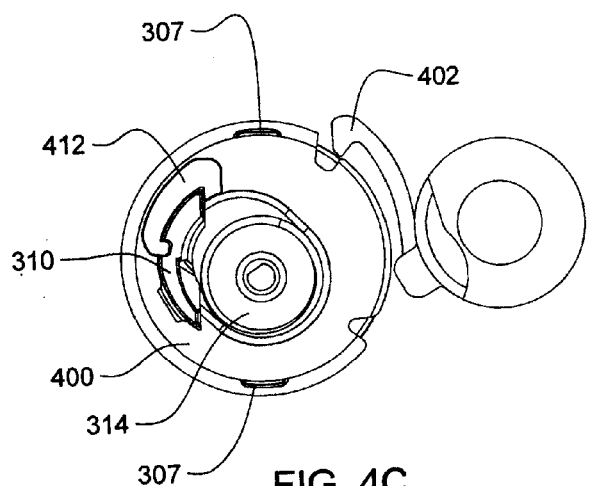
Figure 4D:
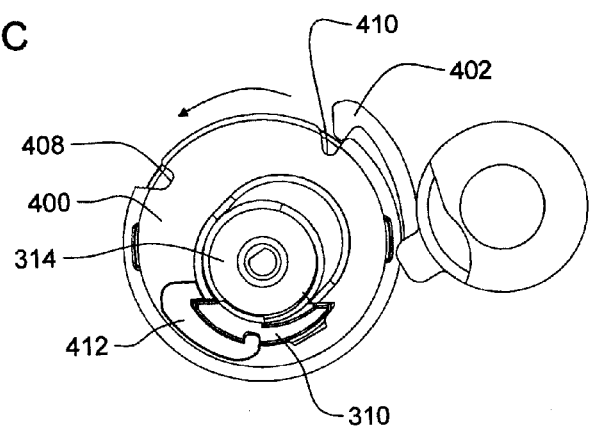
Figure 4J:
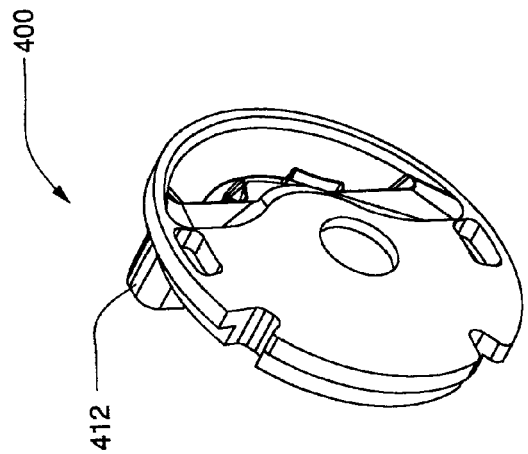
Figure 4K:
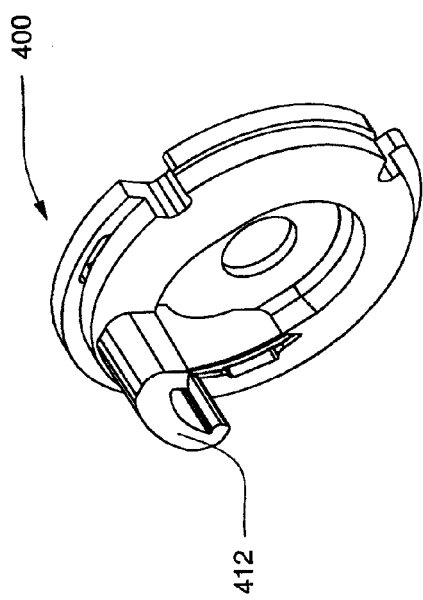
Figure 4L:
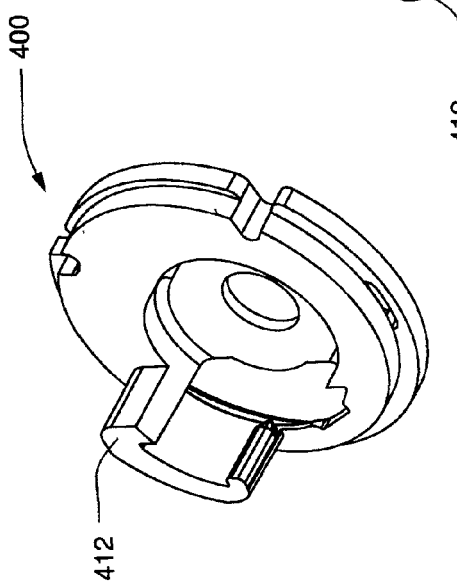
Figure 4M:
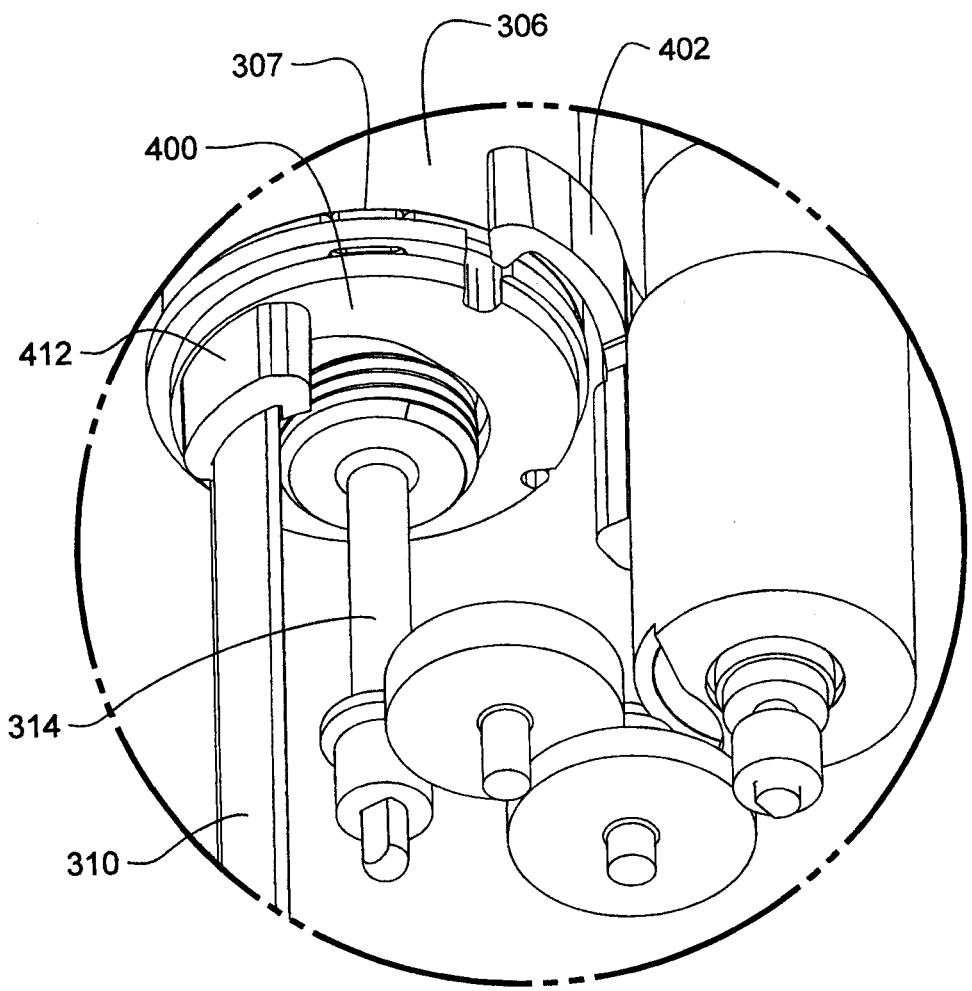
Figure 4N:
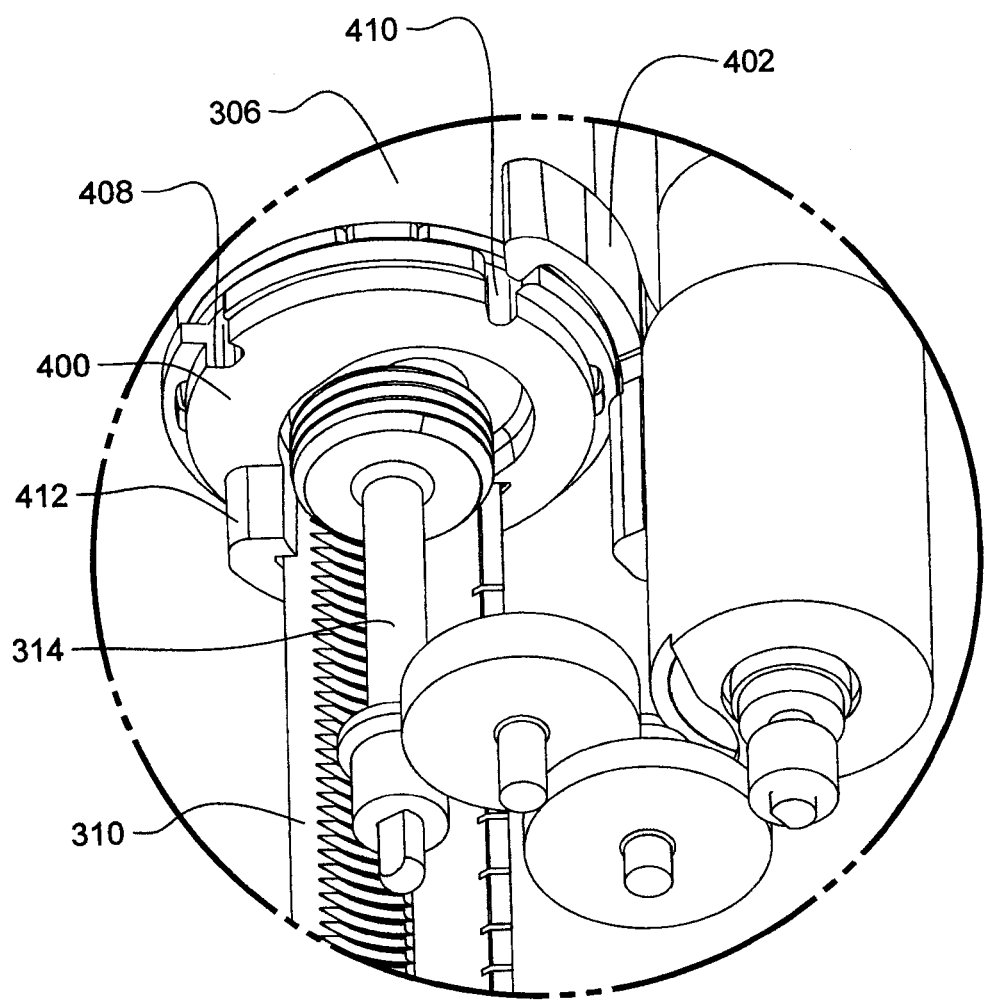
Figure 5A:
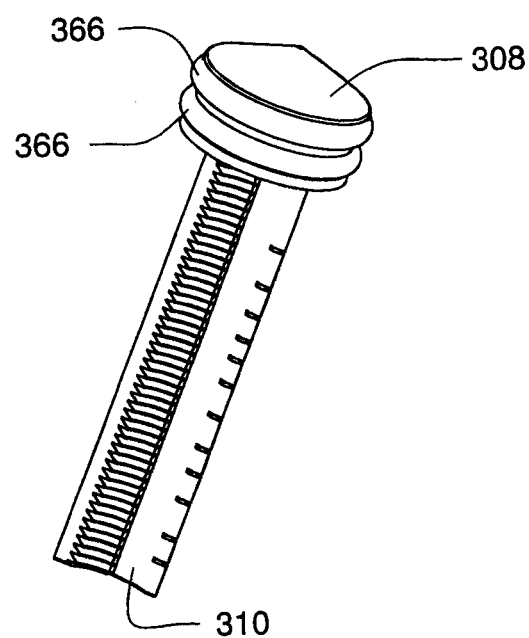
Figure 5B:
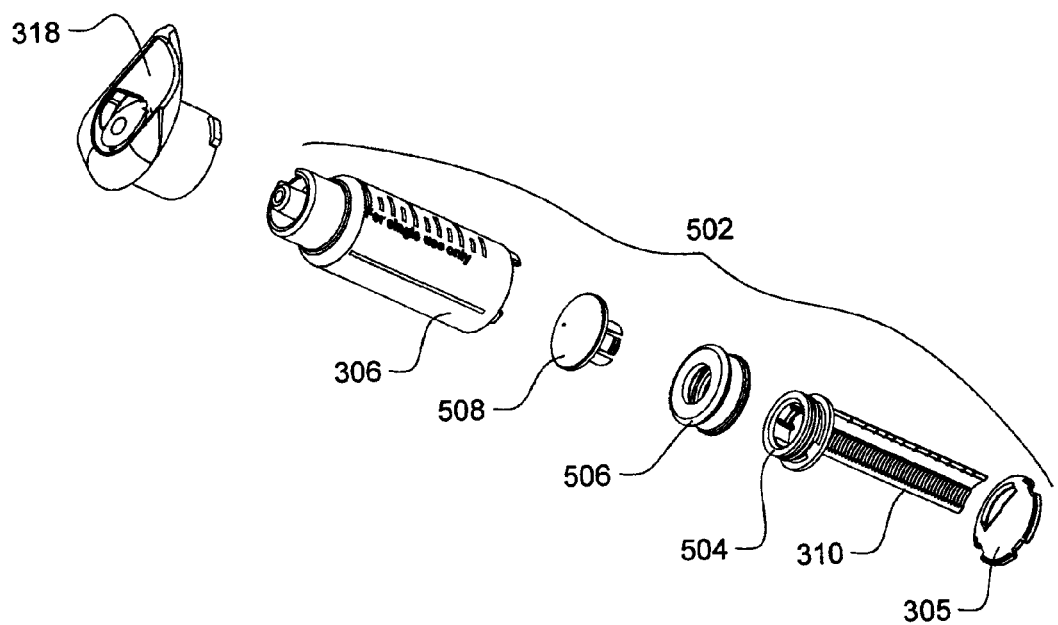
Figure 5C:
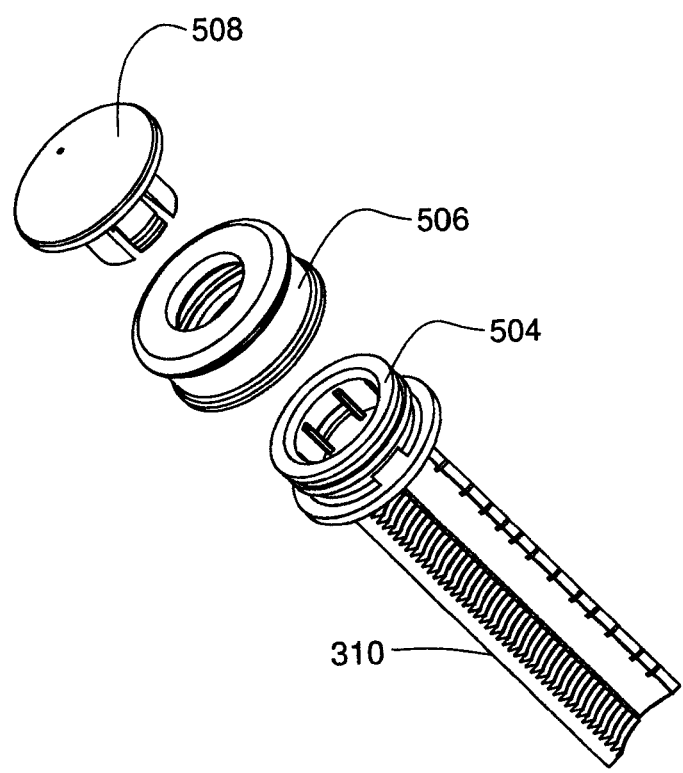
Figure 5D:
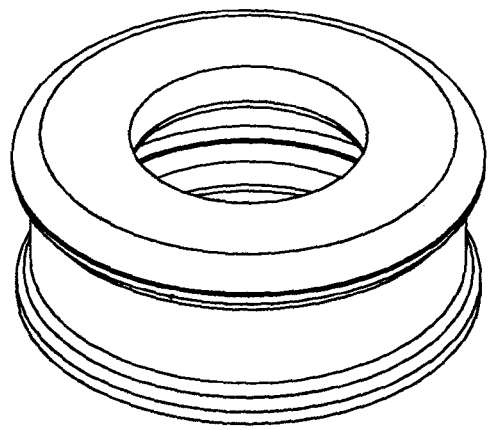
Figure 5E:
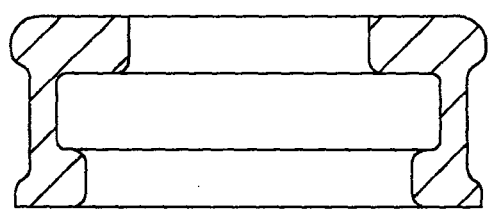
Figure 5F:
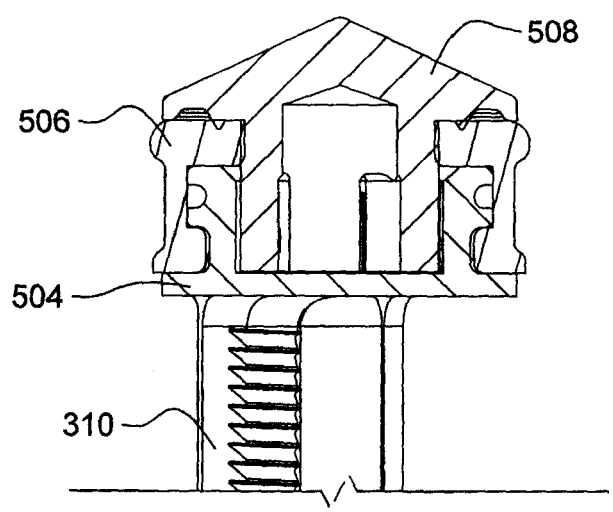
Figure 5G:
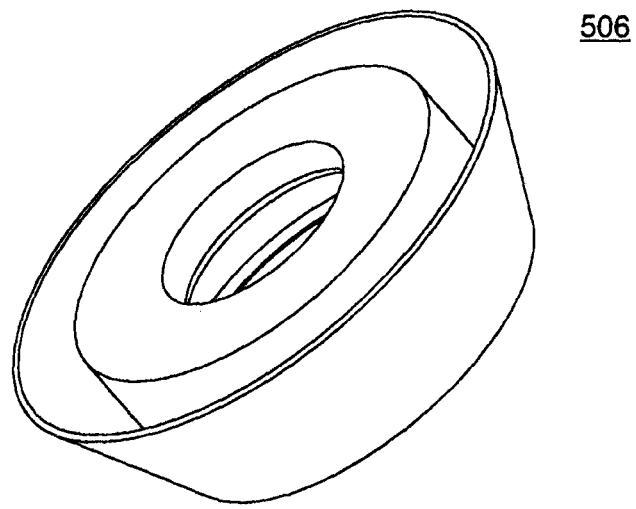
Figure 5H:
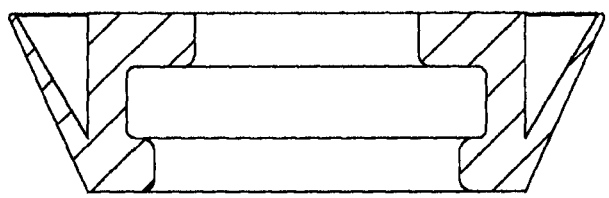
Figure 5I:
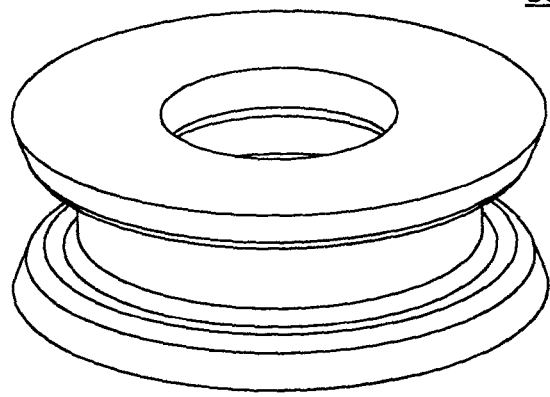
Figure 5J:
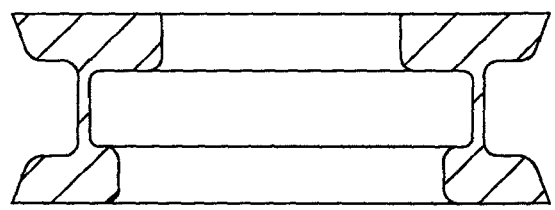
Figure 5K:
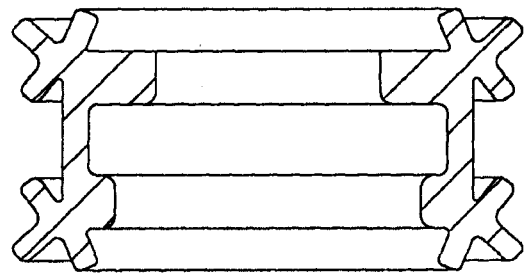
Figure 5L:
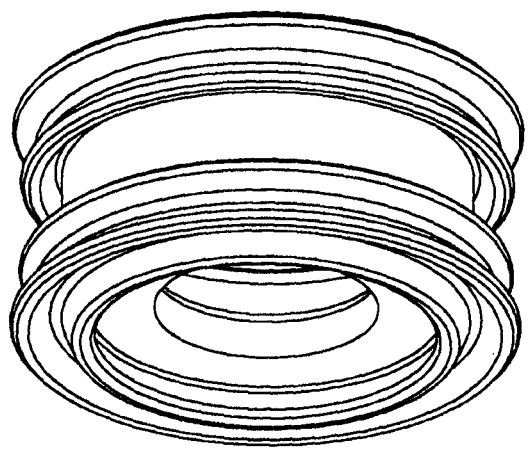
Figure 5M:
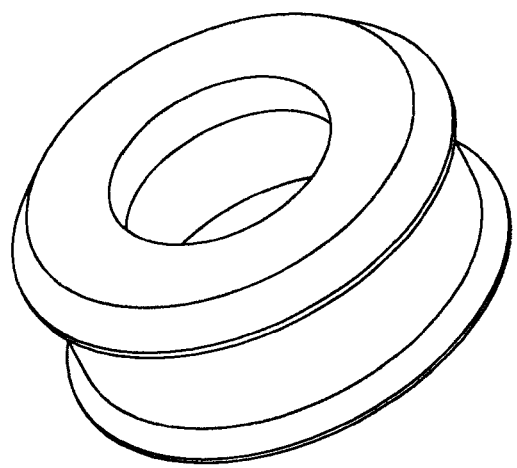
Figure 5N:
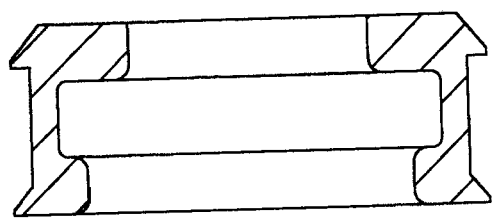
Figure 5O:
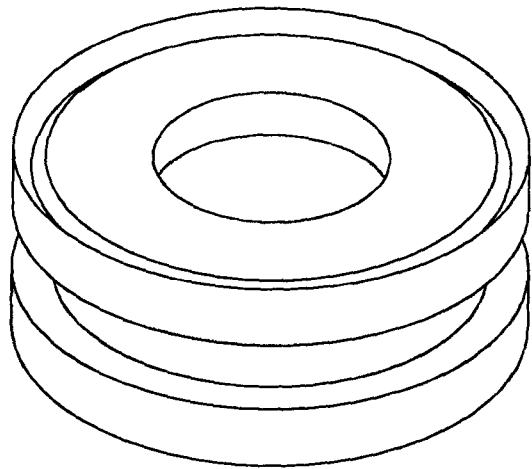
Figure 5P:
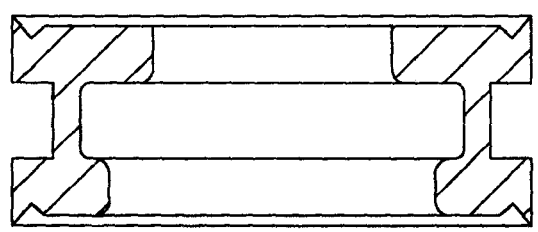
Figure 6A:
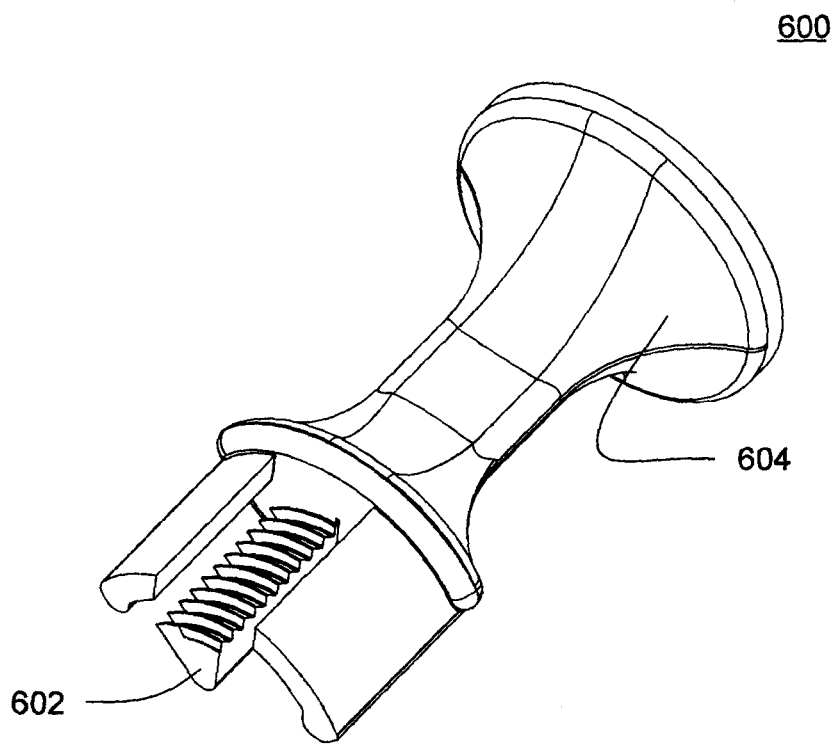
Figure 6B:
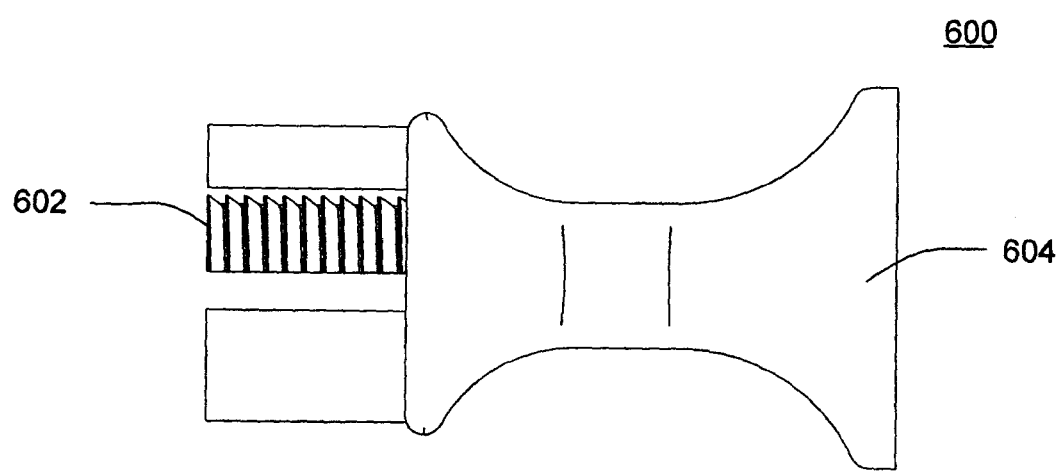
Figure 6C:
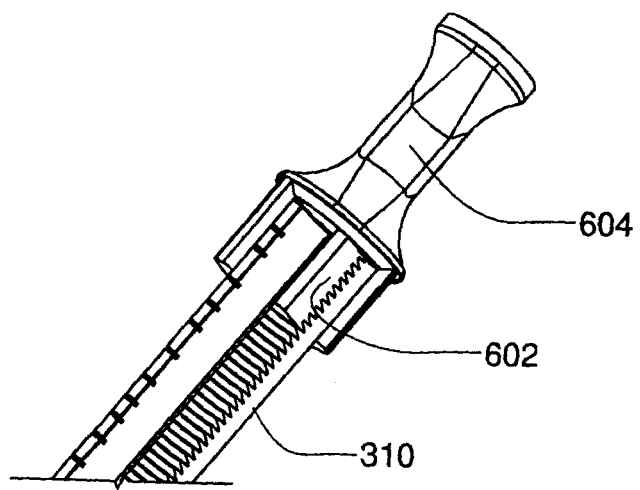
Figure 6D:
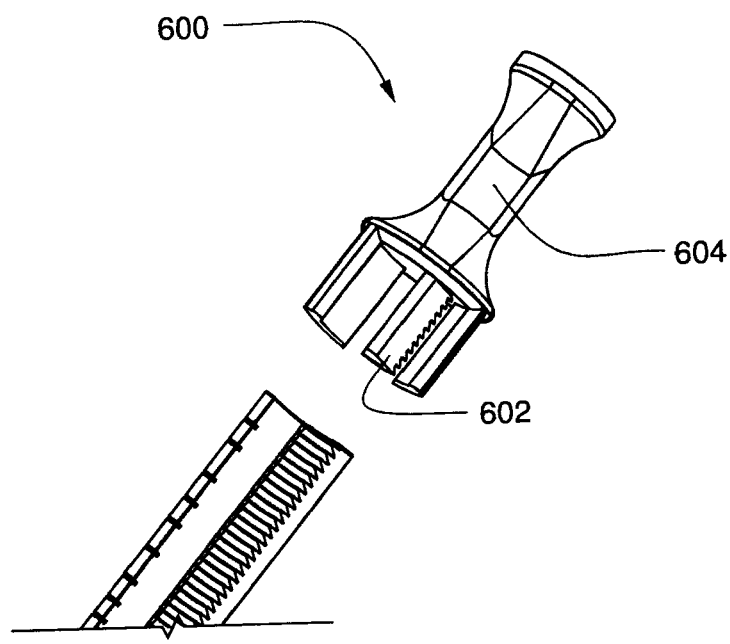
Figure 6E:
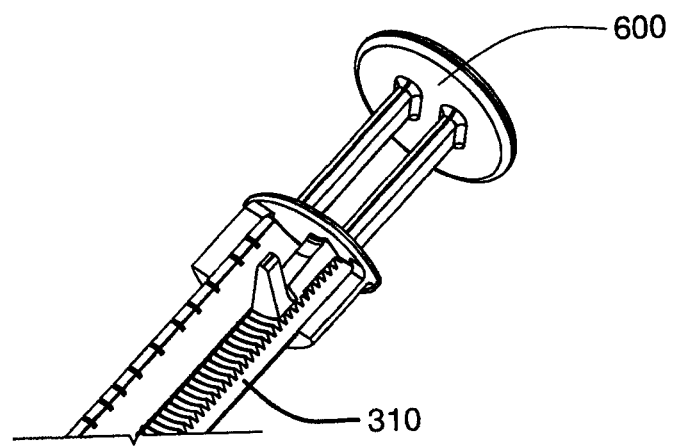
Figure 6F:
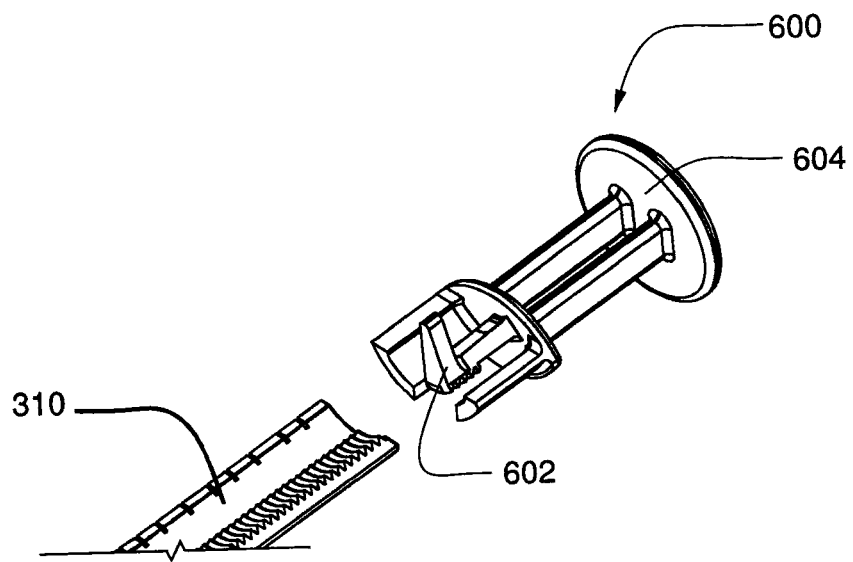
Figure 6G:
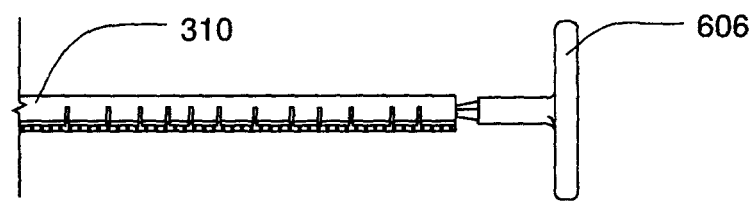
Figure 6H:
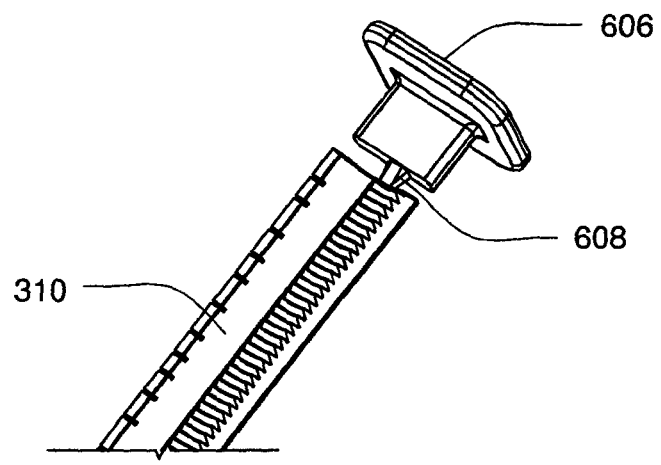
Figure 6I:
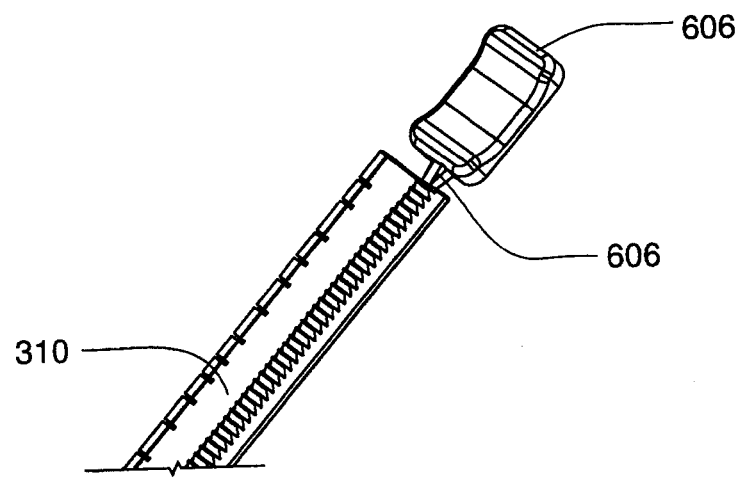
Figure 7A:
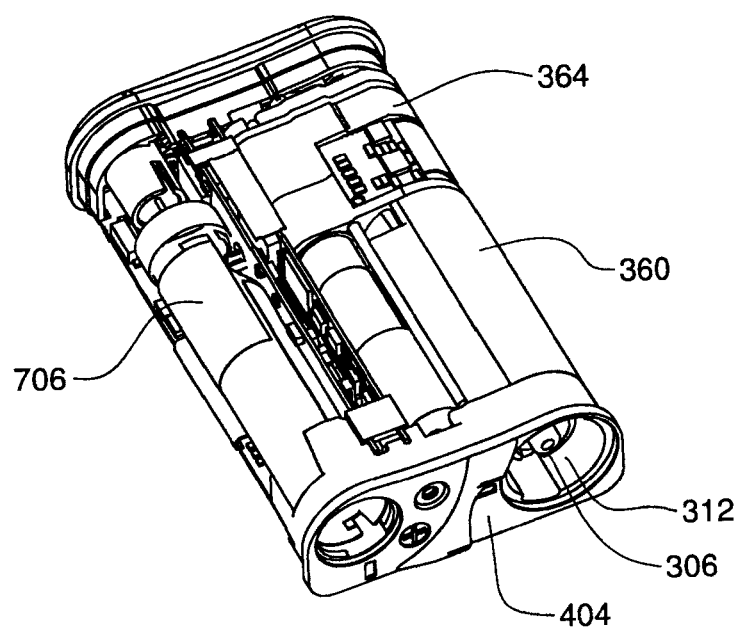
Figure 7B:
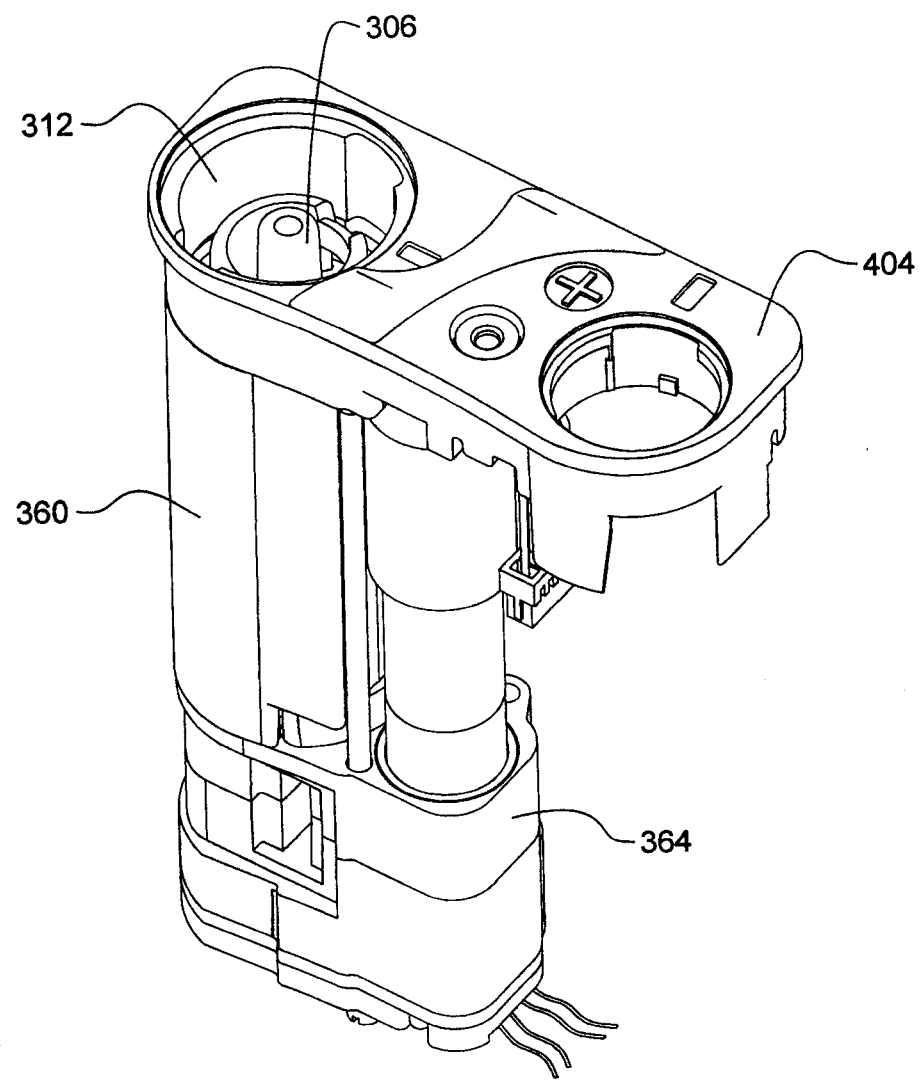
Figure 7C:
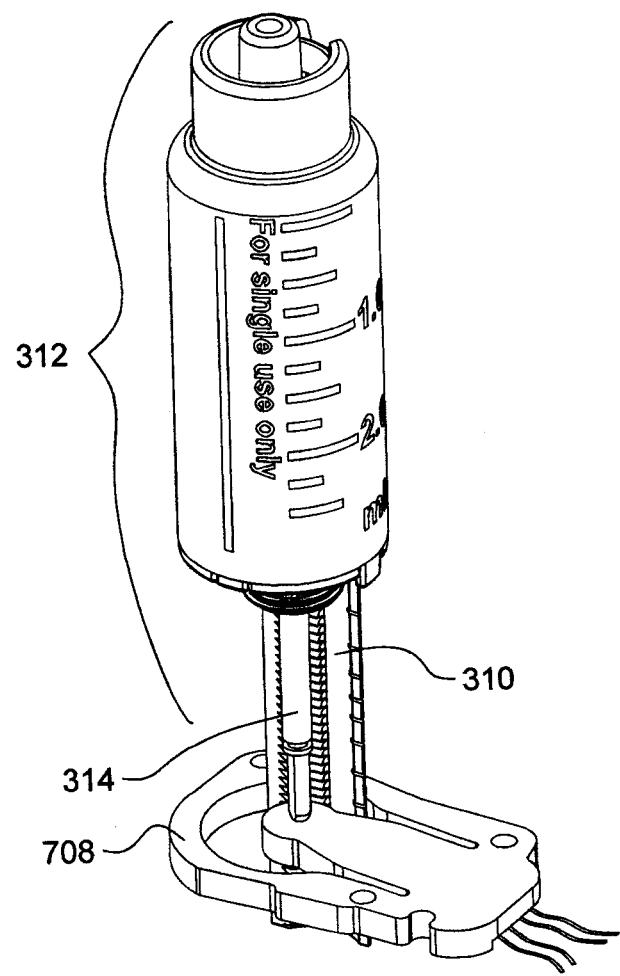
Figure 7D:
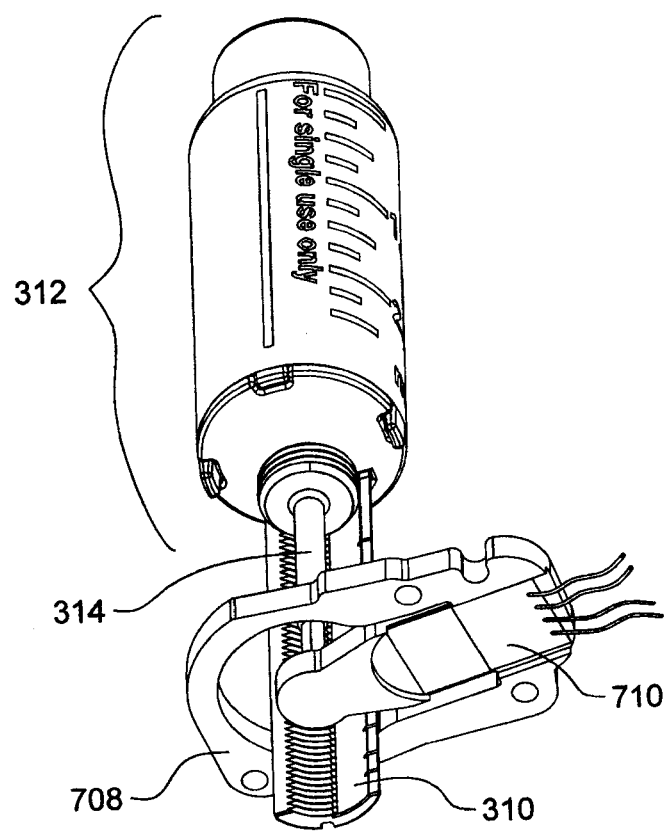
Figure 7E:
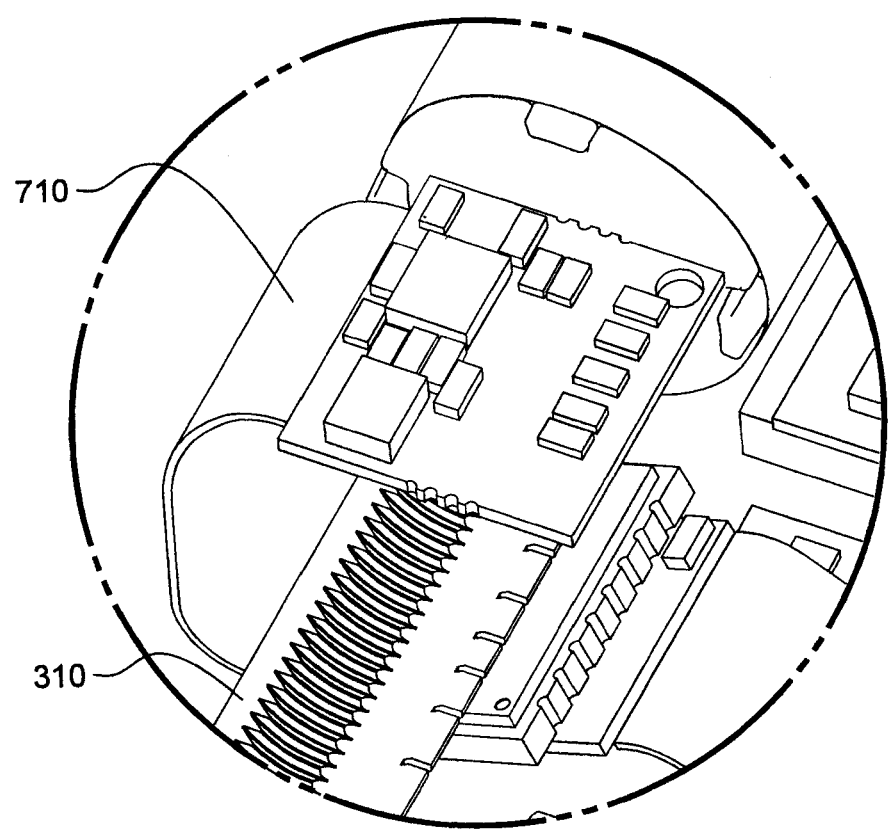
Figure 9C:
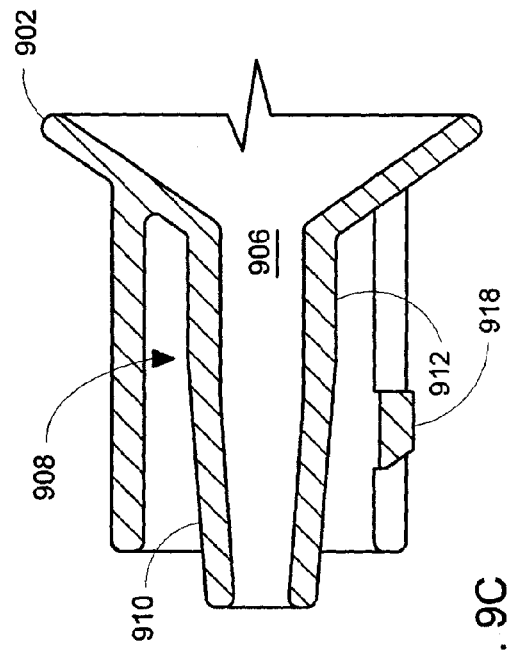
Figure 9C:
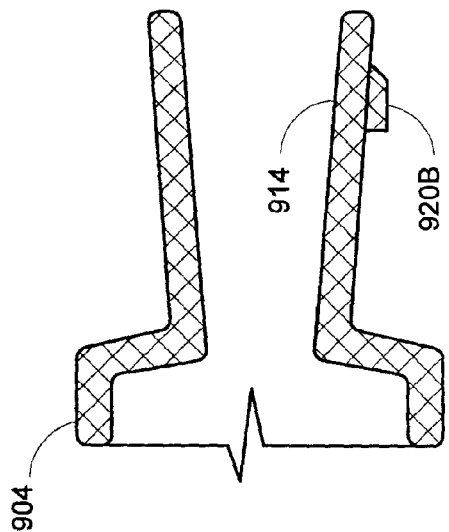
Figure 9D:
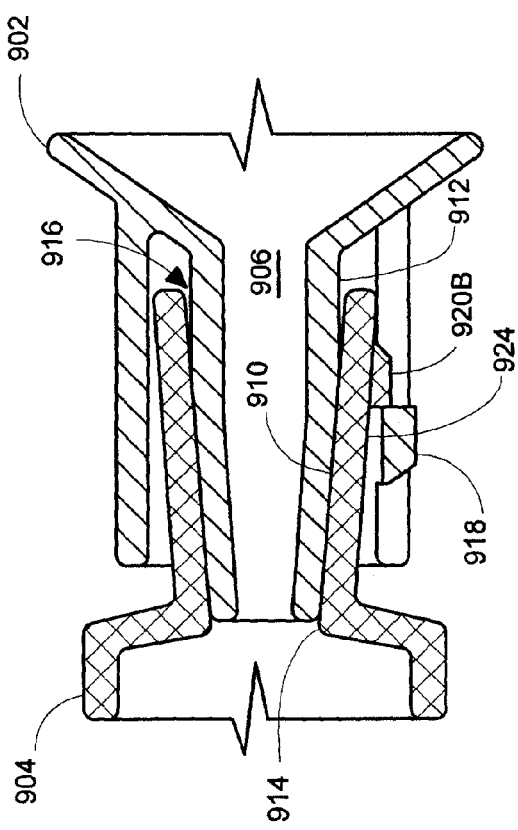
Figure 11:
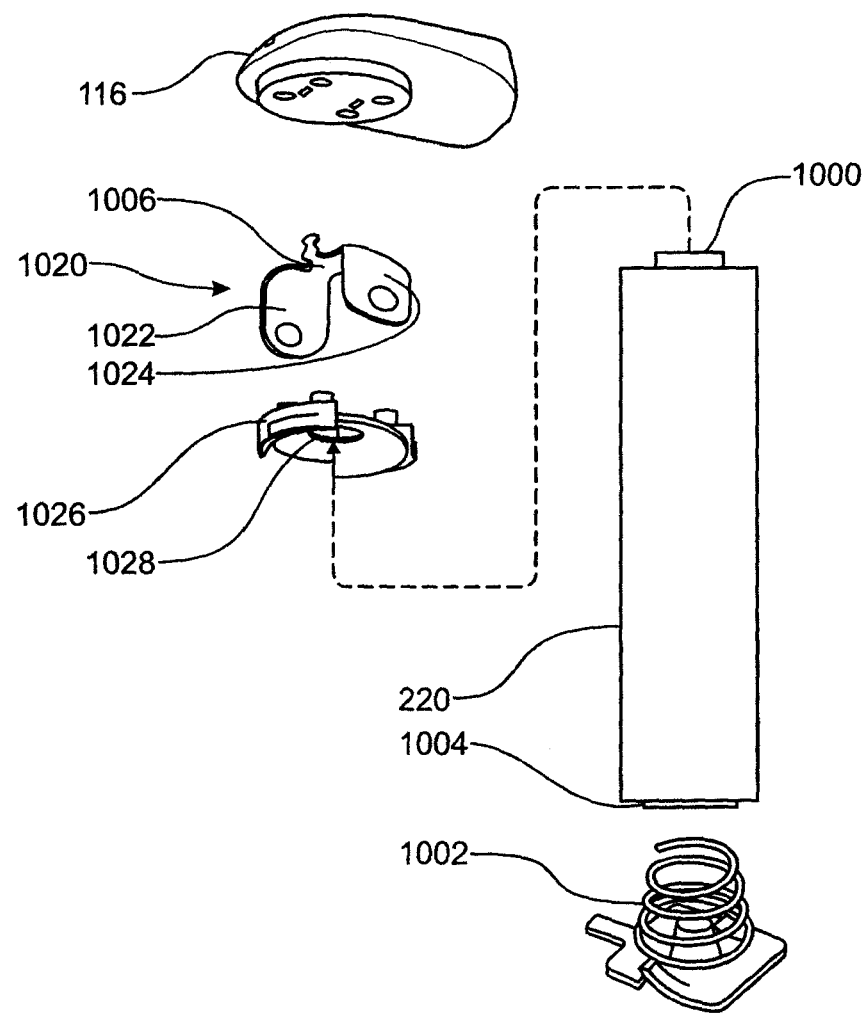
Figure 13:
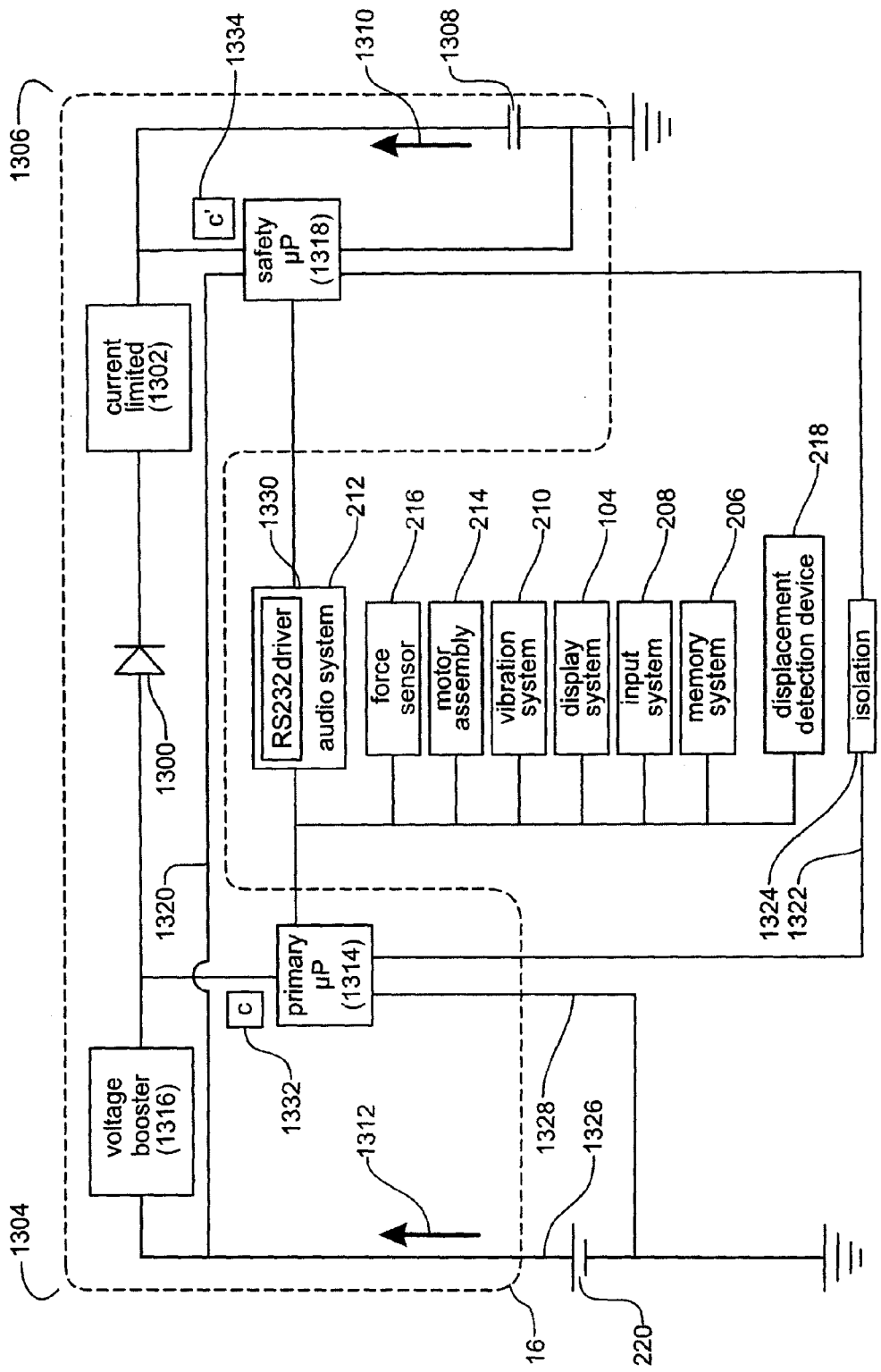
Figure 14:
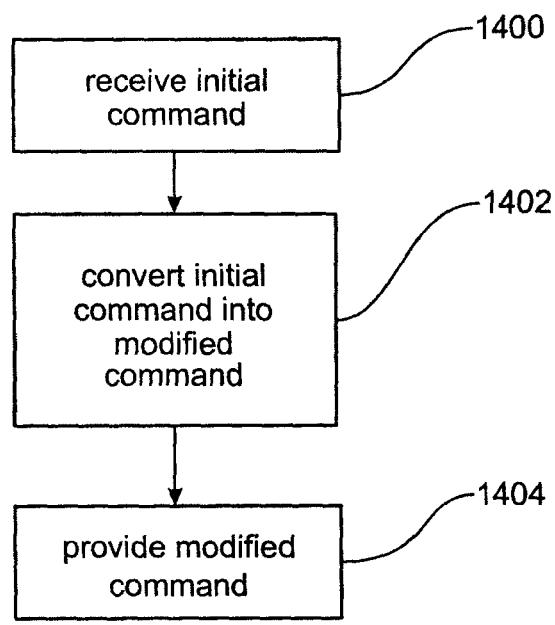
Figure 15:
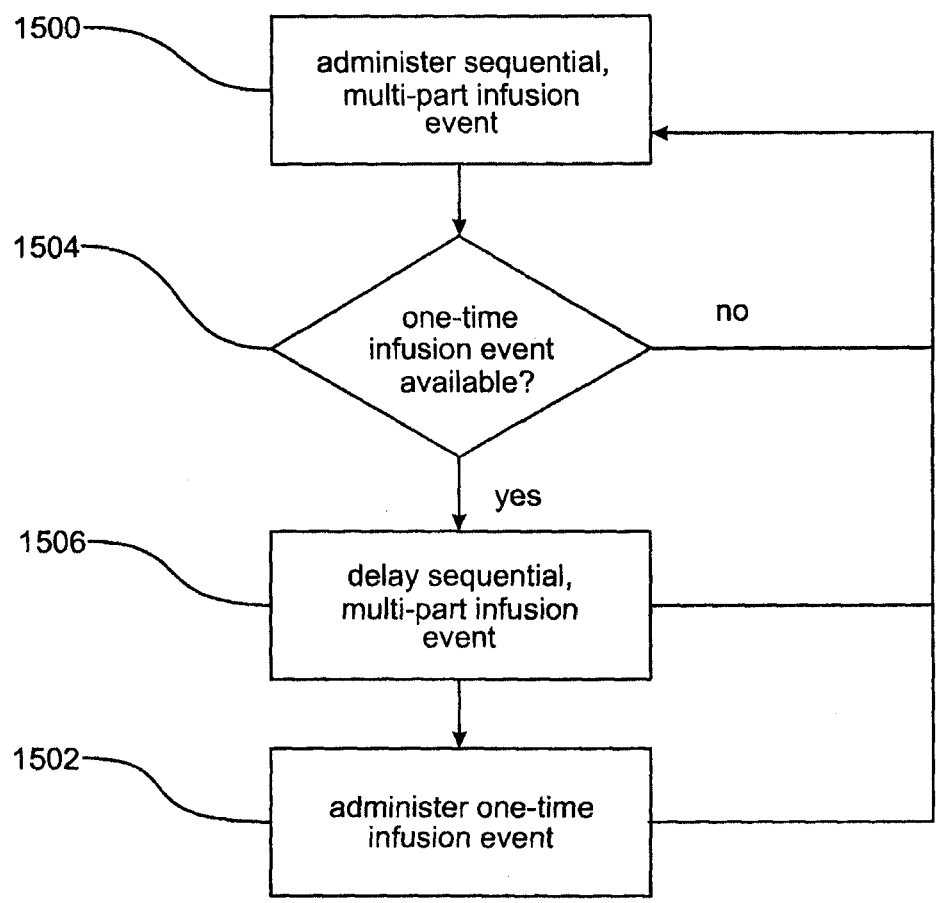
Figure 16:
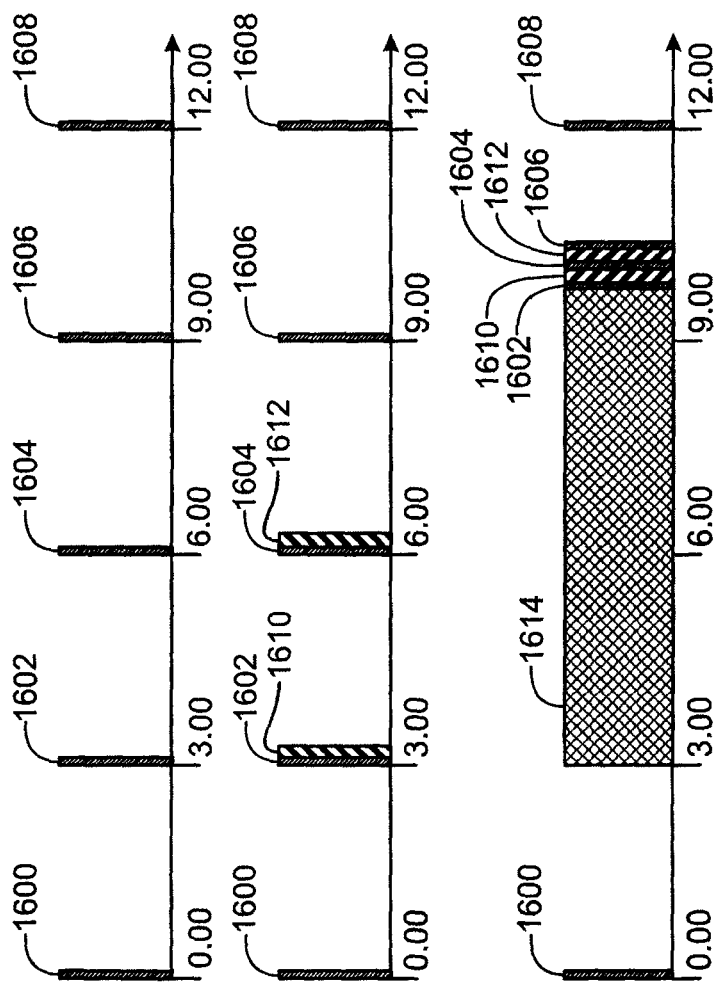
Figure 17:
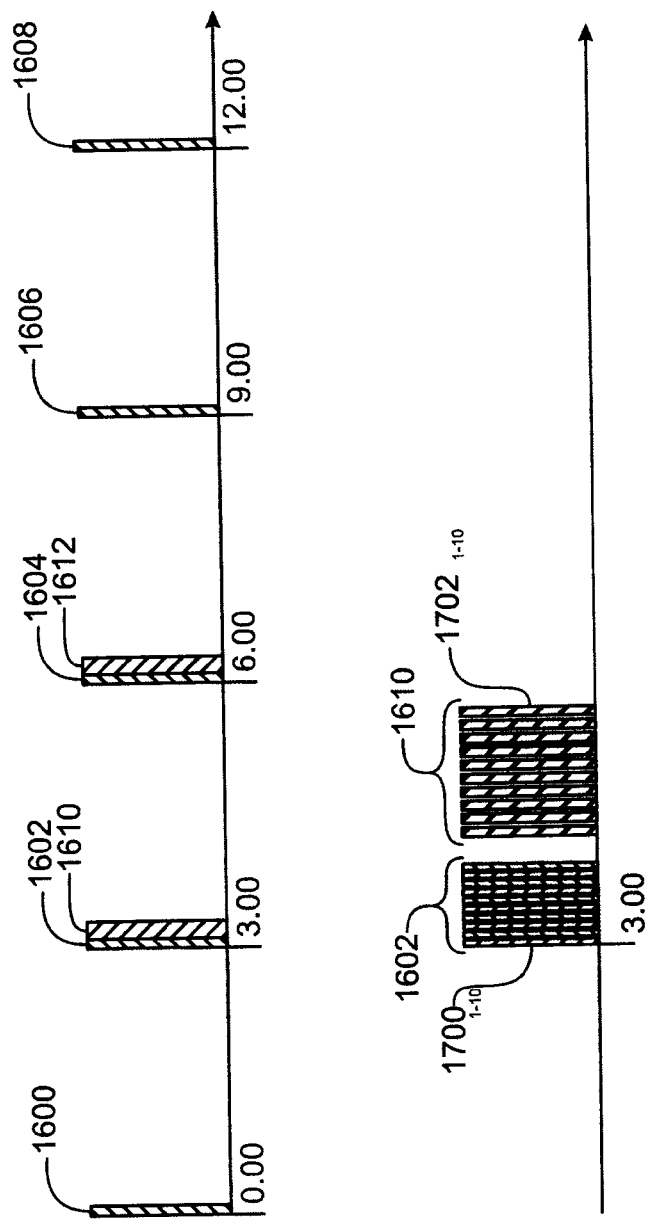

FIG. IF is a front isometric view of the infusion pump assembly of FIG. 1;

FIG. 2 is a diagrammatic view of the infusion pump assembly of FIG. 1;

FIG. 3A is a top-level view of an infusion pump according to one embodiment;

FIG. 3B is an exploded view of a drive mechanism for the infusion pump of FIG. 3A;

FIG. 3C is an isometric views of one embodiment of a reservoir and locking hub assembly according to one embodiment;

FIG. 3D is an exploded isometric view of a locking hub and a reservoir according to one embodiment;

FIG. 3E is an isometric view of one embodiment of the reservoir assembly;

FIG. 3F shows an embodiment of a pump barrel locking mechanism;

FIG. 3G shows a magnified view according to FIG. 3F;

FIGS. 3H-3I shows the relation of the drive screw to the plunger rod for the infusion pump of FIG. 3A;

FIG. 3J shows a connection from one embodiment of a reservoir to a tubing set;

FIG. 3K illustrates another method of connecting one embodiment of a reservoir to a tubing set;

FIG. 3L shows an adapter for using a small diameter reservoir with the pump assembly according to one embodiment;

FIGS. 3M-N are on-axis views of the adapter of FIG. 3L;

FIG. 4A is an exploded view of one embodiment of the reservoir and locking hub assembly with portions of the loading and drive assembly of one embodiment of the infusion pump assembly;

FIGS. 4B-4D are partial views of the loading of the reservoir assembly onto the drive assembly;

FIGS. 4E-4F are top and bottom views of the hub and battery end cap according to one embodiment of the infusion pump apparatus;

FIG. 4G-4I are bottom, side and top views, respectively, of one embodiment of the locking disc;

FIGS. 4J-4L are isometric views of one embodiment of the locking disc;

FIGS. 4M-4N are partial illustrative views of the loading of the reservoir assembly onto the drive assembly of one embodiment of the infusion pump apparatus;

FIG. 5A is an isometric view of one embodiment of the plunger and plunger rod apparatus;

FIG. 5B is an isometric view of one embodiments of the reservoir and locking hub assembly;

FIG. 5C is an isometric view of the plunger and plunger rod apparatus according to the reservoir and locking hub assembly shown in FIG. 5B;

FIGS. 5D-5E are isometric and cross sectional views, respectively, of the plunger seal apparatus according to one embodiment;

FIG. 5F is a cross sectional cut-off view of the assembled plunger apparatus of FIG. 5C;

FIG. 5G-5P are various embodiments of the plunger seal apparatus;

FIGS. 6A-6B are views of one embodiment of the filling aid apparatus;

FIGS. 6C-6D are isometric views of the filling aid apparatus of FIGS. 6A-6B together with a plunger rod, both attached to the plunger rod and detached from the plunger rod, respectively;

FIGS. 6E-6F are isometric views of one embodiment of the filling aid apparatus together with a plunger rod, both attached to the plunger rod and detached from the plunger rod, respectively;

FIGS. 6G-6I are isometric views of alternate embodiments of the filling aid together with a plunger rod;

FIGS. 7A-7B are isometric views of various portions of one embodiment of the infusion pump assembly;

FIGS. 7C-7D are isometric views of the reservoir assembly together with the drive screw and the strain gauge according to one embodiment of the infusion pump apparatus;

FIG. 7E is an magnified isometric view of a plunger rod together with an optical displacement sensor according to one embodiment of the infusion pump apparatus;

FIGS. 8A-8D are various alternate embodiments of the reservoir assembly;

FIGS. 9A-9B are cross-sectional views of a medium connector assembly included within the infusion pump assembly of FIG. 1;

FIGS. 9C-9D are cross-sectional views of a medium connector assembly included within the infusion pump assembly of FIG. 1;

FIGS. 9E-9F are cross-sectional views of a medium connector assembly included within the infusion pump assembly of FIG. 1;

FIGS. 9G-H are cross-sectional views of a medium connector assembly included within the infusion pump assembly of FIG. 1;

FIGS. 9I-J are cross-sectional views of a medium connector assembly included within the infusion pump assembly of FIG. 1;

FIG. 10A is an isometric view of a removable cover assembly for use with the infusion pump assembly of FIG. 1;

FIG. 10B is an alternative isometric view of the removable cover assembly of FIG. 10A;

FIG. IOC is a cross-sectional view of the removable cover assembly of FIG. 10A;

FIG. 11 is an alternative isometric view of the removable cover assembly of FIG. 10A;

FIG. 12A-12D are isometric views of an alternative embodiment of the removable cover assembly of FIG. 4;

FIG. 13 is a diagrammatic view of the infusion pump assembly of FIG. 1;

FIG. 14 is a flowchart of a process executed by the infusion pump assembly of FIG. 1;

FIG. 15 is a flowchart of a process executed by the infusion pump assembly of FIG. 1;

FIG. 16 is a timeline illustrative of a plurality of discrete infusion events;

FIG. 17 is a more detailed view of two discrete infusion events included within FIG. 16.

Figure 19:
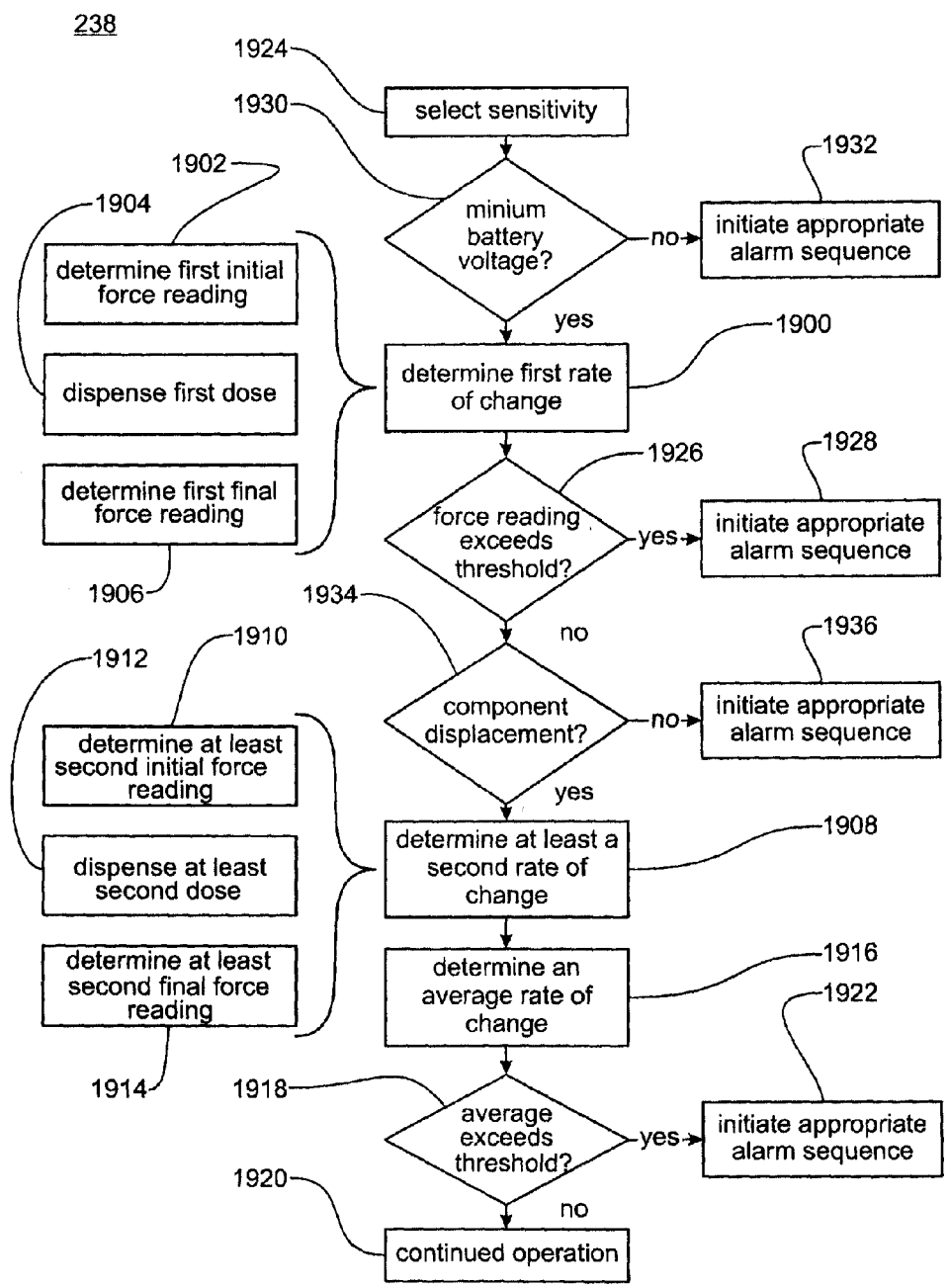
Figure 20:
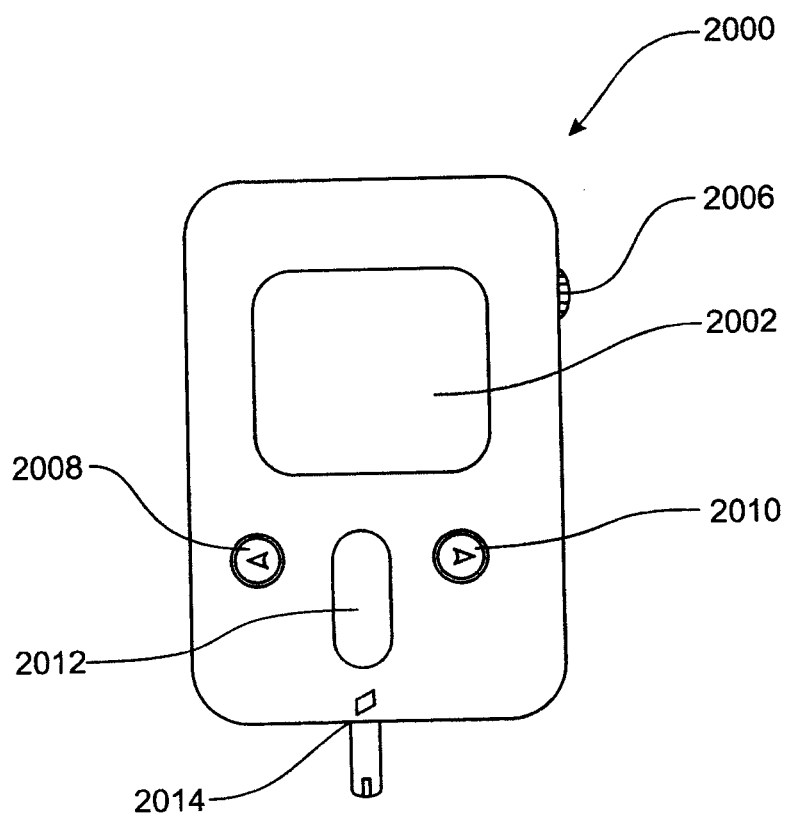

FIG. 18 is a diagrammatic view of a storage array included within the infusion pump assembly of FIG. 1;

FIG. 19 is a flowchart of a process executed by the infusion pump assembly of FIG. 1; and FIG. 20 is an illustrative view of one embodiment of a remote control assembly.

Like reference symbols in the various drawings indicate like elements.

DETAILED DESCRIPTION OF THE PREFERRED EMBODIMENTS

Referring to FIGS. 1A-1F, there is shown an infusion pump assembly 100 that may be housed within enclosure assembly 102. Infusion pump assembly 100 may include display system 104 that may be visible through enclosure assembly 102. One or more switch assemblies/input devices 106, 108, 110 may be positioned about various portions of enclosure assembly 102. Enclosure assembly 102 may include infusion port assembly 112 to which cannula assembly 114 may be releasably coupled. Removable cover assembly 116 may allow access to power supply cavity 118 (shown in phantom on FIG. 2).

Referring to FIG. 2, there is shown a diagrammatic view of infusion pump assembly 100. Infusion pump assembly 100 may be configured to deliver infusible fluid 200 to user 202. Infusible fluid 200 may be delivered intravenously (i.e., into a vein), subcutaneously (i.e., into the skin), arterially (i.e., into an artery), and epidurally (i.e., into the epidural space). Examples of infusible fluid 200 may include but are not limited to insulin, nutrients, saline solution, antibiotics, analgesics, anesthetics, hormones, vasoactive drugs, and chelation drugs, and any other therapeutic fluids Infusion pump assembly 100 may include processing logic 204 that executes one or more processes that may be required for infusion pump assembly 100 to operate properly. Processing logic 204 may include one or more microprocessors (not shown), one or more input/output controllers (not shown), and cache memory devices (not shown). One or more data buses and/or memory buses may be used to interconnect processing logic 204 with one or more subsystems.

Examples of the subsystems interconnected with processing logic 204 may include but are not limited to memory system 206, input system 208, display system 104, vibration system 210, audio system 212, motor assembly 214, force sensor 216, and displacement detection device 218. Infusion pump assembly 100 may include primary power supply 220 (e.g. a battery) configured to be removable installable within power supply cavity 118 and to provide electrical power to at least a portion of processing logic 204 and one or more of the subsystems (e.g., memory system 206, input system 208, display system 104, vibration system 210, audio system 212, motor assembly 214, force sensor 216, and displacement detection device 218).

Infusion pump assembly 100 may include reservoir assembly 222 configured to contain infusible fluid 200. In some embodiments, reservoir assembly 222 may be a reservoir assembly similar to that described in U.S. Patent Application Publication No. US 2004-0135078-A1, published Jul. 15, 2004, which is herein incorporated by reference in its entirety. In other embodiments, the reservoir assembly may be any assembly in which fluid may be acted upon such that at least a portion of the fluid may flow out of the reservoir assembly, for example, the reservoir assembly, in various embodiments, may include but is not limited to: a barrel with a plunger, a cassette or a container at least partially constructed of a flexible membrane.

Plunger assembly 224 may be configured to displace infusible fluid 200 from reservoir assembly 222 through cannula assembly 114 (which may be coupled to infusion pump assembly 100 via infusion port assembly 112) so that infusible fluid 200 may be delivered to user 202. In this particular embodiment, plunger assembly 224 is shown to be displaceable by partial nut assembly 226, which may engage lead screw assembly 228 that may be rotatable by motor assembly 214 in response to signals received from processing logic 204.

In this particular embodiment, the combination of motor assembly 214, plunger assembly 224, partial nut assembly 226, and lead screw assembly 228 may form a pump assembly that effectuates the dispensing of infusible fluid 200 contained within reservoir assembly 222. An example of partial nut assembly 226 may include but is not limited to a nut assembly that is configured to wrap around lead screw assembly 228 by e.g., 30 degrees. In some embodiments, the pump assembly may be similar to one described in U.S. Pat. No. 7,306,578, issued Dec. 11, 2007, which is herein incorporated by reference in its entirety.

During operation of infusion pump assembly 100, infusible fluid 200 may be delivered to user 202 in accordance with e.g. a defined delivery schedule. For illustrative purposes only, assume that infusion pump assembly 100 is configured to provide 0.00025 mL of infusible fluid 200 to user 202 every three minutes. Accordingly, every three minutes, processing logic 204 may provide the appropriate drive signals to motor assembly 214 to allow motor assembly 30 to rotate lead screw assembly 228 the appropriate amount so that partial nut assembly 226 (and therefore plunger assembly 224) may be displaced the appropriate amount in the direction of arrow 230 so that 0.00025 mL of infusible fluid 200 are provided to user 202 (via cannula 114). It should be understood that the volume of infusible fluid 200 that may be provided to user 202 may vary based upon, at least in part, the nature of the infusible fluid (e.g., the type of fluid, concentration, etc.), use parameters (e.g., treatment type, dosage, etc.). As such the foregoing illustrative example should not be construed as a limitation of the present disclosure.

Force sensor 216 may be configured to provide processing logic 204 with data concerning the force required to drive plunger assembly 224 into reservoir assembly 222. Force sensor 216 may include one or more strain gauges and/or pressure sensing gauges and may be positioned between motor assembly 214 and an immovable object (e.g. bracket assembly 232) included within infusion pump assembly 100.

In one embodiment, force sensor 216 includes four strain gauges (not shown), such that: two of the four strain gauges are configured to be compressed when driving plunger 222 into reservoir assembly 222; and two of the four strain gauges are configured to be stretched when driving plunger 222 into reservoir assembly 222. The four strain gauges (not shown) may be connected to a Wheatstone Bridge (not shown) that produces an analog force signal (not shown) that is a function of the pressure sensed by force sensor 216. The analog force signal (not shown) produced by force sensor 216 may be provided to an analog-to-digital converter (not shown) that may convert the analog force signal (not shown) into a digital force signal (not shown) that may be provided to processing logic 204. An amplifier assembly (not shown) may be positioned prior to the above-described analog-to-digital converter and may be configured to amplify the output of e.g., force sensor 216 to a level sufficient to be processed by the above-described analog-to-digital converter.

Motor assembly 214 may be configured as e.g., a brush-type DC electric motor. Further, motor assembly 214 may include a reduction gear assembly (not shown) that e.g. requires motor assembly 214 to rotate three-thousand revolutions for each revolution of lead screw assembly 228, thus increasing the torque and resolution of motor assembly 214 by a factor of three-thousand.

FIG. 3A is an overall view of an infusion pump according to one embodiment. A pump assembly 300 contains the components needed to cause a reservoir assembly 302 to deliver medication or any liquid to a user. The reservoir assembly 302 may contain enough liquid, e.g., medication, such as, but not limited to, insulin, for several days for a typical user. A tubing set 304, connected to the reservoir assembly 302, includes a cannula (not shown) through which the medication is delivered to the user.

Referring also to FIG. 3B, an exploded view of one embodiment of the drive mechanism of the infusion pump is shown. Reservoir assembly 302 may include reservoir 306, plunger 308 and plunger rod 310. Reservoir 306 may contain the medication for delivery to the user and is of variable interior volume. The interior volume may be the liquid capacity of reservoir 306. Plunger 308, may be inserted into the bottom of the reservoir 306, and may cause the volume of reservoir 306 to change as plunger 308 is displaced along the longitudinal axis of reservoir 306. Plunger rod 310 may be connected to plunger 308 with the plunger rod's longitudinal axis displaced from and parallel to the longitudinal axis of reservoir 306. Plunger rod 310 may be threaded for at least a portion of plunger rod's 310 length. As shown in this embodiment, cylindrical pump barrel 312 receives reservoir assembly 302. Pump barrel 312 may constrain plunger rod 310, orienting plunger rod 310 along the longitudinal axis of pump barrel 312. Pump barrel 312 may be contained in pump assembly 300 and, in some embodiments, may contain locking tab 317, which may prevent rotation of pump barrel 312 with respect to pump assembly 300. Gear box 316 in pump assembly 300 may include drive screw 314 along with motor and gears to turn drive screw 314. Drive screw 314 may be threaded and the screw's longitudinal axis may be aligned parallel to and may be displaced from the longitudinal axis of pump barrel 312. Locking hub 318 may be attached to the top of reservoir 306.

Referring now to FIGS. 3C-3D, one embodiment of reservoir assembly 302 together with locking hub 318 is shown. Reservoir 306 may be sized to accommodate any volume desired. In the exemplary embodiment, reservoir 306 may accommodate a volume of 2.5 ml, however, in various other embodiments, reservoir 306 may be sized to accommodate a smaller or larger volume. As discussed above, reservoir 306 volume may change as the plunger is displaced along the longitudinal axis of reservoir 306. In the exemplary embodiments, locking hub 318 may be connected to tubing set (not shown, an embodiment of the tubing set is shown in FIG. 3A as 304) such that the liquid in the reservoir may flow through the locking hub to the tubing. In some embodiments, such as the exemplary embodiment shown, reservoir 306 may also include reservoir alignment tabs 307 and reservoir bottom 305.

Still referring to FIGS. 3C-3D, plunger rod 310, in the exemplary embodiment, may include a threaded portion 320 and a notched portion 322. The threaded portion may thread to drive screw 314. Notched portion 322 may be used, in the exemplary embodiment, to encode information relating to reservoir assembly 302, including but not limited to the information, the methods and devices described in U.S. Patent Application Publication US 2004/0135078 A1, published on Jul. 15, 2004 and entitled Optical Displacement Sensor for Infusion Devices, which is herein incorporated by reference in its entirety.

Referring also to FIG. 3D, the exemplary embodiment of locking hub 310 and mating male portion 324 of reservoir 306 are shown. Reservoir 306 is shown without reservoir bottom 305, which is shown in FIG. 3C. The tapered luer connection is described in more detail below. As shown in FIG. 3D, locking hub 310 may include a female part 329 as well as tab 326, while reservoir 306 may include a male part 324 as well as slot 328. Male part 324 and female part 329 may mate to form a luer connection. Tab 326 and slot 328 may lock together when mated and turned, one part relative to its mating part, such that tab 326 may slide into the slot 328.

Referring now to FIG. 3E, another embodiment of reservoir assembly 330 is shown. In this embodiment, hub portion 332 and reservoir portion 334 are connected, and in one embodiment, are molded as a single part.

Referring also to FIG. 3F, a pump barrel locking mechanism for an embodiment of the device is shown. The pump barrel 312 includes a clearance hole (not shown, shown in FIG. 3H as 340) that guides the plunger rod 310 during insertion of the reservoir assembly 302 into the pump barrel 312. To ensure that the drive screw 314 does not interfere with the plunger rod 310 during insertion of the reservoir assembly 302, the pump barrel 312 maintains a fixed position relative to the pump assembly 300. The position of the pump barrel 312 relative to the pump assembly 300 may be maintained, for example, by a locking tab 317 included in the pump barrel 312 that engages a pump barrel stop 342 in the pump assembly 300. The locking hub 318 may include a flange 338 which dislodges the locking tab 340 from the pump barrel stop 342 when the locking hub 318 turns, allowing the locking hub 318 to rotate the pump barrel 312.

Referring also to FIGS. 3G-3H, these FIGS show views along the longitudinal axis of the pump barrel 312 showing the relation of the drive screw 314 to the plunger rod in a loading position and in an engaged position, respectively. The reservoir assembly 302 is positioned for loading so that the plunger rod 310 does not contact the drive screw 314, as shown in FIG. 3G. With the pump barrel 312 positioned appropriately with respect to the pump assembly 300, the plunger rod 310 clearance from the drive screw 314 is determined by the placement of the clearance hole 340 in the pump barrel 312 base, which hole 340 receives and guides the plunger rod 310. The clearance hole 340 may be tapered to ease insertion of the plunger rod 310. The drive screw 314 fits in a clearance hole 340 in the pump barrel 312. Once the reservoir assembly 302 is inserted into the pump assembly 300, the pump barrel 312 is rotated by the locking hub 318, causing the plunger rod 310 to turn and to engage the drive screw 314, as shown in FIG. 3H. This embodiment advantageously simplifies reservoir loading.

In some embodiments, the plunger rod threads and the drive screw threads are buttress threads. These embodiments may be advantageous in that they eliminate reaction forces on the plunger rod normal to the direction of the rod's longitudinal axis. Such reaction forces may cause the rod to deflect and skip a thread on the drive screw, resulting in under delivery of medication to the user. Buttress threads eliminate the normal component of the reaction force.

Referring also to FIG. 3I, in some embodiments, the locking hub 318 may be connected to the reservoir 306 by a tapered luer connection. The reservoir 306 has a male luer taper integrally molded into the reservoir's top 344. Surrounding the male luer is an annulus with an internal female thread. Similarly, the locking hub 318 contains the mating female luer and threaded male connection.

In another embodiment, a needle connection is provided between reservoir 306 and locking hub 318. As shown in FIG. 3J, the reservoir includes a rubber septum 346 that is attached to the reservoir with a crimped metal collar. A needle 348, integral to the hub, pierces the septum and fluid can then flow from the reservoir to the tubing set.

In other embodiments, as shown in FIG. 3K, an adapter 350 is provided to permit a reservoir 352 whose diameter is substantially smaller than the diameter of a pump barrel to be used with the pump assembly 300. The adapter 350 may be a separate component or may be integrated into the locking hub 354. The locking hub 354, in some embodiments, may be one of the embodiments described herein, and sized accordingly. The adapter 350 aligns and offsets the reservoir's 352 axis parallel to the longitudinal axis of the pump barrel so that the plunger rod 356, when rotated, mates with the drive screw (not shown). FIGS. 3L-3M show an on-axis view of the small diameter reservoir 352 when placed in the adapter 350. As will be apparent, the offset provided by the adapter allows the plunger rod 356, when mated with the plunger 308 and reservoir 352, to engage the drive screw 314 in a similar fashion as for the first embodiment, described above.

Referring now to FIG. 4A, another embodiment of the drive mechanism for an infusion pump is shown. As shown in this embodiment, a cylindrical pump barrel 312, shown here inside a pump barrel housing 360, receives the reservoir assembly 302. The pump barrel 312 terminates with a locking disc 400. The pump barrel 312 constrains the plunger rod 310, orienting the plunger rod 310 along the longitudinal axis of the pump barrel 312. The pump barrel 312 is contained in the pump barrel housing 360, which is contained in the pump assembly 300. The locking disc 400, in the exemplary embodiment, contacts a locking tab (shown in FIG. 4B as 402), which is in the pump gear box 364. The locking tab 402 prevents rotation of the locking disc 400 with respect to the pump assembly 300. However, in some embodiments, the locking disc 400 may not include a locking tab 402. A gear box 364 in the pump assembly 300 includes a drive screw 314 along with motor and gears to turn the drive screw 314, and, as discussed above, in some embodiments, a locking tab 402 for locking the locking disc 400. The drive screw 314 is threaded and the screw's longitudinal axis is aligned parallel to and displaced from the longitudinal axis of the pump barrel 312. A locking hub 318 is attached to the top of the reservoir 306.

Still referring to FIG. 4A, in the embodiment shown, the plunger rod 310 is connected to the plunger 308. In the exemplary embodiment, the plunger rod 310 and plunger 308 are a single molded part. O-rings 366 fit over the plunger 308. However, in some embodiments, the O-rings may be molded into the plunger 308.

Referring back to FIGS. 3C-3D, the locking hub 318 additionally includes locking hub alignment tabs 325. As shown in FIG. 3C, once the locking hub 318 and reservoir 306 are mated, the locking hub alignment tabs 325 and the reservoir alignment tabs 307 are aligned with one another. Referring also to FIGS. 4E-4F, the pump assembly 300 includes a hub and battery end cap 404. The hub section of the hub and battery end cap 404 includes complementary opening for the locking hub 318, including the locking hub alignment tabs 325.

Thus, once the reservoir assembly 302 is mated with the locking hub 318, to load the reservoir into the pump barrel 312, the reservoir must be oriented correctly with respect to the locking hub alignment tabs 325 and the complementary opening in the hub and battery end cap 404. The reservoir alignment tabs 307 will thus also be aligned with the locking hub alignment tabs 325.

Referring now also to FIGS. 4G-4L the locking disc 400 is shown. The locking disc 400 includes a clearance hole 340, which, in the exemplary embodiment is tapered for easy insertion, but in some embodiments, is not tapered. Additionally, the reservoir tab openings 406, plunger rod support 412 and first and second locking tab notches 408, 410 are shown. As discussed above, the reservoir alignment tabs 307 are aligned with the locking hub alignment tabs 325. The orientation assured by the hub and battery end cap 404 assures that the plunger rod 310 will be in the correct orientation to fit through the clearance hole 340, the reservoir alignment tabs 307 will mate with the reservoir tab opening 406, and the reservoir bottom 305 displaces the locking tab 402.

In some embodiments, the locking disc 400 may include only a first locking tab notch 408, or, in some embodiments, may not include any locking tab notches. The locking tab notches 408, 410 maintain the orientation of the locking disc 400 for ease of loading the reservoir and locking hub assembly. Also, the second locking tab notch 408 contributes to maintaining the plunger rod 310 and drive screw 314 relationship. Additionally, although the reservoir tab openings 406 are included in the exemplary embodiment of the locking disc 400, some embodiments of the locking disc 400 do not include reservoir tab openings 406. In these embodiments, the reservoir does not include reservoir alignment tabs 307 (shown in FIGS. 3C-3D).

In the exemplary embodiment, the reservoir tab openings 406, together with the reservoir alignment tabs 307, aid in the rotation of the locking disc 400. When loading the reservoir and locking hub assembly into the pump assembly 300, the user, having aligned the reservoir and locking hub assembly with the hub and battery cap 404, drops the reservoir and locking hub assembly into the pump barrel 312 and applies a slight pressure to the locking hub 318. The user then applies torque to the locking hub 318 to complete the loading process. Where the locking disc 400 includes the reservoir tab openings 406 and the reservoir includes the reservoir alignment tabs 307, as in the exemplary embodiment, the torque applied to the locking hub is transmitted from the reservoir alignment tabs 307 to the locking disc 400 rather than from the locking hub 318 to the plunger rod 310. Thus, in the exemplary embodiment, the reservoir alignment tabs 307 together with the reservoir tab openings 406 work together to take up the torque applied to the reservoir and locking hub assembly which contributes to maintaining the integrity of the plunger rod 310 while also ensuring proper engagement of the plunger rod 310 onto the drive screw 314.

Referring also to FIG. 4B, bottom view of the locking disc 400 is shown with the locking tab 402 engaged with one of the locking tab notches 408. The clearance hole 340 is shown empty of the plunger rod. Thus, the locking disc 400 is shown in the locked, non-loaded position. The drive screw 314 is shown and the plunger rod support 412 is also shown. Referring now also to FIG. 4C, the plunger rod 310 is shown having fit through the clearance hole 340. The reservoir alignment tabs 307 are shown having mated with the reservoir tab openings 406, and the locking tab 402 is deflected from the locking tab notch 408.

The plunger rod support 412 is shown along part of the plunger rod 310. The plunger rod support 412 contributes to maintaining the integrity of the relationship of the plunger rod 310 and the drive screw 314 such that the drive screw 314 of the plunger rod 310 maintain connection and the plunger rod 310 is not deflected.

Referring now also to FIG. 4D, the locking disc 400 is shown after rotation and reservoir loading is complete, i.e., in the loaded position. The plunger rod 310 is engaged to the drive screw 314. The second locking tab notch 410 is now engaged with the locking tab 402. Thus, the locking disc 400 is locked from continuing further rotation.

Referring also to FIGS. 4M-4N, a sequential illustration of the loading of the reservoir and engagement of the drive screw 314 to the plunger rod 310 is shown. As the plunger rod 310 fits through the clearance hole, the reservoir 306 disengages the locking tab 402 from the first locking tab notch 408. The reservoir alignment tab 307 (the other tab is obscured) mates with the reservoir tab opening 406. As shown in FIG. 4N, the plunger rod 310 is engaged with the drive screw 314. The locking tab 402 is being engaged with the second locking tab notch 410.

In the exemplary embodiment, loading the reservoir into the pump barrel and engaging the plunger rod to the drive screw includes two steps. First, aligning the locking hub alignment tabs with the hub and battery end cap and dropping the reservoir and locking hub assembly into the pump barrel (the plunger rod being inherently aligned with the clearance hole of the locking disc). Second, rotating the locking hub until rotation stops, i.e., the locking tab has engaged with the second locking tab notch. In the exemplary embodiment, and referring again to FIG. 4F, the hub and battery end cap 404 may include an loading alignment feature 420, and the reservoir may also include a marking or other alignment feature, aligning the marking on the reservoir with the loading alignment feature 420 assures the reservoir assembly is aligned for dropping the reservoir and locking hub assembly into the pump barrel and completion of the loading steps. In the exemplary embodiment, the loading alignment feature 420 is a notch molded into the plastic of the hub and battery end cap 404. However, in other embodiments, the loading alignment feature 420 may be a bump, raised dimple, notch of a different shape, or a painted marking, i.e., any feature that may be utilized by the user in loading the reservoir and locking hub assembly. The complementary feature on the reservoir may be any marking, for example, a painted marking with an indication of the direction of loading, e.g., "pump ->>", "-■>>", or, in some embodiments, a simple vertical line of any length, a dot or other symbol that may be utilized by the user in loading the reservoir and locking hub assembly. In these embodiments, these alignment features further simplify the method of loading the reservoir and locking hub assembly into the pump assembly.

Referring again to FIG. 1C, the hub and battery end cap is shown populated with a locking hub 108 and a battery cap 110. In this embodiment of the pump assembly, the locking hub 108 sits flush with the pump assembly. Thus, when loading of the reservoir, once the locking hub has been rotated such that the locking hub is flush with the pump assembly body, loading is complete. Thus, reservoir loading is advantageously simplified in that the alignment features assure that the reservoir, when dropped into the pump barrel, the plunger rod and reservoir alignment tabs are aligned with the locking disc and, the rotation of the locking hub until the locking hub is flush with the pump assembly assures that reservoir loaded and the plunger rod is threaded to the drive screw.

Referring now to FIG. 5A, a view of the exemplary embodiment of the plunger rod 310 and plunger 308 is shown. The plunger 308 includes two O-rings 366. In some embodiments, the O-rings 366 and plunger 308 may be one piece and may be made from a material that provides ample sealing properties.

Referring now to FIGS. 5B-5C, another embodiment of the reservoir assembly 502, together with the locking hub 318, is shown. In this embodiment, the plunger seal 506 is designed to function as a double o-ring plunger, however, is molded as a single part. The plunger seal 506 fits over the plunger 504, which, in some embodiments, is made from plastic, and in some embodiments, is made from the same plastic as the plunger rod 310. The plunger cap 508 fits over the plunger seal 506. The reservoir 306 and reservoir bottom 305, in some embodiments, may be as described in the above described embodiments. Referring also to FIGS. 5D-5E, the plunger seal 506 is shown. As shown, the top ring-like feature of the seal is thicker than the bottom ring-like feature. However, in other embodiments, the bottom ring-like feature may be the thicker ring-like feature, and in some embodiments, both ring-like features may be the same thickness. Referring also to FIG. 5F, a cross section of the assembled plunger of the embodiments shown in FIGS. 5B-5E is shown. The plunger seal 506 fits around the plunger 504 and the plunger cap 504 snaps over the plunger seal 506. Referring now to FIGS. 5G-5P, various embodiments of the plunger seal 506 described above are shown.

As described above, the plunger rod is connected to the plunger, and is part of the reservoir assembly. The reservoir, as discussed above, functions to hold a volume of liquid for delivery by the infusion pump assembly. Filling the reservoir with a liquid, e.g. insulin, prior to leading the reservoir assembly into the pump assembly is preferred. Thus, in practice, a user loads the reservoir with insulin (or another liquid as discussed herein), attached the locking hub (in the exemplary embodiments, although, as discussed above, in some embodiments, the locking hub may be integrated with the reservoir) and loads the reservoir assembly with locking hub into the pump assembly.

In the exemplary embodiments, the plunger rod is designed, as shown herein, to engage with the drive screw and be driven by the drive screw. Thus, it may be difficult for some users to load the reservoir from a vial of insulin as the plunger rod is designed for drive screw engagement, not necessarily for human finger engagement. Thus, in some embodiments, a filling aid may be desirable.

Referring now to FIGS. 6A-6D, an exemplary embodiment of the reservoir filling aid 600 is shown. In this embodiment, the filling aid 600 is designed to engage with the threaded portion of the plunger rod 310 as described above, i.e., the filling aid includes a mating thread portion 602. The filling aid 600 slides onto the plunger rod 310, and as the mating thread portion 602 engages with the plunger rod threads 320, the filling aid 600 is securely fastened to the plunger rod 310. The handle 604, in the exemplary embodiment, is shaped to accommodate user's fingers and serves as pull. In practice, the user loads the reservoir by pulling back on the handle 604. Once the user has filled the reservoir, the filling aid 600 may be easily removed from the plunger rod by moving the filling aid 600 such that the threads disengage with the plunger rod threads. The filling aid 600, in the exemplary embodiment, is designed to have tolerances such that the plunger rod threads are not damaged during the filling process. In various embodiments, the filling aid may be different shapes, for example, larger, or the handle may be shaped differently, to accommodate those users with arthritis or other ailments that may prevent them from easily utilizing the filling aid as shown. An alternate embodiment is shown in FIGS. 6E-6F. In the exemplary embodiment, the filling aid 600 is made from plastic, however, in other embodiments, the filling aid 600 may be made from any materials, including but not limited to, stainless steel or aluminum.

Referring now to FIGS. 6G-6I, in some embodiments, the filling aid 606 may be connected to the plunger rod 301 by way of a plastic piece 608. In these embodiments, the plastic piece 608 is manufactured such that the filling aid 606 may be removed from the plunger rod 310 by bending the plastic piece, i.e., the filling aid 606 snaps off the plunger rod 310. Although the filling aid 606 in these FIGS, is shown having a particular shape, in other embodiments, the shape may be any of the other filling aid embodiments shown herein, or others that may be designed as discussed above. In some of the "snap-off embodiments of the filling aid, the filling aid 606 and plastic piece 608 may be molded with the plunger rod 310.

Referring now to FIGS. 7A-7B, the pump assembly 100 is shown. Referring to FIGS. 1A-1B, the pump assembly 100 includes a housing, which, in the exemplary embodiment, is made from an aluminum portion, plastic portions, and rubber portions. However, in various embodiments, the materials and the portions vary, and include but are not limited to, rubber, aluminum, plastic, stainless steel, and any other suitable materials. In the exemplary embodiment, the back of the housing, shown in FIG. IB, includes a contour.

Referring now to FIGS. 7A-7B, portions of the housing has been removed. The switch assemblies/input devices and the user interface screen have been removed. The pump barrel 312 is shown with a reservoir 306 inside. The battery compartment 706 is shown in FIG. 7A, and the pump assembly 100 is shown without the battery compartment 706 is FIG. 7B. Various features of the battery compartment 706 are described herein. The gear box 364 is shown assembled with the pump housing 360 in the pump assembly 100. The hub and battery end cap 404 is shown assembled on the pump assembly 100

Referring now to FIGS. 7C-7D, a reservoir assembly 312 is shown engaged to the drive screw 314 and in contact with the strain gauge 708. As described in more detail herein, the strain gauge 708 is in contact with the drive screw 314. The pressure measurements of the strain gauge 708 are taken by an electrical contact 710. The strain gauge 708 measures the pressure exerted by the drive screw 314. Although the methods for sensing an occlusion are described in more detail herein, where the drive screw 314 is unable to drive the plunger rod 310 further into the reservoir, the drive screw 314 will exert pressure onto the strain gauge 708.

Referring now to FIG. 7E, an embodiment of an optical sensor is shown. The optical sensor, as described above and in more detail in U.S. Patent Application Publication US 2004/0135078 A1, published on Jul. 15, 2004 and entitled Optical Displacement Sensor for Infusion Devices, as used in some embodiments of the infusion pump apparatus, is a sensor used to determine whether the plunger rod 310 has moved and/or advanced and additionally, may also determine whether the plunger rod 310 has moved and/or advanced the intended distance. Thus, in the infusion pump system and apparatus described herein, the pump apparatus, using the occlusion detection methods and devices, can determine if the drive screw is unable to advance, and also, can determine if the plunger rod has moved and the distance in which it has moved.

Figure 8A:
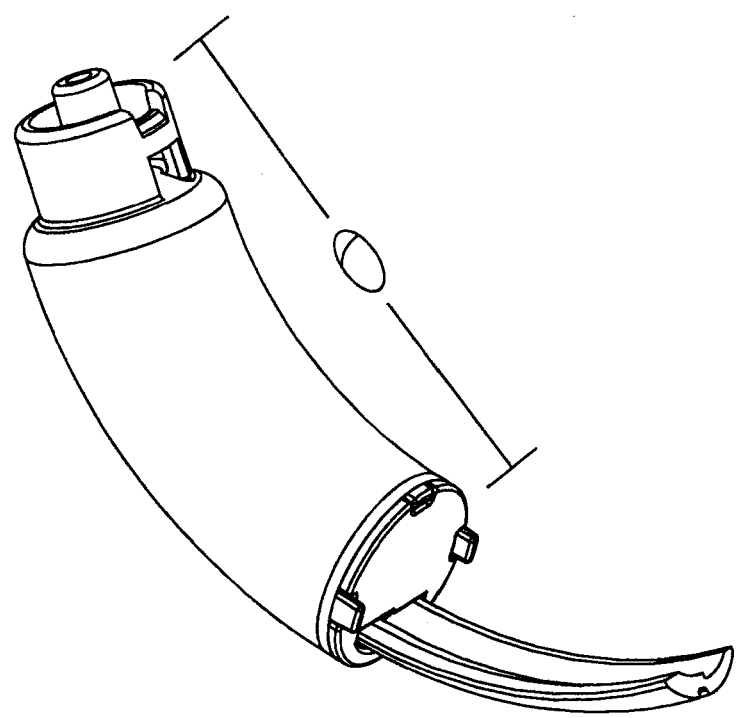
Figure 8B:
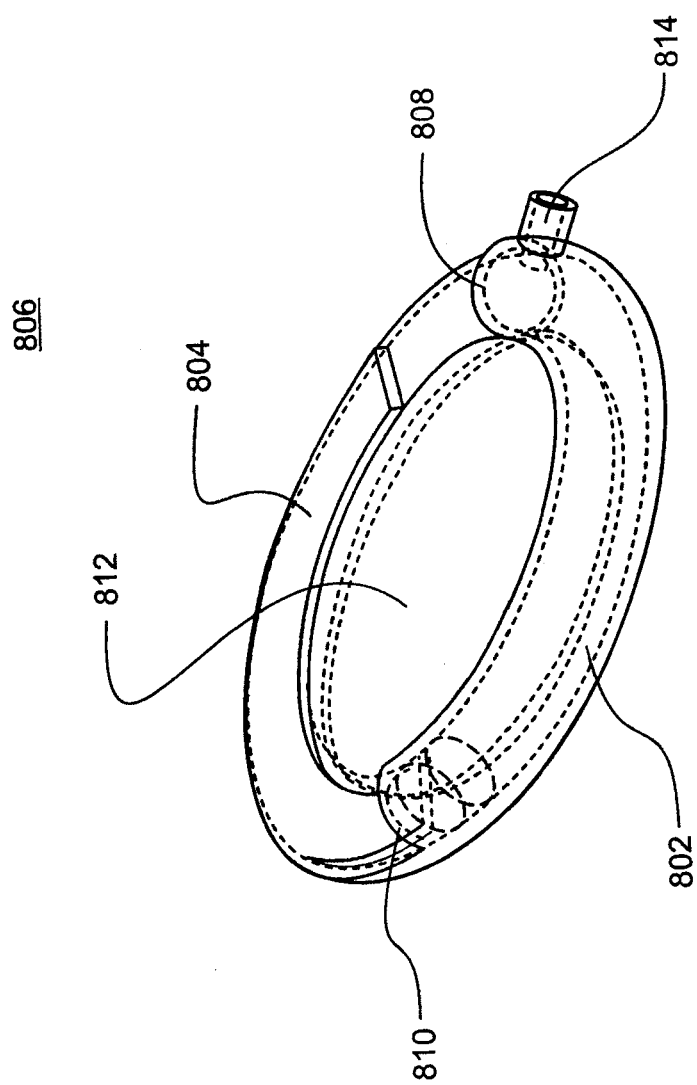
Figure 8C:
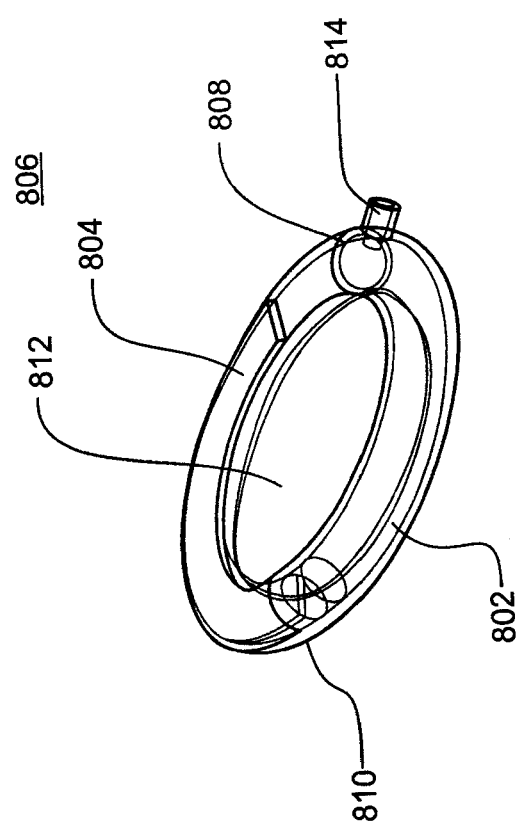

Referring now to FIGS. 8A-8D, alternate embodiments of the reservoir assembly are shown. Although the embodiments discussed and described above may be used in a pumping assembly, and in some embodiments, are used in the pumping assemblies shown and described herein, in other embodiments, the pumping assembly shape and size may vary from the ones shown herein. For example, the pump assembly may be round or smaller in shape. Therefore, it may be beneficial for the reservoir assembly to accommodate the smaller or rounded shape without having to sacrifice total volume. Exemplary embodiments of these alternate embodiment reservoir assemblies are shown in FIGS. 8A-8C. However, it should be understood these are by example only. Depending on the size and shape of the pump assembly, the alternate embodiment reservoir assembly may be larger, smaller, or include a larger or smaller angle.

Figure 8D:
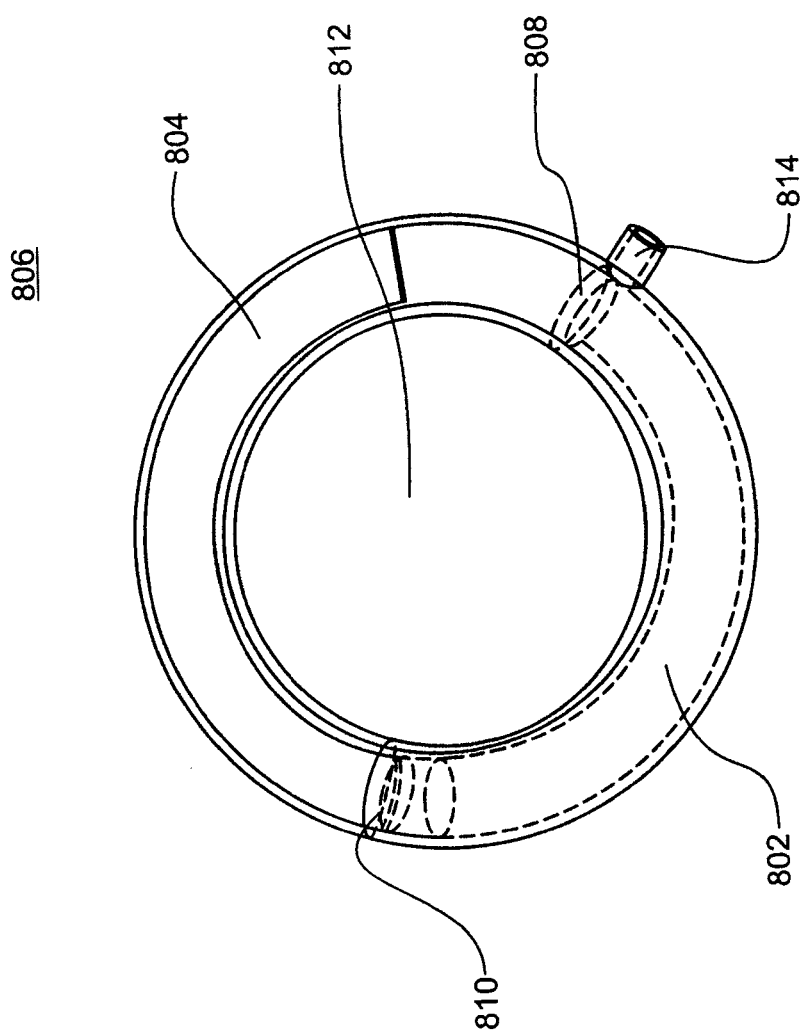

Referring now to FIG. 8A, a curved reservoir assembly 800 is shown. In the various embodiments, the angle indicated may have a value of greater than or less than 180 degrees. In one exemplary embodiment, the reservoir assembly 800 may have an angle of 150 degrees. In some embodiments, the reservoir assembly 800 may form a helical shape. In other embodiments, the reservoir assembly 800 may be any shape desired, including having one or more portions rounded or curved, and/or one or more portions straight or approaching straight. Referring now to FIGS. 8B-8D, another embodiment of the alternate embodiment reservoir assembly is shown. In this embodiment, the reservoir 802 and plunger 804 assembly is shown as having a round or approaching round shape. The reservoir 802, in some embodiments, and as shown in FIGS. 8B-8D, may be a channel in a housing 806. The reservoir 802 may be cylindrical, and the ends 808, 810 of the plunger 804 may be circular, however, the plunger 804 may be flat 804 as shown. In various embodiments, the plunger 804 may be advanced by applying pressure to the end 808 of the plunger 804 by a mechanical feature (not shown), which, in some embodiments, may be located in the center 812 of the housing 806, or in other embodiments, elsewhere in the pump assembly within engageable proximity to the plunger 804. In some embodiments, the reservoir 802 may be filled with liquid using inlet 814.

As discussed above, enclosure assembly 102 may include infusion port assembly 112 to which cannula assembly 114 may be releasably coupled. A portion of infusion port assembly 112 and a portion of cannula assembly 114 may form a medium connector assembly for releasably coupling infusion port assembly 112 to cannula assembly 114 and effectuating the delivery of infusible fluid 200 to user 202.

Referring to FIG. 9A, there is shown one exemplary embodiment of a medium connector assembly 900 for connecting medium carrying components (not shown) and allowing the flow of medium therebetween. Examples of medium carrying components may include, but are not limited to, a delivery catheter and an insulin delivery pump, a fluid supply (such as an intravenous fluid supply bag, a dialysate supply, etc.) and a pump supply catheter, or the like. Connector assembly 900 may include medium connector 902 associated with a first medium carrying component (not shown) and mating connector 904 associated with a second medium carrying component.

Medium connector 902 may include passage 906 to allow for the flow of medium. The medium flowing between the medium carrying components, e.g., via passage 906, may include liquids (e.g., insulin, dialysate, saline solution, or the like), gases (e.g., air, oxygen, nitrogen, or the like), suspensions, or the like. Further, medium connector 902 may include multi-portion engagement surface 908, generally, positioned about passage 906. Multi-portion engagement surface 908 may include first surface portion 910, and second surface portion 912.

As will be discussed below in greater detail, first surface portion 910 of multi-portion engagement surface 908 may be configured to provide an interference fit with corresponding sealing surface 914 of mating connector 904. Further, second surface portion 912 of multi-portion engagement surface 908 may be configured to provide a clearance fit with corresponding sealing surface 914 of mating connector 904. The ratio of first surface portion 910 and second surface portion 912 may be selected to regulate an engagement for between medium connector 902 and mating connector 904.

For example, corresponding sealing surface 914 of mating connector 904 may include a tapered surface, e.g., which may include a 6% taper (e.g., approximately 3.4 degree included taper) of a standard Luer taper connector (e.g., as defined by the ISO 594 standard). Of course, corresponding sealing surface 914 may include tapers other than a 6% Luer taper. Multi-portion engagement surface 908 may similarly include a tapered surface, in which first surface portion 910 may have a first taper angle, and second surface portion 912 may have a second taper angle that is less than the first taper angle. In one particular embodiment, the second taper angle may approach zero, such that second surface portion 912 may be generally cylindrical (e.g., may include a slight taper, such as a draft angle to facilitate manufacture). Of course, second surface portion 912 may include other, non-cylindrical, taper angles.

Continuing with the above-stated example, first surface portion 910 of multi-portion engagement surface 908 may include a first taper angle corresponding to the angle of corresponding sealing surface 914 of mating connector 904 (e.g., a 6% taper). As shown in FIG. 9B, the corresponding taper of first surface portion 910 may provide an interference fit with corresponding sealing surface 914 of mating connector 904. As also shown, the second taper angle of second surface portion 912 may provide a clearance fit with corresponding sealing surface 914 of mating connector 904, e.g., which may result in at least partial clearance 916 between second surface portion 912 and corresponding sealing surface 914.

The contact surface area of medium connector 902 and mating connector 904 may remain generally constant once first surface portion 910 has engaged corresponding sealing surface 914. For example, as first surface portion 910 may be configured to provide an interference fit with corresponding sealing surface 914, while second surface portion 912 of multi-portion engagement surface 908 may be configured to provide a clearance fit with corresponding sealing surface 914, only first surface portion 910 may engage corresponding sealing surface 914.

Once first surface portion 910 engages corresponding sealing surface 914, further insertion of medium connector 902 relative to mating connector 904 may be attributable to the elastic and/or plastic deformation force of medium connector 902 in the region of first surface portion 910 and/or of mating connector 904 in the region of contact between corresponding sealing surface 914 and first surface portion 910 (e.g., as first surface portion 910 is forced into the progressively smaller opening provided by corresponding sealing surface 914), and the frictional interaction between first surface portion 910 and corresponding sealing surface 914 of mating connector 904.

As such, the ratio of first surface portion 910 and second surface portion 912 may be selected to regulate an engagement force between medium connector 902 and mating connector 904. As discussed above, second surface portion 912 may be configured to provide a clearance fit with corresponding sealing surface 914, and as such may not contribute to the engagement force (e.g., the insertion force per increment of axial insertion) between medium connector 902 and mating connector 904. Therefore, the ratio of first surface portion 910 to second surface portion 912 may be increased to increase the engagement force between medium connector 902 and mating connector 904. Conversely, the ratio of first surface portion 910 to second surface portion 912 may be decreased to decrease the engagement force between medium connector 902 and mating connector 904.

The ability to regulate the engagement force between medium connector 902 and mating connector 904 (e.g., based upon the ratio of first surface portion 910 and second surface portion 912) may allow the use of features associated with medium connector 902 (and/or the first associated medium carrying component) and/or mating connector 904 (and/or the second associated medium carrying component) which may require a minimum insertion depth to be achieved within a selected range of insertion forces. For example, medium connector 902 may include one or more retention features, e.g., which may facilitate a positive engagement and/or relative position between medium connector 902 and mating connector 904. As shown in FIGS. 9A-9B, the one or more retention features may include one or more snap-fit features (e.g., cooperating snap-fit features 918, 920A, respectively associated with medium connector 902 and mating connector 904). As shown, one or more of cooperating snap-fit features 918, 920A may be disposed on a cantilever feature (e.g., cantilever arm 922), e.g., which may facilitate engagement/dis-engagement of cooperating snap-fit features 918, 920A. Snap-fit features 918, 920A may require a minimum insertion depth to provide engagement therebetween. As described above, the ratio of first surface portion 910 and second surface portion 912 may be selected to regulate the engagement force between medium connector 902 and mating connector 904 associated with the insertion depth necessary to provide engagement between snap-fit features 918, 920A. While regulating the engagement force between the medium connector and the mating connector has been described in connection with the use of retention features, this is not intended as a limitation of the present disclosure, as the ability to regulate the engagement force between the medium connector and the mating connector may equally be used for other purposes.

Referring also to FIGS. 9C and 9D, the medium connector assembly may include medium connector 902 associated with a first medium carrying component (not shown) and mating connector 904 associated with a second medium carrying component. As shown, one or more of the cooperating snap-fit features (e.g., cooperating snap-fit features 918, 920B) may be provided as a feature associated with one of the mating surfaces of the medium connector assembly (e.g., snap-fit feature 920B may be formed on member 924 defining corresponding sealing surface 914). Based upon, at least in part, the illustrated exemplary embodiments of FIGS. 9A-9B and 9C-9D, various additional/alternative arrangements may be readily understood, and are contemplated by the present disclosure.

In addition/as an alternative to the second surface portion including a second taper angle, the second surface portion may include one or more recesses. For example, and referring also to FIG. 9E, the second surface portion may include one or more recesses including one or more longitudinal slots (e.g., longitudinal slot 950), e.g., which may be formed in first surface portion 910. Longitudinal slot 950 may be configured to provide a clearance fit with cooperating sealing surface 114 of mating connector 904. For example, longitudinal slot 950 may provide a second surface portion which may not engage cooperating sealing surface 914 when first surface portion 910 is fully engaged with cooperating sealing surface 914 of mating connector 904. The ratio of first surface portion 910 and the radial slots (e.g., longitudinal slot 950) may be selected to regulate the engagement force between medium connector 902 and mating connector 904, e.g., in as much as longitudinal slot 950 may not provide a frictional engagement force with cooperating sealing surface 914 of mating connector 904.

Referring also to FIG. 9F, additionally/alternatively the second surface portion may include one or more recesses that may include one or more radial slots (e.g., radial slot 952). Similar to the above-described longitudinal slots (e.g., longitudinal slot 950), radial slot 952 may be configured to provide a clearance fit with corresponding sealing surface 914 of mating connector 904. As such, the ratio of first surface portion 910 and the radial slots (e.g., radial slot 952) may be selected to regulate the engagement force between medium connector 902 and mating connector 904. For example, radial slot 952 may not provide a frictional engagement force with cooperating sealing surface 914 of mating connector 904.

In addition to the specifically described and depicted recesses in the form of longitudinal slots and radial slots, the one or more recesses may include various additional and/or alternative configurations (e.g., dimples, etc.), which maybe configured to provide a clearance fit with the cooperating sealing surface of the mating connector. As such, the ratio of the first surface portion and the second surface portion (including one or more recesses) may be selected to regulate an engagement force between the medium connector and the mating connector. Further, it will be appreciated that the number, arrangement, and character of the one or more recesses may vary according to design criteria and preference.

While the above-described embodiments have been depicted having a multi-portion engagement surface configured as a male medium connector portion, referring also to FIGS. 9G-9H, medium connector 902 may additionally/alternatively be configured as a female connector portion. For example, medium connector 902 may include a female connector portion having a multi-portion engagement surface including first surface portion 910 and second surface portion 912. As shown in FIG. 9G, the multi-portion engagement surface may include a tapered surface, in which first surface portion 910 may have a first taper angle configured to provide an interference fit with cooperating sealing surface 914 of male mating connector 904. Further, second surface portion 912 may have a second taper angle that is greater than the first taper angle. As such, second surface portion 912 may be configured to provide a clearance fit with cooperating sealing surface 914 of male mating connector 904.

Further, the second surface portion may include one or more recesses. For example, and referring also to FIGS. 9H-9I, the one or more recesses may include one or more longitudinal slots (e.g., longitudinal slot 950A, 950B). Similar to previously described embodiments, first surface portion 910 may be configured to provide an interference fit with cooperating sealing surface 914 of male mating connector 904. Further, the second surface portion, including longitudinal slot 950A, 950B, may be configured to provide a clearance fit with cooperating sealing surface 914 of male mating connector 904. Medium connector 902 may include sealing region 954, which may not include longitudinal slots, e.g., to thereby facilitate achieving a seal between first surface portion 910 and cooperating sealing surface 914 of mating connector 904.

Referring also to FIG. 9J, the second surface portion may include one or more recesses, in which the one or more recesses may include one or more radial slots (e.g., radial slot 952). Radial slot 952 may be configured to provide a clearance fit with cooperating sealing surface 914 of male mating connector 904.

In addition to the specifically described and depicted recesses in the form of longitudinal slots and radial slots, the one or more recesses may include various additional and/or alternative configurations (e.g., dimples, etc.), which may be configured to provide a clearance fit with the cooperating sealing surface of the mating connector. As such, the ratio of the first surface portion and the second surface portion (including one or more recesses) may be selected to regulate an engagement force between the medium connector and the mating connector. Further, it will be appreciated that the number, arrangement, and character of the one or more recesses may vary according to design criteria and preference.

As discussed above, infusion pump assembly 100 may include a removable cover assembly 116 configured to allow access to power supply cavity 118 (shown in phantom on FIG. 2).

Referring also to FIGS. 10A-10C, power supply cavity 118 (which may be formed by a combination of removable cover assembly 116 and a portion of enclosure assembly 102) may be configured to releasably receive primary power supply 220. Additionally, power supply cavity 118 may be configured to prevent primary power supply 220 from being reverse-polarity electrically coupled to processing logic 204 For example, power supply cavity 118 may be configured to prevent positive terminal 1000 of primary power supply 220 from being electrically coupled to negative terminal 1002 of power supply cavity 118 and/or negative terminal 1004 of primary power supply 220 from being electrically coupled to positive terminal 1006 of power supply cavity 118).

Configuring power supply cavity 118 to prevent primary power supply 220 from being reverse-polarity electrically coupled to processing logic 204 may provide various benefits. For example, the configuration may prevent the loss of power from primary power supply 220 (e.g., discharge of the battery) where the primary power supply assembly 220 has been inserted incorrectly. In addition to functioning to not waste power, this configuration may also be a safety feature to infusion pump assembly 100. Infusion pump assembly 100 may rely on power for functionality. A user may rely on infusion pump assembly 100 to provide life-sustaining therapy, for example, by delivering insulin. Thus, preventing primary power supply 220 from being reverse-polarity electrically coupled to processing logic 204 (e.g., as a result of user 202 having mistakenly inserted primary power supply 220 incorrectly), preventing primary power supply 220 from being reverse-polarity electrically coupled to processing logic 204 may allow infusion pump assembly 100 to function for a longer time than if the incorrectly installed primary power supply 220 had been able to be reverse-polarity electrically coupled to processing logic 204.

Removable cover assembly 116 may be configured to allow access to power supply cavity 118 and effectuate the installation/replacement/removal of primary power supply 220. As discussed above, an example of primary power supply 220 may include but is not limited to a battery. In some embodiments, the battery may include, but is not limited to, an A, AA, AAA, or AAAA battery, and the battery may be a lithium battery or alkaline battery. The battery may, in some embodiments, be a rechargeable battery.

Removable cover assembly 116 may be configured to rotatably engage enclosure assembly 102 in the direction of arrow 1008. For example, removable cover assembly 116 may include first twist lock assembly 1010 (e.g., a protruding tab). Enclosure assembly 102 may include a second twist lock assembly 1012 (e.g., a slot) configured to releasably engage first twist lock assembly and effectuate the releasable engagement of the removable cover assembly and the enclosure assembly.

While removable cover assembly 116 and enclosure assembly 102 is described above as including first twist lock assembly 1010 and second twist lock assembly 1012, this is for illustrative purposes only and is not intended to be a limitation of this disclosure, as other configurations are possible and are considered to be within the scope of this disclosure. For example, one or more thread assemblies (not shown) may be utilized to effectuate the above-described rotatable engagement.

Further, while removable cover assembly 116 is described above as being configured to rotatably engage enclosure assembly 102, this is for illustrative purposes only and is not intended to be a limitation of this disclosure, as other configurations are possible. For example, removable cover assembly 116 may be configured to slidably engage enclosure assembly 102 (in the direction of arrow 1014) using a slide assembly (not shown). Alternatively, removable cover assembly 116 may be configured to be pressed into enclosure assembly 102 in the direction of arrow 1016.

Removable cover assembly 116 may include sealing assembly 1018 (e.g., an o-ring assembly) that is configured to releasably engage at least a portion of enclosure assembly 102 to form an essentially water-tight seal between removable cover assembly 116 and enclosure assembly 102.

In an embodiment in which sealing assembly 1018 includes an o-ring assembly included within removable cover assembly 116, the o-ring assembly may be sized to effectuate a watertight (or essentially watertight) seal with a corresponding surface of enclosure assembly 102.

Alternatively, in an embodiment in which sealing assembly 1018 includes an o-ring assembly included within enclosure assembly 102, the o-ring assembly may be sized to effectuate a watertight (or essentially watertight) seal with a corresponding surface of removable cover assembly 116.

Removable cover assembly 116 may include conductor assembly 1020 for electrically coupling positive terminal 1006 of removable cover assembly 116 with interior wall 120 (FIG. ID) of power supply cavity 118. For example, conductor assembly 1020 may include a plurality of tabs (e.g., tabs 1022, 1024) that may be electrically coupled to positive terminal 1006 of removable cover assembly 116. Tabs 1022, 1024 may be configured so that when removable cover assembly 116 releasably engages enclosure assembly 102, tabs 1022, 1024 may make electrical contact with interior wall 120 of power supply cavity 118. Interior wall 120 of power supply cavity 118 may then be electrically coupled to the various components within infusion pump assembly 100 that require electrical power, examples of which may include but are not limited to processing logic 204, As discussed above, the combination of removable cover assembly 116 and a portion of enclosure assembly 102 may be configured to prevent primary power supply 220 from being reverse-polarity electrically coupled to e.g., processing logic 204. Referring also to FIG. 11, one or more of negative terminal 1002 and positive terminal 1006 may be configured so that the above-described reverse polarity situation cannot occur. For example, removable cover assembly 116 may include insulator assembly 1026 that includes recess 1028 that is sized to receive positive terminal 1000 of primary power supply 220 and enable electrical contact with positive terminal 1006 of removable cover assembly 116. Insulator assembly 1026 may be constructed of an insulating material, such as PVC plastic or bakelite. Further, recess 1028 may be sized so that negative terminal 1004 of primary power supply 220 cannot make electrical contact with positive terminal 1006 (and may only make contact with insulator 1026), thus preventing primary power supply 220 from being electrically coupled to processing logic 204 in a reverse-polarity configuration.

Referring also to FIGS. 12A-12D, there is shown an alternative-embodiment removable cover assembly 116'. Removable cover assembly 116' may include sealing assembly 1018' (e.g., an o-ring assembly) that is configured to releasably engage at least a portion of enclosure assembly 102 to form an essentially water-tight seal between removable cover assembly 116' and enclosure assembly 102.

Removable cover assembly 116' may include conductor assembly 1020' for electrically coupling positive terminal 1006' of removable cover assembly 116' with interior wall 120 (FIG. ID) of power supply cavity 118 (FIG. ID). For example, conductor assembly 1020' may include a plurality of tabs (e.g., tabs 1022', 1024') that may be electrically coupled to positive terminal 1006' of removable cover assembly 116'. Tabs 1022', 1024' may be configured so that when removable cover assembly 116' releasably engages enclosure assembly 102, tabs 1022', 1024' may make electrical contact with interior wall 120 of power supply cavity 118. Interior wall 120 of power supply cavity 118 may then be electrically coupled to the various components within infusion pump assembly 100 that require electrical power, examples of which may include but are not limited to processing logic 204.

As discussed above, the combination of removable cover assembly 116' and a portion of enclosure assembly 102 may be configured to prevent primary power supply 220 from being reverse-polarity electrically coupled to processing logic 204. For example, removable cover assembly 116' may include insulator assembly 1026' that defines recess 1028' that is sized to receive positive terminal 1000 (FIG. 11) of primary power supply 220 (FIG. 11) and enable electrical contact with positive terminal 1006' of removable cover assembly 116'. Insulator assembly 1026', which may be constructed of an insulating material (e.g., PVC plastic or bakelite), may be molded into and/or a portion of removable cover assembly 116'. Further, recess 1028' may be sized so that negative terminal 1004 (FIG. 11) of primary power supply 220 cannot make electrical contact with positive terminal 1006' (and may only make electrical contact with insulator 1026', thus preventing primary power supply 220 from being electrically coupled to processing logic 204 in a reverse-polarity configuration.

While power supply cavity 118 is described above as having positive terminal 1006 positioned proximate removable cover assembly 116, this is for illustrative purposes only and is not intended to be a limitation of this disclosure, as other configurations are possible and are considered to be within the scope of this disclosure. For example, negative terminal 1002 may be positioned proximate removable cover assembly 116.

Referring also to FIG. 13, there is shown a more-detailed diagrammatic view of processing logic 204. Processing logic 204 may include one or more circuit partitioning components 1300, 1302 configured to divide processing logic 204 into primary processing logic 1304 and backup processing logic 1306. Examples of one or more circuit partitioning components 1300, 1302 may include but are not limited to diode assembly 1300 and current limiting assembly 1302.

Diode assembly 1300 may be configured to allow primary power supply 220 to charge backup power supply 1308 included within backup processing logic 1306, while prohibiting backup power supply 1308 from providing backup electrical energy 1310 to primary processing logic 1304 in the event that some form of failure prevents primary electrical energy 1312 from providing primary processing logic 1304. An example of backup power supply 1308 may include but is not limited to a super capacitor assembly. An example of such a super capacitor assembly may include but is not limited to an electric double-layer capacitor manufactured by Elna Co. Ltd. of Yokohama, Japan.

Current limiting assembly 1302 may be configured to limit the amount of primary electrical energy 1312 available to charge backup power supply 1308. Specifically, as primary power supply 220 may be configured to charge backup power supply 1308, the amount of current available from primary power supply 220 may be limited to e.g., avoid depriving primary processing logic 1304 of a requisite portion of primary electrical energy 1312.

Primary processing logic 1304 may include primary microprocessor 1314 and voltage booster circuit 1316. An example of primary microprocessor 1314 may include but is not limited to a H8S/2000 manufactured by Renesas Technology America Inc. of San Jose, Calif. Voltage booster circuit 1316 may be configured to increase the voltage potential of primary electrical energy 1312 provided by primary power supply 220 to a level sufficient to power primary microprocessor 1314. An example of voltage booster circuit 1316 may include but is not limited to a LTC3421 manufactured by Linear Technology of Milpitas, Calif.

Current limiting assembly 1302 may be configured to limit the amount of current available to charge backup power supply 1308 during the power-up of primary microprocessor 1314. Specifically and for illustrative purposes, current limiting assembly 1302 may be controlled by primary microprocessor 1314 and current limiting assembly 1302 may be disabled (i.e., provide no charging current to backup power supply 1308) until after primary microprocessor 1314 is fully powered up. Upon primary microprocessor 1314 being fully powered up, primary microprocessor 1314 may now enable current limiting assembly 1302, thus providing charging current to backup power supply 1308. Alternatively and upon being initially energized, current limiting assembly 1302 may be configured to prohibit the flow of charging current to backup power supply 1308 for a time sufficient to allow for the powering up of primary microprocessor 1314.

Backup processing logic 1306 may include backup power supply 1308 and safety microprocessor 1318. An example of safety microprocessor 1318 may include but is not limited to a MSP430 manufactured by Texas Instruments of Dallas, Tex.

Primary power supply 220 may be configured to provide primary electrical energy 1312 to at least a portion of processing logic 204. Specifically and during normal operation of infusion pump assembly 100, primary power supply 220 may be configured to provide primary electrical energy 1312 to all of processing logic 204 (including the various components of primary processing logic 1304 and backup processing logic 1306), as well as various subsystems included within infusion pump assembly 100.

Examples of such subsystems may include but are not limited to memory system 206, input system 208, display system 104, vibration system 210, audio system 212, motor assembly 214, force sensor 216, and displacement detection device 218.

Backup power supply 1308 may be configured to provide backup electrical energy 1310 to the at least a portion of processing logic 204 in the event that primary power supply 220 fails to provide primary electrical energy 1312 to at least a portion of processing logic 204. Specifically, in the event that primary power supply 220 fails and, therefore, can no longer provide primary electrical energy 1312 to processing logic 204, backup power supply 1308 may be configured to provide backup electrical energy 1310 to backup processing logic 1306.

For illustrative purposes only, assume that infusion pump assembly 100 is operating normally and primary power supply 220 is providing primary electrical energy 1312 to processing logic 204. As discussed above, voltage booster circuit 1316 may increase the voltage potential of primary electrical energy 1312 to a level sufficient to power primary microprocessor 1314, wherein voltage booster circuit 1316 and primary microprocessor 1314 are both included within primary processing logic 1304.

Further, diode assembly 1300 may allow a portion of primary electrical energy 1312 to enter backup processing logic 1306, thus enabling the operation of safety microprocessor 1318 and the charging of backup power supply 1308. As discussed above an example of backup power supply 1308 may include but is not limited to a super capacitor. As discussed above, current limiting assembly 1302 may limit the quantity of current provided by primary power supply 220 to backup processing logic 1306, thus preventing the diversion of too large a portion of primary electrical energy 1312 from primary processing logic 1304 to backup processing logic 1306.

Accordingly, in addition to powering safety microprocessor 1318, primary power supply 220 may charge backup power supply 1308. In a preferred embodiment, backup power supply 1308 is a 0.33 farad super capacitor.

Safety microprocessor 1318 may monitor the status of primary power supply 220 by monitoring (via conductor 1320) the voltage potential present at the input of voltage booster circuit 1316. Alternatively, safety microprocessor 1318 may monitor the status of primary power supply 220 by e.g. monitoring the voltage potential present at the output of voltage booster circuit 1316. Further still, safety microprocessor 1318 and primary microprocessor 1314 may be electrically-coupled via e.g. conductor 1322 and primary microprocessor 1314 may be configured to continuously provide a "beacon" signal to safety microprocessor 1318. Conductor 1322 may include isolation circuit 1324 (e.g., one or more diodes assemblies) to electrically isolate safety microprocessor 1318 and primary microprocessor 1314. Accordingly, provided safety microprocessor 1318 continues to receive the "beacon" signal from primary microprocessor 1314, primary microprocessor 1314 is functioning and, therefore, being properly powered by primary power supply 220. In the event that safety microprocessor 1318 fails to receive the "beacon" signal from primary microprocessor 1314, an alarm sequence maybe initiated.

Further still, safety microprocessor 1318 may be configured to continuously provide a "beacon" signal to primary microprocessor 1314. Accordingly, provided primary microprocessor 1314 continues to receive the "beacon" signal from safety microprocessor 1318, safety microprocessor 1318 is functioning and, therefore, being properly powered by backup power supply 1308. In the event that primary microprocessor 1314 fails to receive the "beacon" signal from safety microprocessor 1318, an alarm sequence may be initiated.

As used in this disclosure, a "beacon" signal may be considered an event that is performed by primary microprocessor 1314 (and/or safety microprocessor 1318) solely for the purpose of making the presence of primary microprocessor 1314 (and/or safety microprocessor 1318) known. Additionally/alternatively, the "beacon" signal may be considered an event that is performed by primary microprocessor 1314 (and/or safety microprocessor 1318) for the purpose of performing a task, wherein the execution of this event is monitored by safety microprocessor 1318 (and/or primary microprocessor 1314) to confirm the presence of primary microprocessor 1314 (and/or safety microprocessor 1318).

Assume for illustrative purposes that primary power supply 220 fails. For example, assume that primary power supply 220 physically fails (as opposed to simply becoming discharged). Examples of such a failure may include but are not limited to the failing of a cell (not shown) within primary power supply 220 and the failing of a conductor (e.g., one or more of conductors 1320, 1326) that electrically-couples primary power supply 220 to processing logic 204. Accordingly, in the event of such a failure, primary power supply 220 may no longer provide primary electrical energy 1312 to processing logic 204.

However, when such a failure of primary power supply 220 occurs, the voltage potential present at the output of voltage booster circuit 1316 and the voltage potential present at the input of voltage booster circuit 1316 may be reduced to zero. Since safety microprocessor 1318 may monitor (as discussed above) one or more of these voltage potentials, safety microprocessor 1318 may be knowledgeable that primary power supply 220 has failed.

Further, when such a failure of primary power supply 220 occurs, primary microprocessor 1314 will no longer be powered and, therefore, primary microprocessor 1314 will no longer produce the above-described "beacon" signals. Since safety microprocessor 1318 monitors the above-described "beacon" signals, safety microprocessor 1318 may be knowledgeable that primary power supply 220 has failed.

As discussed above, in the event of such a failure of primary power supply 220, as diode assembly 1300 is reversed-biased, backup power supply 1308 may not provide backup electrical energy 1310 to primary processing logic 1304. Accordingly, primary processing logic 1304 will no longer function.

Upon sensing the failure of primary power supply 220, safety microprocessor 1318 may initiate an alarm sequence that may result in audio system 212 being energized. Audio system 212 may be controllable by both safety microprocessor 1318 and primary microprocessor 1314. Alternatively, a separate audio system may be used for each of safety microprocessor 1318 and primary microprocessor 1314. An example of audio system 212 may include but is not limited to a Piezo electric diaphragm, an example of which may include but is not limited to a 7BB-15-6 manufactured by Murata of Kyoto, Japan.

Audio system 212 may further include an RS232 line driver circuit 1330, such as a MAX3319/MAX3221 manufactured by Maxim Integrated Products of Sunnyvale, Calif. One or more or primary microprocessor 1314 and safety microprocessor 1318 may be configured to provide an alarm control signal (e.g., a square wave; not shown) to RS232 line driver circuit 1330 to generate an alarm output signal (not shown) that may be provided to and may drive the above-described Piezo electric diaphragm.

The alarm sequence initiated by safety microprocessor 1318 is intended to inform user 202 of the failure of primary power supply 220 so that user 202 may take the appropriate action (e.g. seeking an alternative means to have their therapy performed and/or having infusion pump assembly 100 repaired/replaced). Backup power supply 1308 may be sized so that safety microprocessor 1318 and audio system 212 may continue to function for up to fifteen minutes or more after the failure of primary power supply 220 (i.e., depending on design specifications).

The alarm sequence initiated by safety microprocessor 1318 and/or primary microprocessor 1314 may be an "escalating" alarm sequence. For example, at first a discrete "vibrating" alarm may be initiated (via vibration system 210). In the event that this "vibrating" alarm is not acknowledged within a defined period of time (e.g., one minute), a low volume audible alarm may be initiated. In the event that this low volume alarm is not acknowledged within a defined period of time (e.g., one minute), a medium volume audible alarm may be initiated. In the event that this medium volume alarm is not acknowledged within a defined period of time (e.g., one minute), a high volume audible alarm may be initiated. The escalating alarm sequence may provide a notification to user 202, in which the notification may be discrete or less disruptive at the onset. The initially discrete or less disruptive notification may be advantageous as user 202 may experience minimal disruption. However, in the event that user 202 does not acknowledge the alarm, the escalating nature of the alarm may provide for additional layers of safety to user 202. Additionally, in a case of audio system 212 error, or vibration system 210 error, the escalating alarm sequence, which may include both vibration and audio alarms, may insure that user 202 may be notified regardless of whether both systems 210, 212 are functioning.

Audio system 212, in some embodiments, may be configured to perform a self test upon power up. For example, upon infusion pump assembly 100 being initially powered up, audio system 212 may provide a "beep-type" signal to each sound generating device included within audio system 212. In the event that user 202 does not hear these "beep-type" signal(s), user 202 may take the appropriate action (e.g. seeking an alternative means to have their therapy performed and/or having infusion pump assembly 100 repaired/replaced). As discussed above, audio system 212 may be controllable by safety microprocessor 1318 and/or primary microprocessor 1314. Accordingly, when performing the above-described self test upon power up, safety microprocessor 1318 and/or primary microprocessor 1314 may control the above-described self test. This feature may provide for additional safety to user 202, as user 202 may be alerted to a system error earlier than may otherwise be the case. Thus, a method may be provided to notify the user early of system errors. Also, the system may otherwise not be aware of an error in audio system 212, thus, this feature provides for identification of a failure by user 202 that may otherwise go undetected.

During the failure of primary power supply 220, safety microprocessor 1318 may continue to monitor the voltage potential present at the output of voltage booster circuit 1316 and/or the voltage potential present at the input of voltage booster circuit 1316. Additionally, safety microprocessor 1318 may continue to monitor for the presence of the above-described "beacon" signals. Accordingly, in the event that the failure of primary power supply 220 was a temporary event (e.g. primary power supply 220 is an out-of-date battery and is being replaced with a new battery), safety microprocessor 1318 may be knowledgeable when primary power supply 220 is once again functioning properly.

Upon primary power supply 220 once again functioning properly, diode assembly 1300 and current limiting assembly 1302 may allow a portion of primary electrical energy 1312 produced by primary power supply 220 to recharge backup power supply 1308.

Additionally, safety microprocessor 1318 and primary microprocessor 1314 may each maintain a real-time clock, so that the various doses of infusible fluid may be dispensed at the appropriate time of day. As primary microprocessor 1314 was not functioning during the failure of primary power supply 220, the real-time clock maintained within primary microprocessor 1314 may no longer be accurate. Accordingly, the real-time clock maintained within safety microprocessor 1318 may be used to reset the real-time clock maintained within primary microprocessor 1314.

In order to further enhance the reliability and safety of infusion pump assembly 100, primary microprocessor 1314 and safety microprocessor 1318 may each execute applications written in different programming languages. For example, primary microprocessor 1314 may be configured to execute one or more primary applications written in a first computer language, while safety microprocessor 1318 may be configured to execute one or more safety applications written in a second computer language.

Examples of the first computer language in which the primary applications are written may include but are not limited to Ada, Basic, Cobol, C, C++, C#, Fortran, Visual Assembler, Visual Basic, Visual J++, Java, and Java Script languages. In a preferred embodiment, the first computer language in which the primary applications (executed on primary microprocessor 1314) are written is the C++ computer language.

Examples of the second computer language in which the safety applications are written may include but are not limited to Ada, Basic, Cobol, C, C++, C#, Fortran, Visual Assembler, Visual Basic, Visual J++, Java, and Java Script languages. In a preferred embodiment, the second computer language in which the safety applications (executed on safety microprocessor 1318) are written is the C computer language.

Further, assuming that primary microprocessor 1314 and safety microprocessor 1318 are different types of microprocessors and, therefore, use different compilers; the compiled code associated with the primary applications executed by primary microprocessor 1314 and the safety applications executed on safety microprocessor 1318 may be different (regardless of the whether the primary applications and the safety applications were written in the same computer language.

Examples of the one or more primary applications written in the first computer language and executable on primary microprocessor 1314 may include but are not limited to an operating system (e.g., Linux™, Unix™, Windows CE™), an executive loop and various software applications. Further, examples of the one or more safety applications written in the second computer language and executable on safety microprocessor 1318 may include but are not limited to an operating system (e.g., Linux™, Unix™, Windows CE™), an executive loop and various software applications.

Accordingly, primary processing logic 1304 and backup processing logic 1306 may each be configured as a separate stand-alone autonomous computing device. Therefore, primary microprocessor 1314 included within primary processing logic 1304 may execute a first operating system (e.g. Linux™) and safety microprocessor 1318 included within backup processing logic 1306 may execute an executive loop.

Additionally, primary microprocessor 1314 included within primary processing logic 1304 may execute one or more software applications (e.g. graphical user interface applications, scheduling applications, control applications, telemetry applications) executable within (in this example) a Linux™ operating system. Further, safety microprocessor 1318 included within backup processing logic 1306 may execute one or more software applications (e.g. graphical user interface applications, scheduling applications, control applications, telemetry applications) executable within (in this example) the executive loop.

By utilizing diverse computer languages and/or diverse operating systems, infusion pump assembly may be less susceptible to e.g. computer-language bugs, operating-system bugs, and/or computer viruses.

One or more of primary microprocessor 1314 (included within primary processing logic 1304 of processing logic 204) and safety microprocessor 1318 (included within backup processing logic 1306 of processing logic 204) may execute confirmation process 234 (FIG. 2). As will be discussed below in greater detail, confirmation process 234 may be configured to process a command received on a first microprocessor (e.g., primary microprocessor 1314) so that the command may be confirmed by a second microprocessor (e.g., safety microprocessor 1318).

The instruction sets and subroutines of confirmation process 234, which may be stored on a storage device (e.g., memory system 208) accessible by processing logic 204, may be executed by one or more processors (e.g., primary microprocessor 1314 and/or safety microprocessor 1318) and one or more memory architectures (e.g., memory system 208) included within infusion pump assembly 100. Examples of memory system 208 may include but are not limited to: a random access memory; a read-only memory; and a flash memory.

Referring also to FIG. 14, confirmation process 234 may receive 1400, on a first microprocessor executing one or more applications written in a first computer language, an initial command processable by the one or more applications written in the first computer language. For example and as discussed above, primary microprocessor 1314 (included within primary processing logic 1304) may be executing the Linux™ operating system. Assuming that user 202 wishes to have a 0.50 mL dose of infusible fluid 200 dispensed by infusion pump assembly 100, user 202 may select (via input system 208 and display system 104) the appropriate commands to have the 0.50 mL dose dispensed. Accordingly, primary microprocessor 1314 may receive 1400 a corresponding command (e.g., command 1332) to dispense 0.50 mL of infusible fluid 200.

As discussed above, safety microprocessor 1318 (included within backup processing logic 1306) may be executing the executive loop. Accordingly, command 1332 may not be provided to safety microprocessor 1318 in its native form, as safety microprocessor 1318 may not be capable of processing command 1332, due to safety microprocessor 1318 executing the executive loop and primary microprocessor 1314 executing the Linux™ operating system.

Accordingly, confirmation process 234 may convert 1402 initial command 1332 into a modified command (e.g., command 1334) that may be processable by e.g., safety microprocessor 1318 (included within backup processing logic 1306) that may be executing the executive loop. For example, confirmation process 234 may convert 1402 initial command 1332 into modified command 1334 that is transmittable via a communication protocol (not shown) that effectuates the communication of primary microprocessor 1314 and safety microprocessor 1318. Once command 1332 is converted 1402 into modified command 1334, modified command 1334 may be provided 1404 to e.g., safety microprocessor 1318 (included within backup processing logic 1306) that may be executing e.g., the executive loop.

Once received by e.g., safety microprocessor 1318 (included within backup processing logic 1306), safety microprocessor 1318 may process modified command 1334 and provide (via e.g., display system 104) a visual confirmation to user 202. Prior to processing modified command 1334, confirmation process 234 may convert modified command 1334 into a native command (not shown) processable by safety microprocessor 1318. For example, upon receiving modified command 1334, safety microprocessor 1318 may process received modified command 1334 to render (on display system 104) a visual confirmation.

Upon processing modified command 1334, confirmation process 234 may render on display system 104 a message that states e.g., "Dispense 0.50 U Dose?". Upon reading this message, user 202 may either authorize the dispensing of the 0.50 mL dose or cancel the dispensing of the 0.50 mL dose. Accordingly, if user 202 authorizes the dispensing of the 0.50 mL dose of infusible fluid 200, the accuracy of initial command 1332 and modified command 1334 are both confirmed. However, in the event that e.g., the message rendered by confirmation process 234 is incorrect (e.g., "Dispense 1.50 U Dose?"), the conversion 1402 of initial command 1332 to modified command 132 has failed. Accordingly, primary microprocessor 1314 (and/or the applications being executed on primary microprocessor 1314) and/or safety microprocessor 1318 (and/or the applications being executed on safety microprocessor 1318) may be malfunctioning. Accordingly, user 202 may need to seek an alterative means to having their therapy performed and/or have infusion pump assembly 100 serviced.

As discussed above, infusion pump assembly 100 may be configured to deliver infusible fluid 200 to user 202. Infusible fluid 200 may be delivered to user 202 via one or more different infusion event types. For example, infusion pump assembly 100 may deliver infusible fluid 200 via may a sequential, multi-part, infusion event (that may include a plurality of discrete infusion events) and/or a one-time infusion event.

Examples of such a sequential, multi-part, infusion event may include but are not limited to a basal infusion event and an extended-bolus infusion event. As is known in the art, a basal infusion event refers to the constant flow of a small quantity of infusible fluid 200. However, as such an infusion methodology is impractical/undesirable for an infusion pump assembly, when administered by such an infusion pump assembly, a basal infusion event may refer to the repeated injection of small (e.g. 0.05 unit) quantities of infusible fluid 200 at a predefined interval (e.g. every three minutes) that is repeated. The quantity of infusible fluid 200 delivered during each interval may be identical or may vary from interval to interval. Further, the time interval between each delivery of infusible fluid 200 may be identical or may vary from interval to interval. Further, the basal infusion rates may be pre-programmed time-frames, e.g., a rate of 0.50 units per hour from 6 am-3 pm; a rate of 0.40 units per hour from 3 pm-10 pm; and a rate of 0.35 units per hour from 10 pm-6 am. However, similarly, the basal rate may be 0.025 units per hour, and may not change according to pre-programmed time-frames. The basal rates may be repeated regularly/daily until otherwise changed.

Further and as is known in the art, and extended-bolus infusion event may refer to the repeated injection of small (e.g. 0.025 unit) quantities of infusible fluid 200 at a predefined interval (e.g. every three minutes) that is repeated for a defined number of intervals (e.g., three intervals) or for a defined period of time (e.g., one hour). An extended-bolus infusion event may occur simultaneously with a basal infusion event.

In contrast, as in known in the art, a normal bolus infusion event refers to a one-time infusion of infusible fluid 200. The volume of the infusible fluid 200 delivered in a bolus infusion event may be requested, and infusion pump assembly 100 may deliver the requested volume of infusible fluid 200 for the bolus infusion event at a predetermined rate (e.g., as quickly as the infusion pump assembly can deliver). However, the infusion pump assembly may deliver a normal bolus at a slower rate where the normal bolus volume is greater than a pre-programmed threshold.

Referring also to FIGS. 15-16, assume for illustrative purposes only that user 202 configures infusion pump assembly 100 to administer a basal dose (e.g. 0.05 units) of infusible fluid 200 every three minutes. As discussed above, infusion pump assembly 100 may include input system 208 and display system 104. Accordingly, user 202 may utilize input system 208 to define a basal infusion event for infusible fluid 200 (e.g., 1.00 units per hour), which may be confirmed via display system 104. While, in this example, the basal infusion event is described as 1.00 units per hour, this is for illustrative purposes only and is not intended to be a limitation of this disclosure, as either or both of the unit quantity and time period may be adjusted upward or downward. Infusion pump assembly 100 may then determine an infusion schedule based upon the basal infusion event defined; and may administer 100 infusible fluid 200. For example, infusion pump assembly 100 may deliver 0.05 units of infusible fluid 200 every three minutes, resulting in the delivery of the basal dose of infusible fluid 200 defined by the user (i.e., 1.00 units per hour).

Once defined and/or confirmed, fluid delivery process 236 may administer 1500 the sequential, multi-part, infusion event (e.g., 0.05 units of infusible fluid 200 every three minutes). Accordingly, while administering 1500 the sequential, multi-part, infusion event, infusion pump assembly 100: may infuse a first 0.05 unit dose 1600 of infusible fluid 200 at t=0:00 (i.e., a first discrete infusion event), may infuse a second 0.05 unit dose 1602 of infusible fluid 200 at t=3:00 (i.e., a second discrete infusion event); may infuse a third 0.05 unit dose 1604 of infusible fluid 200 at t=6:00 (i.e., a third discrete infusion event); may infuse a fourth 0.05 unit dose 1606 of infusible fluid 200 at t=9:00 (i.e., a fourth discrete infusion event); and may infuse a fifth 0.05 unit dose 1608 of infusible fluid 200 at t=12:00 (i.e., a fifth discrete infusion event). As discussed above, this pattern of infusing 0.05 unit doses of infusible fluid 200 every three minutes may be repeated indefinitely in this example, as this is an illustrative example of a basal infusion event.

Further, assume for illustrative purposes that infusible fluid 200 is insulin and sometime after the first 0.05 unit dose 1600 of infusible fluid 200 is administered 1500 by fluid delivery process 236 (but before the second 0.05 unit dose 1602 of infusible fluid 200 is administered 1500 by fluid delivery process 236), user 202 checks their blood glucose level and realizes that their blood glucose level is running a little higher than normal. Accordingly, user 202 may define an extended bolus infusion event via fluid delivery process 236. An extended bolus infusion event may refer to the continuous infusion of a defined quantity of infusible fluid 200 over a finite period of time. However, as such an infusion methodology is impractical/undesirable for an infusion pump assembly, when administered by such an infusion pump assembly, an extended bolus infusion event may refer to the infusion of additional small doses of infusible fluid 200 over a finite period of time.

Accordingly, user 202 may utilize input system 208 to define an extended bolus infusion event for infusible fluid 200 (e.g., 0.20 units over the next six minutes), which may be confirmed via display system 104. While, in this example, the extended bolus infusion event is described as 0.20 units over the next six minutes, this is for illustrative purposes only and is not intended to be a limitation of this disclosure, as either or both of the unit quantity and total time interval may be adjusted upward or downward. Once defined and/or confirmed, fluid delivery process 236 may determine an infusion schedule based upon the extended bolus infusion event defined; and may administer 1500 infusible fluid 200. For example, infusion pump assembly 100 may deliver 0.10 units of infusible fluid 200 every three minutes for the next two interval cycles (or six minutes), resulting in the delivery of the extended bolus dose of infusible fluid 200 defined by the user (i.e., 0.20 units over the next six minutes).

Accordingly, while administering 1500 the second, sequential, multi-part, infusion event, infusion pump assembly 100 may infuse a first 0.10 unit dose 1610 of infusible fluid 200 at t=3:00 (e.g., after administering the second 0.05 unit dose 1602 of infusible fluid 200). Infusion pump assembly 100 may also infuse a second 0.10 unit dose 1612 of infusible fluid 200 at t=6:00 (e.g., after administering the third 0.05 unit dose 1604 of infusible fluid 200).

Assume for illustrative purposes only that after user 202 programs infusion pump assembly 100 to administer 1500 the first sequential, multi-part, infusion event (i.e., 0.05 units infused every three minute interval repeated continuously) and administer 1500 the second sequential, multi-part, infusion event (i.e., 0.10 units infused every three minute interval for two intervals), user 202 decides to eat a very large meal. Predicting that their blood glucose level might increase considerably, user 202 may program infusion pump assembly 100 (via input system 208 and/or display system 104) to administer 1502 a one-time infusion event. An example of such a one-time infusion event may include but is not limited to a normal bolus infusion event. As is known in the art, a normal bolus infusion event refers to a one-time infusion of infusible fluid 200.

For illustrative purposes only, assume that user 202 wishes to have infusion pump assembly 100 administer 1502 a bolus dose of thirty-six units of infusible fluid 200. Fluid delivery process 236 may monitor the various infusion events being administered by fluid delivery process 236 to determine 1504 whether a one-time infusion event is available to be administered. If 1504 a one-time infusion event is available for administration 1502, fluid delivery process 236 may delay 1506 the administration of at least a portion of the sequential, multi-part, infusion event.

Continuing with the above-stated example, once user 202 completes the programming of fluid delivery process 236 to deliver one-time infusion event 1614 (i.e., the thirty-six unit bolus dose of infusible fluid 200), upon fluid delivery process 236 determining 1504 that the one-time infusion event is available for administration 1502, fluid delivery process 236 may delay 1506 the administration 1500 of each sequential, multi-part infusion event and administer 1502 the available one-time infusion event.

Specifically and as discussed above, prior to user 202 programming fluid delivery process 236 to deliver one-time infusion event 1614, infusion delivery process 236 was administering 1500 a first sequential, multi-part, infusion event (i.e., 0.05 units infused every three minute interval repeated continuously) and administering 1500 a second sequential, multi-part, infusion event (i.e., 0.10 units infused every three minute interval for two intervals).

For illustrative purposes only, the first sequential, multi-part, infusion event may be represented within FIG. 16 as 0.05 unit dose 1600 @t=0:00, 0.05 unit dose 1602 @t=3:00, 0.05 unit dose 1604 @t=6:00, 0.05 unit dose 1606 @t=9:00, and 0.05 unit dose 1608 @t=12:00. As the first sequential, multi-part, infusion event is described above is a basal infusion event, infusion pump assembly 100 (in conjunction with fluid delivery process 236) may continue to infuse 0.05 unit doses of infusible fluid 200 at three minute intervals indefinitely (i.e., until the procedure is cancelled by user 202).

Further and for illustrative purposes only, the second sequential, multipart, infusion event may be represented within FIG. 16 as 0.10 unit dose 1610 @t=3:00 and 0.10 unit dose 1612 @t=6:00. As the second sequential, multi-part, infusion event is described above as an extended bolus infusion event, infusion pump assembly 100 (in conjunction with fluid delivery process 236) may continue to infuse 0.10 unit doses of infusible fluid 200 at three minute intervals for exactly two intervals (i.e., the number of intervals defined by user 202).

Continuing with the above-stated example, upon fluid delivery process 236 determining 1504 that the thirty-six unit normal bolus dose of infusible fluid 200 (i.e., one-time infusion event 1614) is available for administration 1502, fluid delivery process 236 may delay 1506 the administration 1500 of each sequential, multi-part infusion event and may start administering 1502 one-time infusion event 1614 that is available for administration.

Accordingly and for illustrative purposes only, assume that upon completion of the programming of infusion pump assembly 100 to deliver the thirty-six unit normal bolus does of infusible fluid 200 (i.e., the one-time infusion event), fluid delivery process begins administering 1502 one-time infusion event 1614. Being that one-time infusion event 1614 is comparatively large, it may take longer than three minutes (i.e., the time interval between individual infused doses of the sequential, multi-part, infusion events) to administer and, therefore, one or more of the individual infused doses of the sequential, multi-part, infusion events may need to be delayed.

Specifically, assume that it will take infusion pump assembly 100 greater than six minutes to infuse thirty-six units of infusible fluid 200. Accordingly, fluid delivery process 236 may delay 0.05 unit dose 1602 (i.e., scheduled to be infused @t=3:00), 0.05 unit dose 1604 (i.e., scheduled to be infused @t=6:00), and 0.05 unit dose 1606 (i.e., scheduled to be infused @t=9:00) until after one-time infusion event 1614 (i.e., the thirty-six unit normal bolus dose of infusible fluid 200) is completely administered. Further, fluid delivery process 236 may delay 0.10 unit dose 1610 (i.e., scheduled to be infused @t=3:00 and 0.10 unit dose 1612 (i.e., scheduled to be infused @t=6:00) until after one-time infusion event 1614.

Once administration 1502 of one-time infusion event 1614 is completed by fluid delivery process 236, any discrete infusion events included within the sequential, multi-part, infusion event that were delayed may be administered 1500 by fluid delivery process 236.

Accordingly, once one-time infusion event 1614 (i.e., the thirty-six unit normal bolus dose of infusible fluid 200) is completely administered 1502, fluid delivery process 236 may administer 1500 0.05 unit dose 1602, 0.05 unit dose 1604, 0.05 unit dose 1606, 0.10 unit dose 1610, and 0.10 unit dose 1612.

While fluid delivery process 236 is shown to administer 1500 0.05 unit dose 1602, then 0.10 unit dose 1610, then 0.05 unit dose 1604, then 0.10 unit dose 1612, and then 0.05 unit dose 1606, this is for illustrative purposes only and is not intended to be a limitation of this disclosure, as other configurations are possible and are considered to be within the scope of this disclosure. For example, upon fluid delivery process 236 completing the administration 1502 of one-time infusion event 1614 (i.e., the thirty-six unit normal bolus dose of infusible fluid 200), fluid delivery process 236 may administer 1500 all of the delayed discrete infusion events associated with the first sequential, multi-part infusion event (i.e., namely 0.05 unit dose 1602, 0.05 unit dose 1604, and 0.05 unit dose 1606. Fluid delivery process 236 may then administer 1500 all of the delayed discrete infusion events associated with the second sequential, multi-part infusion event (i.e., 0.10 unit dose 1610, and 0.10 unit dose 1612).

While one-time infusion event 1614 (i.e., the thirty-six unit normal bolus dose of infusible fluid 200) is shown as being infused beginning at t=3:00, this is for illustrative purposes only and is not intended to be a limitation of this disclosure. Specifically, fluid delivery process 236 may not need to begin infusing one-time infusion event 1614 at one of the three-minute intervals (e.g., t=0:00, t=3:00, t=6:00, t=9:00, or t=12:00) and may begin administering 1502 one-time infusion event 1614 at any time.

While each discrete infusion event (e.g., 0.05 unit dose 1602, 0.05 unit dose 1604, 0.05 unit dose 1606, 0.10 unit dose 1610, and 0.10 unit dose 1612) and onetime infusion event 1614 are shown as being a single event, this is for illustrative purposes only and is not intended to be a limitation of this disclosure. Specifically, at least one of the plurality of discrete infusion events e.g., 0.05 unit dose 1602, 0.05 unit dose 1604, 0.05 unit dose 1606, 0.10 unit dose 1610, and 0.10 unit dose 1612) may include a plurality of discrete infusion sub-events. Further, one-time infusion event 1614 may include a plurality of one-time infusion sub-events.

Referring also to FIG. 17 and for illustrative purposes, 0.05 unit dose 1602 is shown to include ten discrete infusion sub-events (e.g., infusion sub-events 1700 i_io), wherein a 0.005 unit dose of infusible fluid 200 is infused during each of the ten discrete infusion sub-events. Additionally, 0.10 unit dose 1610 is shown to include ten discrete infusion sub-events (e.g., infusion sub-events 1702 MO), wherein a 0.01 unit dose of infusible fluid 200 is delivered during each of the ten discrete infusion sub-events. Further, one-time infusion event 1614 may include e.g., three-hundred-sixty one-time infusion sub-events (not shown), wherein a 0.1 unit dose of infusible fluid 200 is delivered during each of the three-hundred-sixty one-time infusion sub-events. The number of sub-events defined above and the quantity of infusible fluid 200 delivered during each sub-event is solely for illustrative purposes only and is not intended to be a limitation of this disclosure, as the number of sub-events and/or the quantity of infusible fluid 200 delivered during each sub-event may be increased or decreased depending upon e.g., the design criteria of infusion pump assembly 100 and/or the implementation of fluid delivery process 236.

Before, after, or in between the above-described infusion sub-events, infusion pump assembly 100 may confirm the proper operation of infusion pump assembly 100 through the use of e.g., force sensor 216 (i.e., which may determine the occurrence of an occlusion) and displacement detection device 218 (i.e., which may determine the occurrence of a mechanical failure).

As discussed above, during operation of infusion pump assembly 100, infusible fluid 200 may be delivered to user 202 in accordance with e.g. a defined delivery schedule. For illustrative purposes only, assume that infusion pump assembly 100 is configured to provide 0.10 mL of infusible fluid 200 to user 202 every three minutes. Accordingly, every three minutes, processing logic 204 may provide the appropriate drive signals to motor assembly 214 to allow motor assembly 214 to rotate lead screw assembly 42 the appropriate amount so that partial nut assembly 40 (and therefore plunger assembly 224) may be displaced the appropriate amount in the direction of arrow 230 so that 0.10 mL of infusible fluid 200 are provided to user 202 (via cannula 38).

Processing logic 204 may execute occlusion detection process 238, and occlusion detection process 238 may be configured to monitor one or more events that are occurring within infusion pump assembly 100 to determine whether or not an occlusion (e.g., a blockage) has occurred within e.g. cannula assembly 114.

Referring also to FIGS. 18-19, occlusion detection process 238 may determine 1900 a rate-of-change force reading (e.g., FR01) that corresponds to the delivery of first dose 240 (FIG. 2) of infusible fluid 200.

When determining 1900 the rate-of-change force reading (e.g., FR01), occlusion detection process 238 may determine 1902 an initial force reading prior to dispensing first dose 240 of infusible fluid 200. As discussed above, infusion pump assembly 100 may regularly dispense individual doses of infusible fluid 200 based upon one or more infusion schedules. For example and as discussed above, infusion pump assembly 100 may be configured to dispense 0.10 mL of infusible fluid 200 to user 202 every three minutes.

When determining 1902 the initial force reading prior to dispensing first dose 240 of infusible fluid 200, occlusion detection process 238 may obtain the initial force reading from force sensor 216. Provided that there is not an occlusion within e.g. cannula assembly 114, the initial force reading obtained by occlusion detection process 238 prior to infusion pump assembly 100 dispensing first dose 240 of infusible fluid 200 should be zero pounds. Once occlusion detection process 238 determines 1902 the initial force reading, infusion pump assembly 100 may dispense 1904 first dose 240 of infusible fluid 200 to user 202 via cannula assembly 114. While the system may be described above and/or below as having a force reading of zero pounds prior to and/or subsequent to dispensing infusible fluid 200, this is for illustrative purposes only, as frictional forces and/or backpressure may result in force readings that are slightly higher than zero pounds.

Once infusion pump assembly 100 dispenses 1904 first dose 240 of infusible fluid 200 to user 202, occlusion detection process 238 may determine 1906 a final force reading subsequent to dispensing 1904 first dose 240 of infusible fluid 200. For example, once infusion pump assembly 100 has completely dispensed 1904 first dose 240 of infusible fluid 200 to user 202, occlusion detection process 238 may obtain the final force reading from force sensor 216 in a process similar to that used to obtain the initial force reading from force sensor 216.

Occlusion detection process 238 may determine 1900 the rate-of-change force reading (e.g., FRO1) based, at least in part, upon the initial force reading and the final force reading. For example, occlusion detection process 238 may subtract the initial force reading from the final force reading to determine the net force change that occurred while dispensing (in this particular example) 0.10 mL of infusible fluid 200. As discussed above, provided that there are no occlusions within e.g. cannula assembly 114, the initial force reading (obtained from force sensor 216) should be zero and the final force reading (also obtained from force sensor 216) should also be zero. Accordingly, the rate-of-change force reading (e.g., FRO1) determined 1900 by occlusion detection process 238 should also be zero.

While the system is described above as determining 1906 a final force reading subsequent to dispensing 1904 first dose 240 of infusible fluid 200, this final force reading may actually be based upon the initial force reading that is taken for the next dose of infusible fluid 200. Accordingly, by allowing the initial force reading of the second dose of infusible fluid 200 to provide the data for the final force reading of the first dose of infusible fluid 200, the total number of force readings made may be reduced by 50%.

Once the rate-of-change force reading (e.g., FRO1) is determined, occlusion detection process 238 may store the rate-of-change force reading (e.g., FRO1) within e.g., storage cell 1800 of storage array 1802. Storage array 1802 may be configured as a FIFO (first in, first out) buffer. Storage array 1802 may be configured to allow occlusion detection process 238 to maintain a plurality of historical values for the rate-of-change force readings (e.g., FRO1) discussed above. A typical embodiment of storage array 1802 may include twenty or forty individual storage cells. While storage array 1802 is illustrated in FIG. 18 as being a multi-column storage array, this is for illustrative purposes only and is not intended to be a limitation of this disclosure. For example, storage array 1802 may be a single column storage array in which only the rate-of-change force readings are stored.

Occlusion detection process 238 may process the historical values of the rate-of-change force readings to determine an average rate-of-change force reading over a desired infusible fluid volume/number of infusion cycles. For example, occlusion detection process 238 may determine an average rate-of-change force reading over each forty infusion cycles. Accordingly, occlusion detection process 238 may determine 1908 additional rate-of-change force readings, each of which corresponds to the delivery of additional doses of infusible fluid 200. For example and for illustrative purposes only, occlusion detection process 238 may determine 1908 thirty-nine additional rate-of-change force readings for the next thirty-nine infusion cycles. Each of these thirty-nine rate-of-change force readings may be stored in a unique storage cell of storage array 1802. Once storage array 1802 is completely full (i.e. contains forty rate-of-change force readings), occlusion detection process 238 may determine an average rate-of-change force reading for the set of forty rate-of-change force readings. Once this average rate-of-change force reading is determined, storage array 1802 may be cleared and the process of gathering additional rate-of-change force readings may be repeated.

When determining additional rate-of-change force readings, occlusion detection process 238 may determine 1910 an initial force reading prior to dispensing the additional dose (e.g., dose 242) of infusible fluid 200. Dose 242 of infusible fluid may then be dispensed 1912 by infusion pump assembly 100. Occlusion detection process 238 may determine 1914 a final force reading subsequent to dispensing dose 242 of infusible fluid 200.

Occlusion detection process 238 may determine 1908 the additional rate-of-change force readings (e.g., FR2) based, at least in part, upon the initial force reading and the final force reading for each additional dose of infusible fluid 200. As discussed above, provided that there are no occlusions within e.g. cannula assembly 114, the initial force reading (obtained from force sensor 216) should be zero and the final force reading (also obtained from force sensor 216) should also be zero. Accordingly, the rate-of-change force reading (e.g., FR2) determined 1908 by occlusion detection process 238 should also be zero. As discussed above, once the additional rate-of-change force readings (e.g., FR2) are determined, occlusion detection process 238 may store the rate-of-change force reading (e.g., FR2) within e.g., storage cell 1804 of storage array 1802.

Assume for illustrative purposes that occlusion detection process 238 continues to calculate the rate-of-change force readings in the manner described above and continues to store these calculated rate-of-change force readings within storage array 1802. Further, assume for illustrative purposes that infusion pump assembly 100 continues to operate properly (i.e. without any occlusions) for the first thirty-three infusion cycles. Accordingly, the first thirty-three rate-of-change force readings (FR01-FR33) are all zero, as their respective initial force reading and final force reading were all zero. However, assume for illustrative purposes that an occlusion (e.g. occlusion 244) occurs within cannula assembly 114 prior to calculating the thirty-fourth, rate-of-change force reading (e.g., FR34), which is stored within storage cell 1806. Assume for illustrative purposes that when determining the thirty-fourth rate-of-change force reading (e.g., FR34), occlusion detection process 238 determines 1910 an initial force reading of 0.00 pounds. When infusion pump assembly 100 begins to dispense 1912 the thirty-fourth dose of infusible fluid 200, as occlusion 244 is present within cannula assembly 114, the fluid displaced from reservoir assembly 200 by plunger assembly 224 will not be able to pass through cannula assembly 114. Accordingly, the pressure within reservoir assembly 200 will begin to build. Therefore, assume for illustrative purposes that occlusion detection process 238 determines 1914 a final force reading of 0.50 pounds. Accordingly, occlusion detection process 238 may determine 1908 the rate-of-change force reading (e.g., FR34) to be 0.50 pounds minus 0.00 pounds, for a rate-of-change of 0.50 pounds.

Due to the presence of occlusion 244 within cannula assembly 114, when motor assembly 214 attempts to dispense the next dose of infusible fluid 200, 0.50 pounds of pressure sensed by force sensor 216 will still be present within fluid reservoir 200. Accordingly, when determining the thirty-fifth rate-of-change force reading (e.g., FR35), the initial force reading determined 1910 by occlusion detection process 238 may be the same as the final force reading determined by occlusion detection process 238 when determining the thirty-fourth rate-of-change force reading (e.g., FR34)

Occlusion detection process 238 may determine 1916 an average rate-of-change force reading (e.g., AFR) based, at least in part, upon all or a portion of the rate-of-change force readings included within storage array 1802. Assume for illustrative purposes that occlusion detection process 238 is configured to consider all rate-of-change force readings (e.g., FR01-FR40) included within storage array 1802. Accordingly, occlusion detection process 238 may calculate the mathematical average of all rate-of-change force readings (e.g., FR01-FR40) included within storage array 1802. In this particular example, average rate-of-change force reading (e.g., AFR) has a mathematical value of 0.105 pounds. While the system is described above as being capable of considering all rate-of-change force readings (e.g., FR01-FR40) included within storage array 1802, this is for illustrative purposes only and is not intended to be a limitation of this disclosure, as other configurations are possible. For example, occlusion detection process 238 may be configured to determine 1916 an average rate-of-change force reading (e.g., AFR) once storage array 1802 is populated with e.g., the first five rate-of-change force readings. If determining 1916 an average rate-of-change force reading (e.g., AFR) prior to storage array 1802 being completely populated, any unpopulated rows within storage array 1802 may be populated with zeros.

Occlusion detection process 238 may compare 1918 the average rate-of-change force reading (e.g., AFR) to a threshold rate-of-change force reading to determine if the average rate-of-change force reading (e.g., AFR) exceeds the threshold rate-of-change force reading. If the average rate-of-change force reading does not exceed the threshold rate-of-change force reading, infusion pump assembly 100 may continue 1920 to operate normally. However, if the average rate-of-change force reading exceeds the threshold rate-of-change force reading, an alarm sequence may be initiated 1922 on infusion pump assembly 100. For example, assuming for illustrative purposes that occlusion detection process 238 is configured to have a threshold rate-of-change force reading of 0.90 pounds, only after the average rate-of-change force reading (e.g., AFR) exceeds 0.90 pounds will the alarm sequence be initiated 1920. Thus, in these embodiments, measuring the rate-of-change may ensure alarm sequences are triggered more reliably when actual occlusions have occurred. As described below, user 202, in some embodiments, defines the sensitivity of the system.

The sensitivity of occlusion detection process 238 may be based upon a user-defined sensitivity setting selected 1924 by e.g., user 202. For example, assume that occlusion detection process 238 has two sensitivity settings, namely a high sensitivity setting and a low sensitivity setting. Further, assume that each of the sensitivity settings is associated with a unique manner of determining the rate-of-change force readings included within storage array 1802. As discussed above, occlusion detection process 238 is described above as determining 1900 a rate-of-change force reading (e.g., FR01) that corresponds to the delivery of first dose 240 of infusible fluid 200. Assume that when configured in the high sensitivity setting, occlusion detection process 238 may determine 1900 a rate-of-change force reading that corresponds to the delivery of a comparatively smaller quantity of infusible fluid 200. Further, assume that when configured in the low sensitivity setting, occlusion detection process 238 may determine 1900 a rate-of-change force reading that corresponds to the delivery of a comparatively larger quantity of infusible fluid 200. For example, assume that when in the high sensitivity setting, occlusion detection process 238 determines 1900 a rate-of-change force reading that corresponds to the delivery of 0.10 mL of infusible fluid 200. Further, assume that when in the low sensitivity setting, occlusion detection process 238 determines 1900 a rate-of-change force reading that corresponds to the delivery of a 0.20 mL dose 240 of infusible fluid 200. Accordingly, when placed in the high sensitivity setting, additional measurements are taken and occlusion detection process 238 is more responsive. However, false alarms may occur more frequently. Conversely, when placed in the low sensitivity setting, fewer measurements are taken and occlusion detection process 238 is less responsive. However, false alarms may occur less frequently due to the "averaging" effect of taking fewer measurements. Accordingly, in order to avoid nuisance alarms (or to reduce the number of alarms), the user (e.g. user 202) may select 1924 the low sensitivity setting.

The alarm sequence initiated 1922 may include any combination of visual-based (via display system 104), audible-based (via a audio system 212), and vibration-based alarms (via vibration system 210). User 202 may be able to select between the high-sensitivity setting and the low-sensitivity setting via one or more of input system 208 and display system 104.

While infusion pump assembly 100 is described above as delivering a plurality of identically-sized doses of infusible fluid 200 and calculating a rate-of-change force reading (e.g., FR01) for each dose of infusible fluid 200, this is for illustrative purposes only and is not intended to be a limitation of this disclosure. Specifically, infusion pump assembly 100 may be configured to provide non-identical doses of infusible fluid 200. Further and as discussed above, infusion pump assembly 100 may be configured to allow user 202 to manually administer a "bolus" dose of infusible fluid 200 in a size determined by user 202. Accordingly, occlusion detection process 238 may be configured to monitor the volume of infusible fluid 200 dispensed in each dose and may be configured to populate storage array 1802 so that each rate-of-change force reading (e.g., FR01) included within storage array 1802 is indicative of the rate-of-change force sensed by occlusion detection process 238 when dispensing an equivalent quantity of infusible fluid 200. Accordingly, occlusion detection process 238 may be configured to "normalize" the rate-of-change force readings determined based upon the quantity of infusible fluid delivered.

For example, assume that occlusion detection process 238 is configured so that a storage cell included within storage array 1802 is populated each time 0.10 mL of infusible fluid 200 is dispensed. Assume for illustrative purposes only that user 202 decides to dispense a 0.25 mL dose of infusible fluid 200. As the 0.25 mL dose of infusible fluid 200 is greater than the 0.10 mL increments at which occlusion detection process 238 is configured to populate storage array 1802, occlusion detection process 238 may record multiple entries (and, therefore, populate multiple storage cells) within storage array 1802 for the single 0.25 mL dose of infusible fluid 200.

Specifically, assume that the initial force reading determined 1910 prior to delivering the 0.25 mL dose of infusible fluid 200 is 0.00 pounds and the final force reading determined 1914 after dispensing 1912 the 0.25 mL dose of infusible fluid 200 is 1.00 pounds. As the 0.25 mL dose of infusible fluid 200 is two-and-a-half times the 0.10 mL increments in which occlusion detection process 238 is configured to populate storage array 52, occlusion detection process 238 may "normalize" this rate-of-change force reading. Specifically, occlusion detection process 238 may divide 1.00 pounds by 0.25 mL to determine that the force changed 0.40 pounds per 0.10 mL. Accordingly, occlusion detection process 238 may calculate a rate-of-change force reading of 0.40 pounds for the first 0.10 mL dose of infusible fluid 200, 0.40 pounds for the second 0.10 mL dose of infusible fluid 200, and 0.20 pounds for the last 0.05 mL dose of infusible fluid 200.

Accordingly, occlusion detection process 238 may populate storage array 1802 so that a first storage cell (associated with the first 0.10 mL dose of infusible fluid 200) defines an initial force reading of 0.00 pounds, a final force reading of 0.40 pounds and a rate-of-change force reading of 0.40 pounds. Further, occlusion detection process 238 may populate storage array 1802 so that a second storage cell (associated with the second 0.10 mL dose of infusible fluid 200) defines an additional force reading of 0.40 pounds, a final force reading of 0.80 pounds and a rate-of-change force reading of 0.40 pounds.

Concerning the remaining 0.05 mL of the 0.25 mL dose of infusible fluid 200, as this is less than the 0.10 mL increment at which occlusion detection process 238 is configured to populate storage array 52, the next cell within storage array 1802 will not be populated until an additional 0.05 mL dose of infusible fluid 200 is dispensed.

Continuing with the above-stated example, assume for illustrative purposes that infusion pump assembly 100 administers a 0.15 mL dose of infusible fluid 200. Occlusion detection process 238 may combine the first 0.05 mL of the 0.15 mL dose of infusible fluid 200 with the remaining 0.05 mL of the 0.25 mL dose of infusible fluid 200 to form a complete 0.10 mL increment for recording within storage array 1802.

Again, occlusion detection process 23 8 may "normalize" the 0.15 mL dose of infusible fluid 200. Assume for illustrative purposes that when dispensing the 0.15 mL of infusible fluid 200, occlusion detection process 238 determines an initial force reading of 1.00 pounds and a final force reading of 1.60 pounds. In the manner described above, occlusion detection process 238 may divide 0.60 pounds (i.e., 1.60 pounds minus 1.00 pounds) by 0.15 mL to determine that the force changed 0.40 pounds per 0.10 mL. Accordingly, occlusion detection process 238 may calculate a rate-of-change force reading of 0.20 pounds for the first 0.05 mL of the 0.15 mL dose of infusible fluid 200, and 0.40 pounds for the remaining 0.10 mL of the 0.15 mL dose of infusible fluid 200.

Accordingly, occlusion detection process 238 may populate storage array 1802 so that a third storage cell (associated with the combination of the first 0.05 mL of the 0.15 mL dose of infusible fluid 200 with the remaining 0.05 mL of the 0.25 mL dose of infusible fluid 200) defines an initial force reading of 0.80 pounds (i.e., which is the final force reading after the second 0.10 mL of the 0.25 mL dose of infusible fluid 200), a final force reading of 1.20 pounds (i.e., the sum of the initial force reading of 1.00 pounds plus the 0.20 pound offset for the first 0.05 mL of the 0.15 mL dose of infusible fluid 200) and a rate-of-change force reading of 0.40 pounds. Further, occlusion detection process 238 may populate storage array 1802 so that a fourth storage cell (associated with the last 0.10 mL of the 0.15 mL dose of infusible fluid 200) defines an initial force reading of 1.20 pounds, a final force reading of 1.60 pounds and a rate-of-change force reading of 0.40 pounds.

In addition to comparing 1918 the average rate-of-change force reading (e.g., AFR) to a threshold rate-of-change force reading to determine if the average rate-of-change force reading (e.g., AFR) exceeds the threshold rate-of-change force reading, occlusion detection process 238 may compare 1926 one or more of the initial force reading and the final force reading to a threshold force reading to determine if either the initial force reading or the final force reading exceeds the threshold force reading. If either of the initial force reading or the final force reading exceeds the threshold force reading, an alarm sequence maybe initiated 1928 on infusion pump assembly 100.

For example, occlusion detection process 238 may define a threshold force reading, which if exceeded by either the initial force reading (which is determined prior to dispensing a dose of infusible fluid 200) or the final force reading (which is determined after dispensing a dose of infusible fluid 200), an occlusion is deemed to be occurring. Examples of such a threshold force reading is 4.00 pounds. Therefore, if after dispensing a dose of infusible fluid 200, occlusion detection process 238 determines a final force reading of 5.20 pounds, occlusion detection process 238 may initiate 1928 an alarm sequence, as 5.20 pounds exceeds the 4.00 threshold force reading. The alarm sequence initiated 1928 may include any combination of visual-based (via display system 104), audible-based (via audio system 212), and vibration-based alarms (via vibration system 210).

As discussed above, infusion pump assembly 100 may include primary power supply 220 configured to power infusion pump assembly 100. Before and/or after dispensing a dose of infusible fluid 200, occlusion detection process 238 may compare 1930 the actual voltage level of primary power supply 220 to a minimum voltage requirement to determine if the actual voltage level of primary power supply 220 meets the minimum voltage requirement. If the actual voltage level does not meet the minimum voltage requirement, occlusion detection process 238 may initiate 1932 an alarm sequence on infusion pump assembly 100. The alarm sequence initiated 1932 may include any combination of visual-based (via display system 104), audible-based (via audio system 212), and vibration-based alarms (via vibration system 210). For example, assume for illustrative purposes that primary power supply 220 is a 5.00 VDC battery. Further, assume that the minimum voltage requirement is 3.75 VDC (i.e., 75% of normal voltage). Accordingly, if occlusion detection process 238 determines 1930 that the actual voltage level of primary power supply 220 is 3.60 VDC, occlusion detection process 238 may initiate 1932 an alarm sequence on infusion pump assembly 100.

Additionally, occlusion detection process 238 may monitor one or more of the displaceable mechanical components included within infusion pump assembly 100 to determine 1934 if one or more displaceable mechanical components included within infusion pump assembly 100 were displaced an expected displacement in response to delivering a dose of infusible fluid 200. If the displaceable mechanical components monitored were not displaced the expected displacement in response to delivering a dose of infusible fluid 200, occlusion detection process 238 may initiate 1936 an alarm sequence on infusion pump assembly 100. The alarm sequence initiated 1936 may include any combination of visual-based (via display system 104), audible-based (via audio system 212), and vibration-based alarms (via vibration system 210).

For example, upon processing logic 204 energizing motor assembly 214 to dispense 0.10 mL of infusible fluid 200, occlusion detection process 238 may (via displacement detection device 218) confirm that partial nut assembly 226 did indeed move the expected displacement. Accordingly, in the event that partial nut assembly 226 does not move the expected displacement, a mechanical failure (e.g. the failure of partial nut assembly 226, the failure of lead screw assembly 228, the failure of motor assembly 214) may have occurred. In the event that the expected displacement of partial nut assembly 226 cannot be confirmed, occlusion detection process 238 may initiate 1936 the alarm sequence on infusion pump assembly 100.

When determining whether partial nut assembly 226 was displaced the expected amount, tolerances may be utilized. For example, assume that to deliver a 0.10 mL dose of infusible fluid 200, occlusion detection process 238 may expect to see partial nut assembly 226 displaced 0.050 inches. Accordingly, occlusion detection process 238 may utilize a 10% error window in which movement of partial nut assembly 226 of less than 0.045 inches (i.e., 10% less than expected) would result in occlusion detection process 238 initiating 1936 the alarm sequence on infusion pump assembly 100.

In one embodiment of displacement detection device 218, displacement detection device 218 includes one or more light sources (not shown) positioned on one side of partial nut assembly 226 and one or more light detectors (not shown) positioned on the other side of partial nut assembly 226. Partial nut assembly 226 may include one or more passages (not shown) through which the light from the one or more light sources (not shown) included within displacement detection device 218 may shine and may be detected by the one or more light detectors (not shown) included within displacement detection device 218.

Referring now to FIG. 20, in some embodiments of the infusion pump system, the infusion pump may be remotely controlled using remote control assembly 2000. Remote control assembly 2000 may include all, or a portion of, the functionality of the pump assembly itself. Thus, in some exemplary embodiments of the above-described infusion pump assembly, the infusion pump assembly (not shown, see FIGS. 1A-1F, amongst other FIGS.) may be configured via remote control assembly 2000. In these particular embodiments, the infusion pump assembly may include telemetry circuitry (not shown) that allows for communication (e.g., wired or wireless) between the infusion pump assembly and e.g., remote control assembly 2000, thus allowing remote control assembly 2000 to remotely control infusion pump assembly 100'. Remote control assembly 2000 (which may also include telemetry circuitry (not shown) and may be capable of communicating with infusion pump assembly) may include display assembly 2002 and an input assembly, which may include one or more of the following: an input control device (such as jog wheel 2006, slider assembly 2012, or another conventional mode for input into a device), and switch assemblies 2008, 2010. Thus, although remote control assembly 2000 as shown in FIG. 20 includes jog wheel 2006 and slider assembly 2012, some embodiments may include only one of either jog wheel 2006 or slider assembly 2012, or another conventional mode for input into a device. In embodiments having jog wheel 2006, jog wheel 2006 may include a wheel, ring, knob, or the like, that may be coupled to a rotary encoder, or other rotary transducer, for providing a control signal based upon, at least in part, movement of the wheel, ring, knob, or the like.

Remote control assembly 2000 may include the ability to pre-program basal rates, bolus alarms, delivery limitations, and allow the user to view history and to establish user preferences. Remote control assembly 2000 may also include glucose strip reader 2014.

During use, remote control assembly 2000 may provide instructions to the infusion pump assembly via a wireless communication channel established between remote control assembly 2000 and the infusion pump assembly. Accordingly, the user may use remote control assembly 2000 to program/configure the infusion pump assembly. Some or all of the communication between remote control assembly 2000 and the infusion pump assembly may be encrypted to provide an enhanced level of security.

A number of implementations have been described. Nevertheless, it will be understood that various modifications may be made. Accordingly, other implementations are within the scope of the following claims.

What is claimed is:

1. A delivery device for delivering an infusion medium to a user, the device comprising:
   first and second housing portions configured to be selectively engaged together for operation and selectively separated from each other;
   a reservoir supported by the first housing portion, the reservoir including a reservoir housing having an interior volume, a plunger head moveable within the reservoir interior to selectively change the volume of the reservoir interior and a plunger rod extending from the plunger head to a position outside of the reservoir housing, wherein the plunger rod comprises a threaded portion for at least a portion of the rod's length;
   a nut member being supported in a fixed relation with the plunger rod of the reservoir, the nut member having a structure for engaging the threaded portion of the plunger rod in any one of a plurality of positions in a first dimension relative to the nut member;
   a rotatable lead shaft supported by the second housing portion for rotation about a rotary axis; and
   a sensor arranged to detect a detectable feature to provide a signal corresponding to the position of the detectable feature, wherein the position of the detectable feature corresponds to a fill state of the reservoir.

2. The device of claim 1, wherein the nut member includes the detectable feature.

3. The device of claim 1, further comprising a locking tab.

4. The device of claim 3, further comprising a pump barrel inside a pump barrel housing, the pump barrel accommodates the reservoir.

5. The device of claim 4, further comprising a locking disc at a terminus of the pump barrel, the locking disc having a clearance hole for the plunger rod and at least one locking tab notch, the locking disc being in close proximity with the locking tab.

6. The device of claim 5, wherein the locking disc rotates upon torque being applied to the reservoir, the locking disc rotating from a-non-loaded position to a loaded position with respect to said plunger rod and a drive screw.

7. A delivery device for delivering an infusion medium to a user, the device comprising:
   first and second housing portions configured to be selectively engaged together for operation and selectively separated from each other;
   a reservoir supported by the first housing portion, the reservoir including:
     a reservoir housing having an interior volume;
     a plunger moveable within the reservoir interior to selectively change the volume of the reservoir interior; and
     a plunger rod extending from the plunger, the plunger rod including a threaded portion having an open side, wherein the plunger rod includes a detectable feature; and
   a drive screw supported by the second housing portion for rotation about a rotary axis, the drive screw being engageable with the threaded portion of the plunger rod as the first and second housing portions are brought together for operative engagement; the delivery device further comprising a sensor arranged to detect the detectable feature to provide a signal corresponding to the position of the detectable feature, wherein the position of the detectable feature corresponds to a fill state of the reservoir.

8. The device of claim 7, wherein the nut member includes a detectable feature.

9. The device of claim 7, further comprising a locking tab.

10. The device of claim 9, further comprising a pump barrel inside a pump barrel housing, the pump barrel accommodates the reservoir.

11. The device of claim 10, further comprising a locking disc at a terminus of the pump barrel, the locking disc having a clearance hole for the plunger rod and at least one locking tab notch, the locking disc being in close proximity with the locking tab.

12. The device of claim 11, wherein the locking disc rotates upon torque being applied to the reservoir, the locking disc rotating from a-non-loaded position to a loaded position with respect to said plunger rod and a drive screw.

* * * * *